United States Patent
Kim et al.

(10) Patent No.: US 9,029,105 B2
(45) Date of Patent: May 12, 2015

(54) MICROORGANISM PRODUCING L-METHIONINE PRECURSOR AND METHOD OF PRODUCING L-METHIONINE AND ORGANIC ACID FROM THE L-METHIONINE PRECURSOR

(71) Applicant: CJ Cheiljedang Corporation, Seoul (KR)

(72) Inventors: So-young Kim, Gyeonggi-do (KR); Kwang-myung Choi, Gyeonggi-do (KR); Yong-uk Shin, Gyeonggi-do (KR); Hye-won Um, Gyeonggi-do (KR); Kyung-oh Choi, Seoul (KR); Jin-sook Chang, Seoul (KR); Young-wook Cho, Seoul (KR); Young-hoon Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/752,907

(22) Filed: Jan. 29, 2013

(65) Prior Publication Data
US 2013/0231503 A1  Sep. 5, 2013

Related U.S. Application Data

(63) Continuation of application No. 12/066,111, filed as application No. PCT/KR2007/003650 on Jul. 30, 2007, now Pat. No. 8,426,171.

(30) Foreign Application Priority Data

Jul. 28, 2006 (KR) ............ 10-2006-0071581
Jul. 27, 2007 (KR) ............ 10-2007-0076045

(51) Int. Cl.
C12P 13/12 (2006.01)
C12P 21/04 (2006.01)
(Continued)

(52) U.S. Cl.
CPC ............ *C12P 13/12* (2013.01); *C12N 9/1029* (2013.01); *C12N 9/1085* (2013.01); *C12P 7/46* (2013.01); *C12P 13/06* (2013.01); *C07C 323/58* (2013.01)

(58) Field of Classification Search
CPC .......... C07C 323/00; C12P 13/12; C12P 7/46
USPC ............................................. 435/113, 41, 71
See application file for complete search history.

(56) References Cited

U.S. PATENT DOCUMENTS 7,211,415 B2  5/2007 Rieping et
7,238,502 B2  7/2007 Kröger et al.
(Continued)

FOREIGN PATENT DOCUMENTS

CN   1370836   9/2002
CN   1379111   11/2002
(Continued)

OTHER PUBLICATIONS

Lee et al., Methionine biosynthesis and its regulation in *Corynebacterium glutamicum*: parallel pathways of transsulfuration and direct sulfhydrylation, Appl Microbiol Biotechnol (2003), vol. 62, pp. 459-467.*

(Continued)

*Primary Examiner* — Alexander Kim
(74) *Attorney, Agent, or Firm* — Swanson & Bratschun, L.L.C.

(57) ABSTRACT

The present invention relates to a method for producing L-methionine, comprising: i) culturing an L-methionine precursor-producing microorganism strain in a fermentation solution, so that the L-methionine precursor accumulates in the solution; and ii) mixing a converting enzyme and methylmercaptan or its salts with at least a portion of the solution to convert the accumulated L-methionine precursor into L-methionine, as well as to microorganism strains used in each step.

16 Claims, 8 Drawing Sheets

(51) Int. Cl.

| | | |
|---|---|---|
| C12P 1/00 | (2006.01) | |
| C12N 9/10 | (2006.01) | |
| C12P 7/46 | (2006.01) | |
| C12P 13/06 | (2006.01) | |
| C07C 323/58 | (2006.01) | |

(56) References Cited

U.S. PATENT DOCUMENTS

| | | | |
|---|---|---|---|
| 7,851,180 | B2 | 12/2010 | Shin et al. |
| 8,283,152 | B2 | 10/2012 | Kim et al. |
| 8,426,171 | B2 | 4/2013 | Kim et al. |
| 2002/0049305 | A1 | 4/2002 | Bathe et al. |
| 2003/0092026 | A1 | 5/2003 | Rey et al. |
| 2004/0199941 | A1 | 10/2004 | San et al. |
| 2005/0054060 | A1 | 3/2005 | Chateau et al. |
| 2006/0003425 | A1 | 1/2006 | Kroger et al. |
| 2006/0270013 | A1 | 11/2006 | Chateau et al. |
| 2009/0253186 | A1 | 10/2009 | Kim et al. |
| 2010/0184164 | A1 | 7/2010 | Kim et al. |

FOREIGN PATENT DOCUMENTS

| | | |
|---|---|---|
| EP | 1253195 | 10/2008 |
| EP | 2108693 A2 | 10/2009 |
| JP | 1972-037033 | 9/1972 |
| JP | 2000/139471 | 5/2000 |
| JP | 2005/537024 | 12/2005 |
| KR | 10-1992-0008365 | 9/1992 |
| WO | WO 93/17112 * | 9/1993 |
| WO | WO 2004/035617 | 4/2004 |
| WO | WO 2004/038013 | 5/2004 |
| WO | WO 2004/069996 | 8/2004 |
| WO | WO 2004/076659 | 9/2004 |
| WO | WO 2005/052180 | 6/2005 |
| WO | WO 2005/075625 | 8/2005 |
| WO | WO 2005/108561 | 11/2005 |
| WO | WO 2006/001616 | 1/2006 |
| WO | WO 2006/082252 | 8/2006 |
| WO | WO 2006/138689 | 12/2006 |
| WO | WO 2007/012078 | 1/2007 |
| WO | WO 2007/077041 | 7/2007 |
| WO | WO 2007/116955 | 10/2007 |
| WO | WO 2008/013432 | 1/2008 |
| WO | WO 2008/033001 | 3/2008 |
| WO | WO 2008/039177 | 4/2008 |
| WO | WO 2008/127240 | 10/2008 |

OTHER PUBLICATIONS

Kanzaki et al., Purification and characerization of cystathionine γ-synthase type II from *Bacillus sphaericus*., Eur. J. Biochem. (1987), vol. 163, pp. 105-112.*
Smith et al., Utilization of S-methylcysteine and methylmercaptan by methionineless mutants of neurospora and the pathway of their conversion to methionine II. Enzyme studies., Biochimica et Biophysica Acta (BBA) (1969), vol. 184, Issue 1, pp. 130-138.*
Moore et al., Methionine biosynthesis from S-methylcysteine by thiomethyl transfer in Neurospora. Biochem Biophys Res Commun. (1967), vol. 28(3), pp. 474-479. p. 474 only.*
Moore et al., Methionine biosynthesis from S-methylcysteine by thiomethyl transfer in Neurospora. Biochem Biophys Res Commun. (1967), vol. 28(3), pp. 474-479.*
EP Search Report issued Aug. 27, 2013, in EP Application No. 13178074.4.
Smith et al. (1969) Biochimica Et Biophysica ACTA 184: 130-138, "Utilization of S-methylcysteine and methylmercaptan by methionineless mutants of Neurospora and the pathway of their conversion to methionine".
Allardyce et al. (2006) Journal of Microbiological Methods 65:361-365 "Detection of volatile metabolites produced by bacterial growth in blood culture media by selected ion flow tube mass spectrometry (SIFT-MS)".

Andersen, et al. (1998) Journal of Bacteriology 180(17):4497-4507, "Molecular characterization and sequence of a methionine biosynthetic locus from *Pseudomonas* methionine".
Belfaiza, et al. (1998) Journal of Bacteriology 180(2):250-255, "Direct sulfhydrylation for methionine biosynthesis in *Leptospira meyeri*".
Biran et al. (2003) Molecular Microbiology 37(6):1436-1443 "Control of methionine biosynthesis in *Escherichia coli* by proteolysis".
Blattner, et al. (1997) Science 277(5):1453-1462, "The Complete Genome Sequence of *Escherichia coli* K-12".
Bourhy et al. (1997) Journal of Bacteriology 179(13):4396-4398 "Homoserine O-Acetyltransferase, Involved in the *Leptospira meyeri* Methionine Biosynthetic Pathway, Is Not Feedback Inhibited".
Brown, et al. (1977) Journal of General Microbiology 102:327-336, "The Enzymic Interconversion of Acetate and Acetyl-coenzyme A in *Escherichia coli*".
Browning,et al. (2004) Molecular Microbiology 51(1): 241-254, "Modulation of CRP-dependent transcription at the *Escherichia coli* acsP2 promoter by nucleoprotein complexes: anti-activation by the nucleoid proteins FIS and IHF".
Carrier, et al. (1999) Biotechnology Progress 15:58-64, "Library of synthetic 5' secondary structures to manipulate mRNA stability in *Escherichia coli*".
Dai, et al. (2004) Chinese Journal of Applied & Environmental Biology 10(1):113-115, "Over-Expression, Purification and Characterization of Acetyl-CoA Synthetase from *Sinorhizobium meliloti*" (English abstract).
Database UniProt (2010) Accession No. A0QSZ0, "RecName: Full=Homoserine O-acetyltransferase; EC=2.3.1.31," dated Nov. 2, 2010, 2 pages (XP-002611947).
Database UniProt (2010) Accession No. P57714, "RecName: Full=Homoserine O-acetyltransferase; EC=2.3.1.31," dated Nov. 2, 2010, 2 pages (XP-002611946).
Database UniProt (2010) Accession No. Q9RVZ8, "RecName: Full=Homoserine O-acetyltransferase; EC=2.3.1.31," dated Nov. 2, 2010, 2 pages (XP-002611972).
Datsenko & Wanner (2000) PNAS 97(12):6640-6645, "One-step inactivation of chromosomal genes in *Escherichia coli* K-12 using PCR products".
EP Search Report issued Mar. 29, 2011, in EP Application No. 07793305.9.
Extended European Search Report (2010), European Application No. 10250455.2, dated Dec. 14, 2010, 8 pages.
Extended Search Report and Written Opinion prepared by the European Patent Office as International Searching Authority for European Patent Application 07793305 9, mailed Nov. 21, 2011, 5 pages.
Flavin and Slaughter (1967) Biochemica Et. Biophysica Acta. 132:400-405 "Enzymatic Synthesis of Homocysteine or Methionine Directly from O-succinyl-homoserine".
Fleischmann, et al. (2006) "homoserine O-acetyltransferase [*Mycobacterium smegmatis* str. MC2 155]," NCBI Ref. Seq. YP 886028.1, URL: http://www.ncbi.nlm.nih.gov/protein/118469217, download date Apr. 3, 2012.
Fleischmann, et al. (2006) NCBI Ref. Seq. YP__886028 homoserine O-acetyltransferase [*Mycobacterium smegmatis* str. MC2155], URL: http://www.ncbi.nlm.nih.gov/protein/YP__886028.
Franch, et al. (2000) Current Opinion in Microbiology 3:159-164, "U-turns and regulatory RNAs".
GenBank (2002) Accession No. AAL90885, Mar. 19, 2002, 1 page.
GenBank (2007) Accession No. NP__294596, Dec. 3, 2007, 2 pages.
Giovanelli and Mudd (1968) Biochemical and biophysical research communications 31:275-280 "Sulfuration of O-acetylhomoserine and O-acetylserine by two enzyme fractions from spinach".
Gomes, et al. (2005) Enzyme and Microbial Technology 37:3-18, "Production of L-methionine by submerged fermentation: A review".
Gophna, et al. (2005) Gene 355:48-57, "Evolutionary plasticity of methionine biosynthesis".
Guo et al. (2004) Proc. Natl. Acad. Sci. 101(25):9205-9210 "Protein Tolerance to Random Amino Acid Change".

(56) References Cited

OTHER PUBLICATIONS

Hacham et al. (2003) Molecular biology and evolution 20:1513-1520 "In vivo analysis of various substrates utilized by cystathionine gamma-synthase and O-acetylhomoserine sulfhydrylase in methionine biosynthesis".

Hayashi, et al. (2006) Molecular Systems Biology doi:10.1038/msb4100049, pp. 1-5, "Highly accurate genome sequences of *Escherichia coli* K-12 strains MG1655 and W3110".

Hill and Preiss (1998) Biochemical and Biophysical Research Communications 244:573-577 "Functional Analysis of Conserved Histidines in ADP-Glucose Pyrophosphorylase from *Escherichia coli*".

"homoserine O-acetyltransferase [*Pseudomonas aeruginosa* PA01]," NCBI Ref. Seq. NP 249081.1, URL: http://www.ncbi.nlm.nih.gov/protein/NP_249081.1, download date Apr. 3, 2012.

Hwang (2002) Aspartokinase I-homoserine dehydrogenase |UniProtKB/Swiss-Prot:: Q8RMX0, URL: http://www.ncbi.nlm.nih.gov/protein/Q8RMX0.

Hwang et al. (2007) Journal of microbiology and biotechnology 17(6):1010-1017 "Biochemical analysis on the parallel pathways of methionine biosynthesis in *Corynebacterium glutamicum*".

International Search Report for PCT/KR2007/003650 dated Nov. 5, 2007.

Jensen & Hammer (1998) Biotechnology and Bioengineering 58(2-3):191-195, "Artificial promoters for metabolic optimization".

Jeon et al. (2001) J Hepatol. 34(3):395-401 "S-adenosylmethionine protects post-ischemic mitochondrial injury in rat liver".

Krömer et al. (2006) Journal of Bacteriology 609-618 "Accumulation of Homolanthionine and Activation of a Novel Pathway for Isoleucine Biosynthesis in *Corynbacterium glutamicum* McbR Deletion Strains".

Krömer et al. (2006) Metabolic Engineering 8:353-369 "Metabolic pathway analysis for rational design of L-methionine production by *Escherichia coli* and *Corynebacterium glutamicum*".

Kumar and Gomes (Epub Oct. 24, 2004) Biotechnology Advances 23:41-61 "Mehionine production by fermentation".

Kumari, et al. (1995) Journal of Bacteriology 177(10):2878-2886, "Cloning, Characterization, and Functional Expression of acs, the Gene Which Encodes Acetyl Coenzyme A Synthetase in *Escherichia coli*".

Lazar et al. (1988) Molecular and Cellular Biology 8(3):1247-1252 "Transforming Growth Factor α: Mutation of Aspartic Acid 47 and Leucine 48 Results in Different Biological Activities".

Lin, et al. (2006) Appl. Microbiol. Biotechnol. 71:870-874, "Acetyl-CoA synthetase overexpression in *Escherichia coli* demonstrates more efficient acetate assimilation and lower acetate accumulation: a potential tool in metabolic engineering".

Lockwood et al., (Sep.-Oct. 2000) Audiol Neurootol. 5(5):263-266, "D-Methionine Attenuates Inner Hair Cell Loss in Carboplatin-Treated Chinchillas".

Mato et al. ( 2002) FASEB J. 16(1):15-26 "S-Adenosylmethionine: a control switch that regulates liver function".

Mischoulon et al. (2002) Am J Clin Nutr. 76(5):1158S-1161S "Role of S-adenosyl-L-methionine in the treatment of depression: a review of the evidence1-4".

Nakamori et al. (1999) Appl Microbiol Biotechnol 52:179-185 "Mechanism of L-methionine overproduction by *Escherichia coli*: the replacement of Ser-54 by Asn in the MetJ protein causes the derepression of L-methionine biosynthetic enzymes".

Office Action (Aug. 27, 2012) from Chinese App. No. 2010/10144874.6, pp. 1-10, English translation.

Park et al. (2007) Metabolic engineering 9:327-336 "Characteristics of methionine production by an engineered *Corynebacterium glutamicum* strain".

Posfai, et al. (1997) Journal of Bacteriology 179(13):4426-4428, "Versatile insertion plasmids for targeted genome manipulations in bacteria: isolation, deletion, and rescue of the pathogenicity island LEE of *Escherichia coli* O157:H7 genome".

Qiu & Goodman (1997) Journal of Biological Chemistry 272(13):8611-8617, "The *Escherichia coli* polB locus is identical to dinA, the structural gene for DNA polymerase II".

Rambaldi et al. (2001) Cochrane Database Syst Rev. (4):CD002235 "S-adenosyl-L-methionine for alcoholic liver diseases".

Rock, et al. (2003) Journal of Bacteriology, 185(11):3410-3415, "Role of Feedback Regulation of Pantothenate Kinase (CoaA) in Control of Coenzyme A Levels in *Escherichia coli*".

Rowbury, R.J. (1964) J. gen. Microbiol. 37:171-180 "The Accumulation of O-Succinylhomoserine by *Escherichia coli* and *Salmonella typhimurium*".

Rückert, et al. (2003) Journal of Biotechnology 104:213-228, "Genome-wide analysis of the L-methionine biosynthetic pathway in *Corynebacterium glutamicum* by targeted gene deletion and homologous complementation".

Sander et al. (2003) ACP J Club.138(1):21 "Review: S-adenosylmethionine treats osteoarthritis as effectively as nonsteroidal anti-inflammatory drugs with fewer adverse effects".

Soeken et al. (2002) J Fam Pract. 51(5):425-430 "Safety and efficacy of S-adenosylmethionine (SAMe) for osteoarthritis".

Soeken, et al. (2003) ACP Journal Club 138(1):21, "Review: S-adenosylmethionine treats osteoarthritis as effectively as nonsteroidal anti-inflammatory drugs with fewer adverse effects".

Song & Jackowski (1992) Journal of Bacteriology 174(20):6411-6417, "Cloning, Sequencing, and Expression of the Pantothenate Kinase (coaA) Gene of *Escherichia coli*".

Song & Jackowski (1994) Journal of Biological Chemistry 269(43):27051-27058, "Kinetics and Regulation of Pantothenate Kinase from *Escherichia coli*".

Vallari & Jackowski (1988) Journal of Bacteriology 170(9):3961-3966, "Biosynthesis and Degradation Both Contribute to the Regulation of Coenzyme A Content in *Escherichia coli*".

Villaverde, et al. (1993) Applied and Environmental Microbiology 59(10):3485-3487, "Fine regulation of cI857-controlled gene expression in continuous culture of recombinant *Escherichia coli* by temperature".

Vitreschak, et al. (2004) FEMS Microbiology Letters 234:357-370, "Attenuation regulation of amino acid biosynthetic operons in proteobacteria: comparative genomics analysis".

Wacey et al. (1999) Hum Genet 104:15-22 "Disentangling the perturbational effects of amino acid substitutions in the DNA-binding domain of p53".

Wente & Schachman (1991) Journal of Biological Chemistry 266(31):20833-20839, "Different amino acid substitutions at the same position in the nucleotide-binding site of aspartate transcarbamoylase have diverse effects on the allosteric properties of the enzyme".

White, et al. (1999) "homoserine O-acetyltransferase [*Deinococcus radiodurans* R1]," NCBI Ref. Seq. NP 294596.1, URL:http://www.ncbi.nlm.nih.gov/protein/NP_294596.1, download date Apr. 3, 2012.

White, et al. (1999) Science, 286(5444):1571-1577, "Genome Sequence of the Radioresistant Bacterium *Deinococcus radiodurans* R1".

White, et al. (1999) UniProtKB/Swiss-Prot Q9RVZ8 homoserine O-acetyltransferase [*Deinococcus radiodurans* R1]. URL: http://www.ncbi.nlm.nih.gov/protein/Q9RVZ8.

Yamagata (1989) Biochimie 71:1125-1143 "Roles of O-acetyl-L-homoserine sulfhydrylases in microorganisms".

Yano, et al. (1998) PNAS, USA 95:5511-5515 "Directed evolution of an aspartate aminotransferase with new substrate specificities".

Yeom et al. (2004) Journal of microbiology and biotechnology 14:373-378 "Regulation of enzymes involved in methionine biosynthesis in *Corynebacterium glutamicum*".

Zhang, et al. (2006) Journal of the Fourth Military Medical University 27(23):2135-2138, "Expression, purification and enzyme activity determination of pantothenate kinase from *Mycobacterium tuberculosis*" (English abstract).

Hwang et al. (2002) Journal of Bacteriology 184(5):1277-1286 "*Corynebacterium glutamicum* Utilizes both Transsulfuration and Direct Sulfhydrylation Pathways for Methionine Biosynthesis".

* cited by examiner

Fig. Met synthesis with OSHS

Fig. Met synthesis with OAHS

SEQUENCE LISTING

```
<160> NUMBER OF SEQ ID NOS: 83

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic
      primer for amplification of Chloramphenichol

<400> SEQUENCE: 1
ttactctggt gcctgacatt tcaccgacaa agcccaggga acttcatcac gtgtaggctg      60
gagctgcttc                                                            70

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: Synthetic
      primer for amplification of Chloramphenichol

<400> SEQUENCE: 2 ttacccttg tttgcagccc ggaagccatt ttccaggtcg gcaattaaat catatgaata       60
tcctccttag                                                            70

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence: Synthetic
      primer for amplification of kanamycin

<400> SEQUENCE: 3
aaagaatatg ccgatcggtt cgggcttagg ctccagtgcc tgttcggtgg gtgtaggctg      60
gagctgcttc                                                            70

<210> SEQ ID NO 4
<211> LENGTH: 70
<212> TYPE: DNA
<213> ORGANISM: Artificial Sequence
<220> FEATURE:
```

<223> OTHER INFORMATION: Description of Artificial Sequence: Synthetic
      primer for amplification of kanamycin

<400> SEQUENCE: 4
agacaaccga catcgctttc aacattggcg accggagccg ggaaggcaaa catatgaata    60
tcctccttag                                                           70

<210> SEQ ID NO 5
<211> LENGTH: 71
<212> TYPE: DNA
<213> ORGANISM: Artificial Sequence
<220> FEATURE:
<223> OTHER INFORMATION: Description of Artificial Sequence: Synthetic
      primer for amplification of Chloramphenichol

<400> SEQUENCE: 5
atggctgaat ggagcggcga atatatcagc ccatacgctg agcacggcaa ggtgtaggct    60
ggagctgctt c                                                         71

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      primer for amplification of Chloramphenichol

<400> SEQUENCE: 6
gtattcccac gtctccgggt taatccccat ctcacgcatg atctccatat gaatatcctc    60
cttag                                                                65

<210> SEQ ID NO 7
<211> LENGTH: 19
<212> TYPE: DNA
<213> ORGANISM: Escherichia coli

<400> SEQUENCE: 7
gggctttgtc ggtgaaatg                                                 19

<210> SEQ ID NO 8
<211> LENGTH: 19
<212> TYPE: DNA
<213> ORGANISM: Escherichia coli

<400> SEQUENCE: 8
actttgcgat gagcgagag                                                 19

<210> SEQ ID NO 9
<211> LENGTH: 28
<212> TYPE: DNA
<213> ORGANISM: Escherichia coli

<400> SEQUENCE: 9
aatggatcct gccgtgagcg gcgaatac                                       28

<210> SEQ ID NO 10
<211> LENGTH: 28
<212> TYPE: DNA
<213> ORGANISM: Escherichia coli

<400> SEQUENCE: 10
agctctagac tgctgaggta cgtttcgg                                       28

```
<210> SEQ ID NO 11
<211> LENGTH: 23
<212> TYPE: DNA
<213> ORGANISM: Leptospira meyeri

<400> SEQUENCE: 11
catatgccta cctccgaaca gaa                                              23

<210> SEQ ID NO 12
<211> LENGTH: 26
<212> TYPE: DNA
<213> ORGANISM: Leptospira meyeri

<400> SEQUENCE: 12
aagctttcaa aggaaaactc cttcgt                                           26

<210> SEQ ID NO 13
<211> LENGTH: 33
<212> TYPE: DNA
<213> ORGANISM: Escherichia coli

<400> SEQUENCE: 13
gagatatacc atggtgacgc gtaaacaggc cac                                   33

<210> SEQ ID NO 14
<211> LENGTH: 30
<212> TYPE: DNA
<213> ORGANISM: Escherichia coli

<400> SEQUENCE: 14
ccgcaagctt tttaccccctt gtttgcagcc                                      30

<210> SEQ ID NO 15
<211> LENGTH: 30
<212> TYPE: DNA
<213> ORGANISM: Pseudomonas aeruginosa

<400> SEQUENCE: 15
ggaattccat atgactcagg actgggatgc                                       30

<210> SEQ ID NO 16
<211> LENGTH: 27
<212> TYPE: DNA
<213> ORGANISM: Pseudomonas aeruginosa

<400> SEQUENCE: 16
ccttaattaa tcacagcgcg gccagcc                                          27

<210> SEQ ID NO 17
<211> LENGTH: 30
<212> TYPE: DNA
<213> ORGANISM: Pseudomonas putida

<400> SEQUENCE: 17
ggaattccat atgacggatc aatgggatgc                                       30

<210> SEQ ID NO 18
<211> LENGTH: 27
<212> TYPE: DNA
<213> ORGANISM: Pseudomonas putida

<400> SEQUENCE: 18
ccttaattaa tcacaatgcc gccagcc                                          27
```

<210> SEQ ID NO 19
<211> LENGTH: 29
<212> TYPE: DNA
<213> ORGANISM: Pseudomonas aeruginosa

<400> SEQUENCE: 19
ggaattccat atgaagctgg aaacgcttg                                29

<210> SEQ ID NO 20
<211> LENGTH: 28
<212> TYPE: DNA
<213> ORGANISM: Pseudomonas aeruginosa

<400> SEQUENCE: 20
ccttaattaa tcagccgcgg ctggcctc                                 28

<210> SEQ ID NO 21
<211> LENGTH: 29
<212> TYPE: DNA
<213> ORGANISM: Corynebacterium glutamicum

<400> SEQUENCE: 21
cgcaggccat ggtgtctttt gacccaaac                                29

<210> SEQ ID NO 22
<211> LENGTH: 27
<212> TYPE: DNA
<213> ORGANISM: Corynebacterium glutamicum

<400> SEQUENCE: 22
ccgccgaagc ttctaaaggt tattgag                                  27

<210> SEQ ID NO 23
<211> LENGTH: 30
<212> TYPE: DNA
<213> ORGANISM: Corynebacterium glutamicum

<400> SEQUENCE: 23
agtcgtcata tgccaaagta cgacaattcc                               30

<210> SEQ ID NO 24
<211> LENGTH: 31
<212> TYPE: DNA
<213> ORGANISM: Corynebacterium glutamicum

<400> SEQUENCE: 24
ctggcaccta ggctagattg cagcaaagcc g                             31

<210> SEQ ID NO 25
<211> LENGTH: 28
<212> TYPE: DNA
<213> ORGANISM: Leptospira meyeri

<400> SEQUENCE: 25
agtcgtcata tggtaggacc atcggggg                                 28

<210> SEQ ID NO 26
<211> LENGTH: 38
<212> TYPE: DNA
<213> ORGANISM: Leptospira meyeri

<400> SEQUENCE: 26

```
ctggcaccta ggttatcaga tattttttaa tgcctctt                                    38

<210> SEQ ID NO 27
<211> LENGTH: 28
<212> TYPE: DNA
<213> ORGANISM: Saccharomyces cerevisiae

<400> SEQUENCE: 27
ggaattccat atgccatctc atttcgat                                               28

<210> SEQ ID NO 28
<211> LENGTH: 28
<212> TYPE: DNA
<213> ORGANISM: Saccharomyces cerevisiae

<400> SEQUENCE: 28
ccttaattaa tcatggtttt tggccagc                                               28

<210> SEQ ID NO 29
<211> LENGTH: 21
<212> TYPE: DNA
<213> ORGANISM: Chromobacterium violaceum

<400> SEQUENCE: 29
catatggcat ccgacgcgcc g                                                      21

<210> SEQ ID NO 30
<211> LENGTH: 24
<212> TYPE: DNA
<213> ORGANISM: Chromobacterium violaceum

<400> SEQUENCE: 30
cctaggttag tcaaggcccc gcaa                                                   24

<210> SEQ ID NO 31
<211> LENGTH: 24
<212> TYPE: DNA
<213> ORGANISM: Nocardia farcinica

<400> SEQUENCE: 31
catatggtga tcaccggcgg cgcg                                                   24

<210> SEQ ID NO 32
<211> LENGTH: 24
<212> TYPE: DNA
<213> ORGANISM: Nocardia farcinica

<400> SEQUENCE: 32
cctaggtcag ctcagcgcgt gctc                                                   24

<210> SEQ ID NO 33
<211> LENGTH: 24
<212> TYPE: DNA
<213> ORGANISM: Bradyrhizobium japonicum

<400> SEQUENCE: 33
catatggtgg atatatccag gccg                                                   24

<210> SEQ ID NO 34
<211> LENGTH: 24
<212> TYPE: DNA
<213> ORGANISM: Bradyrhizobium japonicum

<400> SEQUENCE: 34
```

```
cctaggtcac gccttctcca gcgc                                           24

<210> SEQ ID NO 35
<211> LENGTH: 25
<212> TYPE: DNA
<213> ORGANISM: Hyphomonas neptunium

<400> SEQUENCE: 35
ggatccgatg gcggatgcac ccggc                                          25

<210> SEQ ID NO 36
<211> LENGTH: 24
<212> TYPE: DNA
<213> ORGANISM: Hyphomonas neptunium

<400> SEQUENCE: 36
aagctttcac aagctgttaa gcga                                           24

<210> SEQ ID NO 37
<211> LENGTH: 21
<212> TYPE: DNA
<213> ORGANISM: Methylococcus capsulatus

<400> SEQUENCE: 37
catatggaga cccgggccgt g                                              21

<210> SEQ ID NO 38
<211> LENGTH: 23
<212> TYPE: DNA
<213> ORGANISM: Methylococcus capsulatus

<400> SEQUENCE: 38
cctaggtcag gcgaagcgag cca                                            23

<210> SEQ ID NO 39
<211> LENGTH: 25
<212> TYPE: DNA
<213> ORGANISM: Methylobacillus flagellatus

<400> SEQUENCE: 39
catatgagtc agcatgaatg gcatg                                          25

<210> SEQ ID NO 40
<211> LENGTH: 25
<212> TYPE: DNA
<213> ORGANISM: Methylobacillus flagellatus

<400> SEQUENCE: 40
cctaggagtc agcatgaatg gcatg                                          25

<210> SEQ ID NO 41
<211> LENGTH: 22
<212> TYPE: DNA
<213> ORGANISM: Nitrosomonas europaea

<400> SEQUENCE: 41
catatgacga acgatctgga tc                                             22

<210> SEQ ID NO 42
<211> LENGTH: 25
<212> TYPE: DNA
<213> ORGANISM: Nitrosomonas europaea
```

```
<400> SEQUENCE: 42
cctaggttat tgcaatccgc gagca                                          25

<210> SEQ ID NO 43
<211> LENGTH: 23
<212> TYPE: DNA
<213> ORGANISM: Klesiella pneumoniae

<400> SEQUENCE: 43
catatgacgc gtaaacaggc cac                                            23

<210> SEQ ID NO 44
<211> LENGTH: 25
<212> TYPE: DNA
<213> ORGANISM: Klesiella pneumoniae

<400> SEQUENCE: 44
cctaggttat tcctcgtttg ctgcc                                          25

<210> SEQ ID NO 45
<211> LENGTH: 23
<212> TYPE: DNA
<213> ORGANISM: Bacillus subtilis

<400> SEQUENCE: 45
catatgtcac agcacgttga aac                                            23

<210> SEQ ID NO 46
<211> LENGTH: 27
<212> TYPE: DNA
<213> ORGANISM: Bacillus subtilis

<400> SEQUENCE: 46
cctaggttac tcaaatgaaa cagctcc                                        27

<210> SEQ ID NO 47
<211> LENGTH: 24
<212> TYPE: DNA
<213> ORGANISM: Shigella flexneri
<220> FEATURE:
<223> OTHER INFORMATION: Shigella flexneri 2457T

<400> SEQUENCE: 47
catatgacgc gtaaacaggc cacc                                           24

<210> SEQ ID NO 48
<211> LENGTH: 27
<212> TYPE: DNA
<213> ORGANISM: Shigella flexneri
<220> FEATURE:
<223> OTHER INFORMATION: Shigella flexneri 2457T

<400> SEQUENCE: 48
cctaggttac cccttgtttg cagcccg                                        27

<210> SEQ ID NO 49
<211> LENGTH: 33
<212> TYPE: DNA
<213> ORGANISM: Colwellia psychrerythraea

<400> SEQUENCE: 49
catatgtcga ttactaaaaa aggtaatatt acc                                 33
```

-continued

```
<210> SEQ ID NO 50
<211> LENGTH: 30
<212> TYPE: DNA
<213> ORGANISM: Colwellia psychrerythraea

<400> SEQUENCE: 50
cctaggttac agttggctct gcgttaaacc                                  30

<210> SEQ ID NO 51
<211> LENGTH: 23
<212> TYPE: DNA
<213> ORGANISM: Salmonella enterica
<220> FEATURE:
<223> OTHER INFORMATION: Salmonella enterica serovar Paratyphi A

<400> SEQUENCE: 51
catatgacgc gtaaacaggc cac                                         23

<210> SEQ ID NO 52
<211> LENGTH: 27
<212> TYPE: DNA
<213> ORGANISM: Salmonella enterica
<220> FEATURE:
<223> OTHER INFORMATION: Salmonella enterica serovar Paratyphi A

<400> SEQUENCE: 52
cctaggttac cccttgtttg cagcccg                                     27

<210> SEQ ID NO 53
<211> LENGTH: 403
<212> TYPE: PRT
<213> ORGANISM: Pseudomonas aeruginosa

<400> SEQUENCE: 53
```

Met Thr Gln Asp Trp Asp Ala Gly Arg Leu Asp Ser Asp Leu Glu Gly
1               5                   10                  15

Ala Ala Phe Asp Thr Leu Ala Val Arg Ala Gly Gln Arg Arg Thr Pro
            20                  25                  30

Glu Gly Glu His Gly Glu Ala Leu Phe Thr Thr Ser Ser Tyr Val Phe
        35                  40                  45

Arg Thr Ala Ala Asp Ala Ala Ala Arg Phe Ala Gly Glu Val Pro Gly
    50                  55                  60

Asn Val Tyr Ser Arg Tyr Thr Asn Pro Thr Val Arg Thr Phe Glu Glu
65                  70                  75                  80

Arg Ile Ala Ala Leu Glu Gly Ala Glu Gln Ala Val Ala Thr Ala Ser
                85                  90                  95

Gly Met Ser Ala Ile Leu Ala Leu Val Met Ser Leu Cys Ser Ser Gly
            100                 105                 110

Asp His Val Leu Val Ser Arg Ser Val Phe Gly Ser Thr Ile Ser Leu
        115                 120                 125

Phe Asp Lys Tyr Phe Lys Arg Phe Gly Ile Gln Val Asp Tyr Pro Pro
    130                 135                 140

Leu Ser Asp Leu Ala Ala Trp Glu Ala Ala Cys Lys Pro Asn Thr Lys
145                 150                 155                 160

Leu Phe Phe Val Glu Ser Pro Ser Asn Pro Leu Ala Glu Leu Val Asp
                165                 170                 175

Ile Ala Ala Leu Ala Glu Ile Ala His Ala Lys Gly Ala Leu Leu Ala
            180                 185                 190

Val Asp Asn Cys Phe Cys Thr Pro Ala Leu Gln Gln Pro Leu Lys Leu
        195                 200                 205

Gly Ala Asp Val Val Ile His Ser Ala Thr Lys Tyr Ile Asp Gly Gln
            210                 215                 220

Gly Arg Gly Met Gly Gly Val Val Ala Gly Arg Gly Glu Gln Met Lys
225                 230                 235                 240

Glu Val Val Gly Phe Leu Arg Thr Ala Gly Pro Thr Leu Ser Pro Phe
                245                 250                 255

Asn Ala Trp Leu Phe Leu Lys Gly Leu Glu Thr Leu Arg Ile Arg Met
            260                 265                 270

Gln Ala His Ser Ala Ser Ala Leu Ala Leu Ala Glu Trp Leu Glu Arg
        275                 280                 285

Gln Pro Gly Ile Glu Arg Val Tyr Tyr Ala Gly Leu Gln Ser His Pro
290                 295                 300

Gln His Glu Leu Ala Arg Arg Gln Gln Ser Gly Phe Gly Ala Val Val
305                 310                 315                 320

Ser Phe Asp Val Lys Gly Gly Arg Asp Ala Ala Trp Arg Phe Ile Asp
                325                 330                 335

Ala Thr Arg Met Val Ser Ile Thr Thr Asn Leu Gly Asp Thr Lys Thr
            340                 345                 350

Thr Ile Ala His Pro Ala Thr Thr Ser His Gly Arg Leu Ser Pro Glu
        355                 360                 365

Asp Arg Ala Arg Ala Gly Ile Gly Asp Ser Leu Ile Arg Val Ala Val
370                 375                 380

Gly Leu Glu Asp Leu Asp Asp Leu Lys Ala Asp Met Ala Arg Gly Leu
385                 390                 395                 400

Ala Ala Leu

<210> SEQ ID NO 54
<211> LENGTH: 403
<212> TYPE: PRT
<213> ORGANISM: Pseudomonas putida

<400> SEQUENCE: 54

Met Thr Asp Gln Trp Asp Ala Gly Arg Leu Asp Ser Asp Leu Glu Gly
1               5                   10                  15

Val Gly Phe Asp Thr Leu Ala Val Arg Ala Gly Gln His Arg Thr Pro
                20                  25                  30

Glu Gly Glu His Ser Glu Ala Leu Phe Leu Thr Ser Ser Tyr Val Phe
            35                  40                  45

Arg Thr Ala Ala Asp Ala Ala Arg Phe Ala Gly Glu Thr Pro Gly
        50                  55                  60

Asn Val Tyr Ser Arg Tyr Thr Asn Pro Ser Val Arg Ala Phe Glu Glu
65                  70                  75                  80

Arg Leu Ala Ala Met Glu Gly Ala Glu Gln Ala Val Gly Thr Ser Thr
                85                  90                  95

Gly Met Ala Ala Ile Leu Ala Val Met Ser Leu Cys Ser Ala Gly
            100                 105                 110

Asp His Val Leu Val Ser Gln Ser Val Phe Gly Ser Thr Ile Ser Leu
        115                 120                 125

Phe Glu Lys Tyr Phe Lys Arg Phe Gly Val Gln Val Asp Tyr Val Pro
130                 135                 140

Leu Val Asp Leu Ala Gly Trp Glu Lys Ala Ile Lys Ala Asn Thr Arg
145                 150                 155                 160

Leu Leu Ile Val Glu Ser Pro Ser Asn Pro Leu Ala Glu Leu Val Asp
                165                 170                 175

Ile Thr Ala Leu Ser Glu Ile Ala His Ala His Gly Ala Met Leu Val
            180                 185                 190

Val Asp Asn Cys Phe Ser Thr Pro Ala Leu Gln Gln Pro Leu Lys Leu
            195                 200                 205

Gly Ala Asp Ile Val Phe His Ser Ala Thr Lys Phe Ile Asp Gly Gln
        210                 215                 220

Gly Arg Cys Met Gly Gly Val Ala Gly Arg Ala Glu Gln Met Lys
225                 230                 235                 240

Glu Val Val Gly Phe Leu Arg Thr Ala Gly Pro Thr Leu Ser Pro Phe
                245                 250                 255

Asn Ala Trp Ile Phe Thr Lys Gly Leu Glu Thr Leu Arg Leu Arg Met
            260                 265                 270

Arg Ala His Cys Glu Ser Ala Gln Ala Leu Ala Glu Trp Leu Glu Gln
            275                 280                 285

Gln Asp Gly Val Glu Lys Val His Tyr Ala Gly Leu Pro Ser His Pro
        290                 295                 300

Gln His Ala Leu Ala Lys Arg Gln Met Ser Gly Phe Gly Ala Val Val
305                 310                 315                 320

Ser Phe Glu Val Lys Gly Gly Lys Glu Gly Ala Trp Arg Phe Ile Asp
                325                 330                 335

Ala Thr Arg Val Ile Ser Ile Thr Thr Asn Leu Gly Asp Ser Lys Thr
            340                 345                 350

Thr Ile Ala His Pro Ala Thr Thr Ser His Gly Arg Leu Ser Pro Gln
        355                 360                 365

Glu Arg Glu Ala Ala Gly Ile Arg Asp Ser Leu Ile Arg Val Ala Val
370                 375                 380

Gly Leu Glu Asp Val Ala Asp Leu Gln Ala Asp Leu Ala Arg Gly Leu
385                 390                 395                 400

Ala Ala Leu

<210> SEQ ID NO 55
<211> LENGTH: 425
<212> TYPE: PRT
<213> ORGANISM: Pseudomonas putida

<400> SEQUENCE: 55

Met Lys Leu Glu Thr Leu Ala Ile His Ala Gly Phe Ser Pro Asp Pro
1               5                   10                  15

Thr Thr Lys Ala Val Ala Val Pro Ile Tyr Gln Thr Thr Ser Phe Ala
            20                  25                  30

Phe Asp Asp Thr Gln His Gly Ala Asp Leu Phe Asp Leu Lys Val Ala
        35                  40                  45

Gly Asn Ile Tyr Ser Arg Ile Met Asn Pro Thr Asn Asp Val Leu Glu
    50                  55                  60

Gln Arg Met Ala Ala Leu Glu Gly Gly Val Gly Ala Leu Ala Val Ala
65                  70                  75                  80

Ser Gly Met Ala Ala Ile Thr Tyr Ala Ile Gln Thr Val Ala Glu Ala
                85                  90                  95

Gly Asp Asn Ile Val Ser Val Ala Lys Leu Tyr Gly Gly Thr Tyr Asn
            100                 105                 110

Leu Leu Ala His Thr Leu Pro Arg Met Gly Ile His Thr Arg Phe Ala
        115                 120                 125

Ala His Asp Asp Ile Ala Ala Leu Glu Ala Leu Ile Asp Ala Arg Thr
    130                 135                 140

```
Lys Ala Val Phe Cys Glu Ser Ile Gly Asn Pro Ala Gly Asn Ile Val
145                 150                 155                 160

Asp Ile Ala Ala Leu Ala Glu Ala Ala His Arg His Gly Val Pro Leu
                165                 170                 175

Ile Val Asp Asn Thr Val Ala Thr Pro Val Leu Cys Arg Pro Phe Glu
            180                 185                 190

His Gly Ala Asp Ile Val Val His Ser Leu Thr Lys Tyr Ile Gly Gly
        195                 200                 205

His Gly Thr Ser Ile Gly Gly Ile Val Ile Asp Ser Gly Lys Phe Pro
    210                 215                 220

Trp Ala Glu Asn Lys Glu Arg Phe Ala Leu Leu Asn Thr Pro Asp Pro
225                 230                 235                 240

Ser Tyr His Gly Val Thr Tyr Thr Glu Ala Phe Gly Pro Ala Ala Phe
                245                 250                 255

Ile Gly Arg Cys Arg Val Val Pro Leu Arg Asn Thr Gly Ala Ala Leu
            260                 265                 270

Ser Pro Phe Asn Ala Phe Leu Ile Leu Gln Gly Leu Glu Thr Leu Ala
        275                 280                 285

Leu Arg Met Glu Arg His Thr Glu Asn Ala Leu Lys Val Ala His Tyr
290                 295                 300

Leu Gln Ala His Glu Gln Val Ala Trp Val Lys Phe Ala Gly Leu Pro
305                 310                 315                 320

Asp His Pro Glu His Ala Leu Ala Gln Arg Tyr Thr Gly Gly Lys Pro
                325                 330                 335

Ala Ser Ile Leu Ser Phe Gly Ile Lys Gly Gly Gln Ala Ala Gly Ala
            340                 345                 350

Arg Phe Ile Asp Ala Leu Gln Leu Val Val Arg Leu Val Asn Ile Gly
        355                 360                 365

Asp Ala Lys Ser Leu Ala Cys His Pro Ala Ser Thr Thr His Arg Gln
    370                 375                 380

Leu Asn Asp Asp Glu Leu Glu Lys Ala Gly Val Pro Arg Asp Met Val
385                 390                 395                 400

Arg Leu Ser Ile Gly Ile Glu His Ser Asp Asp Ile Ile Ala Asp Leu
                405                 410                 415

Ala Gln Ala Leu Glu Ala Ser Arg Gly
            420                 425

<210> SEQ ID NO 56
<211> LENGTH: 394
<212> TYPE: PRT
<213> ORGANISM: Chromobacterium violaceum

<400> SEQUENCE: 56

Met Ala Ser Asp Ala Pro His Leu Pro Leu His Pro Glu Thr Leu Ala
1               5                   10                  15

Ile Arg Ala Gly Leu Glu Thr Ser Gln Phe Asn Glu His Ser Gln Gly
            20                  25                  30

Leu Phe Leu Thr Ser Ser Phe Thr Tyr Glu Ser Ala Ala Gln Ala Ala
        35                  40                  45

Ala Met Phe Leu Gly Glu Ile Asp Gly Tyr Thr Tyr Ser Arg Phe Thr
    50                  55                  60

Asn Pro Thr Val Ala Ala Phe Gln His Arg Leu Ala Gln Met Glu Gly
65                  70                  75                  80

Gly Glu Arg Ala Ile Ala Thr Ala Thr Gly Met Ala Ala Ile Gln Ala
```

```
            85                  90                  95
Ile Met Met Thr Leu Leu Gln Ala Gly Asp His Ile Val Ser Ser Gln
            100                 105                 110

Ser Leu Phe Gly Ser Thr Thr Asn Leu Phe Ala Asn Gln Leu Ala Lys
            115                 120                 125

Phe Ala Val Ala Thr Asp Phe Val Asp Ala Arg Asp Leu Ser Ala Trp
            130                 135                 140

Arg Glu Ala Leu Arg Pro Asn Thr Lys Leu Leu Phe Leu Glu Thr Pro
145                 150                 155                 160

Ser Asn Pro Leu Thr Glu Val Ala Asp Ile Ala Ala Ile Ala Asp Ile
            165                 170                 175

Ala His Ala His Gly Ala Leu Leu Val Val Asp Asn Ser Phe Cys Ser
            180                 185                 190

Pro Ala Leu Gln Gln Pro Leu Lys Leu Gly Ala Asp Leu Val Met His
            195                 200                 205

Ser Ala Thr Lys Phe Ile Asp Gly His Gly Arg Val Met Gly Gly Ala
            210                 215                 220

Val Val Gly Ser Asp Lys Leu Val Glu Gln Val Tyr Leu His Val Arg
225                 230                 235                 240

Ala Ala Gly Pro Ser Leu Ala Pro Phe Asn Ala Trp Thr Leu Leu Ser
            245                 250                 255

Gly Leu Glu Thr Leu His Leu Arg Met Glu Lys His Ser Ala Asn Ala
            260                 265                 270

Leu Glu Leu Ala Arg Trp Leu Glu Ala Gln Pro Asn Val Glu Arg Val
            275                 280                 285

Tyr Tyr Pro Gly Leu Glu Ser His Pro Gln His Glu Leu Ala Leu Arg
            290                 295                 300

Gln Gln Lys Ser Gly Gly Ala Val Val Ser Phe Val Lys Gly Gly
305                 310                 315                 320

Arg Lys Ala Ala Trp Lys Val Val Asp Ala Val Arg Val Ile Ser Arg
            325                 330                 335

Thr Ala Asn Leu Gly Asp Val Lys Thr Thr Leu Thr His Pro Ala Ser
            340                 345                 350

Thr Thr His Ala Arg Val Thr Gln Glu Ala Arg Glu Arg Ala Gly Ile
            355                 360                 365

Val Glu Gly Leu Leu Arg Val Ser Val Gly Leu Glu Asn Val Arg Asp
            370                 375                 380

Leu Gln Gln Asp Leu Leu Arg Gly Leu Asp
385                 390

<210> SEQ ID NO 57
<211> LENGTH: 404
<212> TYPE: PRT
<213> ORGANISM: Nocardia farcinica

<400> SEQUENCE: 57

Val Ile Thr Gly Gly Ala Phe Asp Lys Pro Leu Pro Glu Gly Val Gly
1               5                   10                  15

Pro Ala Thr Leu Gly Val Arg Gly Gly Leu Arg Arg Ser Gly Phe Glu
            20                  25                  30

Glu Thr Ala Glu Ala Leu Tyr Leu Thr Ser Gly Phe Val Tyr Glu Ser
            35                  40                  45

Ala Glu Ala Ala Glu Ala Phe Thr Gly Glu Val Glu His Phe Val
            50                  55                  60
```

Tyr Ser Arg Tyr Gly Asn Pro Thr Val Ala Met Phe Glu Glu Arg Ile
 65                  70                  75                  80

Arg Leu Met Asp Gly Ala Glu Ala Ala Phe Ala Thr Ala Ser Gly Met
                 85                  90                  95

Ser Ala Val Phe Thr Ala Leu Gly Ala Leu Gly Ala Gly Asp Arg
                100                 105                 110

Leu Val Ala Ala Arg Ser Leu Phe Gly Ser Cys Phe Val Cys Asn
                115                 120                 125

Glu Ile Leu Pro Arg Trp Gly Val Glu Thr Val Phe Val Asp Gly Glu
                130                 135                 140

Asp Leu Asp Gln Trp Glu Arg Ala Leu Ser Val Pro Thr Ala Ala Val
145                 150                 155                 160

Phe Phe Glu Thr Pro Ala Asn Pro Met Gln Thr Leu Val Asp Val Arg
                165                 170                 175

Arg Val Thr Glu Leu Ala His Ala Ala Gly Ala Lys Val Val Leu Asp
                180                 185                 190

Asn Val Phe Ala Thr Pro Leu Leu Gln Lys Gly Phe Asp Leu Gly Ala
                195                 200                 205

Asp Val Val Val Tyr Ser Gly Thr Lys His Ile Asp Gly Gln Gly Arg
210                 215                 220

Val Leu Gly Gly Ala Ile Leu Gly Asp Arg Glu Tyr Ile Asp Gly Pro
225                 230                 235                 240

Val Lys Thr Leu Met Arg His Thr Gly Pro Ala Leu Ser Pro Phe Asn
                245                 250                 255

Ala Trp Thr Leu Leu Lys Gly Leu Glu Thr Met Pro Leu Arg Val Arg
                260                 265                 270

His Ser Thr Glu Ser Ala Leu Arg Ile Ala Arg Phe Leu Glu Ser Asn
                275                 280                 285

Pro Ala Val Ser Trp Val Lys Tyr Pro Phe Leu Glu Ser His Pro Gln
                290                 295                 300

Tyr Asp Leu Ala Arg Ala Gln Met Ser Gly Gly Thr Val Val Thr
305                 310                 315                 320

Phe Glu Leu Lys Ala Ala Glu Gly Glu Ala Lys Lys Arg Ala Phe Glu
                325                 330                 335

Val Leu Asp Arg Leu Arg Ile Ile Asp Ile Ser Asn Asn Leu Gly Asp
                340                 345                 350

Ala Lys Thr Leu Ile Thr His Pro Ala Thr Thr His Arg Ala Met
                355                 360                 365

Gly Pro Glu Gly Arg Ala Gly Ile Gly Leu Thr Asp Gly Val Val Arg
                370                 375                 380

Ile Ser Val Gly Leu Glu Asp Val Asp Asp Leu Leu Ser Asp Leu Glu
385                 390                 395                 400

His Ala Leu Ser

<210> SEQ ID NO 58
<211> LENGTH: 417
<212> TYPE: PRT
<213> ORGANISM: Bradyrhizobium japonicum

<400> SEQUENCE: 58

Val Asp Ile Ser Arg Pro Val Phe Phe Val Thr Val Phe Asp Glu Thr
1                5                  10                  15

Val Met Ser Glu Val Pro Met Ser Lys Ser Pro Ala Thr Tyr Arg Pro
                20                  25                  30

```
Glu Thr Arg Leu Val His Ser Gly Thr Leu Arg Ser Gln Phe Gly Glu
             35                  40                  45

Thr Ser Glu Ala Leu Phe Leu Thr Gln Gly Tyr Val Tyr Asn Ser Ala
 50                  55                  60

Glu Cys Glu Ala Arg Phe Lys Gly Glu Asp Pro Gly Phe Ile Tyr
 65                  70                  75                  80

Ser Arg Tyr Ser Asn Pro Thr Ile Ser Met Phe Glu Arg Arg Met Ile
                 85                  90                  95

Glu Leu Glu Gly Ala Glu Ala Ala Arg Ser Ala Ala Thr Gly Met Ala
                100                 105                 110

Ala Val Thr Thr Ala Ile Leu Ala Pro Leu Lys Thr Gly Asp His Val
             115                 120                 125

Val Ala Ser Arg Ala Leu Phe Gly Ser Cys Leu Tyr Val Ile Gln Asp
130                 135                 140

Leu Leu Pro Arg Tyr Gly Ile Glu Thr Thr Leu Val Asp Gly Leu Asp
145                 150                 155                 160

Leu Asp Gln Trp Gln Arg Ala Leu Arg Pro Asn Thr Lys Thr Phe Phe
                165                 170                 175

Leu Glu Ser Pro Thr Asn Pro Thr Leu Asp Val Leu Asp Ile Pro Gly
            180                 185                 190

Ile Ala Glu Ile Ala His Lys Gly Gly Ala Arg Leu Val Val Asp Asn
        195                 200                 205

Val Phe Ala Thr Pro Ile Trp Gln Ser Pro Leu Ala Leu Gly Ala Asp
210                 215                 220

Val Val Val Tyr Ser Ala Thr Lys His Ile Asp Gly Gln Gly Arg Cys
225                 230                 235                 240

Leu Gly Gly Ile Ile Leu Ser Ser Glu Ala Phe Val Ala Glu His Leu
                245                 250                 255

His Asn Phe Met Arg Gln Thr Gly Pro Ser Ile Ser Pro Phe Asn Ala
            260                 265                 270

Trp Val Leu Leu Lys Gly Leu Glu Thr Leu Ala Val Arg Val Arg Ala
        275                 280                 285

Gln Thr Asp Thr Ala Ala Ser Val Ala Glu Val Leu Ala Gly His Pro
290                 295                 300

Lys Ile Ser Arg Leu Ile Tyr Pro Gly Arg Ala Asp His Pro Gln Ala
305                 310                 315                 320

Ala Leu Val Lys Lys Gln Met Arg Gly Gly Ser Thr Leu Val Gly Phe
                325                 330                 335

Glu Val Lys Gly Gly Lys Ala Ala Ala Phe Arg Val Leu Asn Glu Leu
            340                 345                 350

Lys Leu Ala Lys Ile Ser Asn Asn Leu Gly Asp Ala Lys Ser Leu Val
        355                 360                 365

Thr His Pro Ala Thr Thr Thr His Gln Arg Leu Lys Pro Glu Asp Arg
370                 375                 380

Ala Ala Leu Gly Ile Ser Glu Gly Phe Ile Arg Phe Ser Ala Gly Leu
385                 390                 395                 400

Glu His Ala Asp Asp Leu Ile Glu Asp Leu Thr Ala Ala Leu Glu Lys
                405                 410                 415

Ala

<210> SEQ ID NO 59
<211> LENGTH: 399
<212> TYPE: PRT
<213> ORGANISM: Hyphomonas neptunium
```

<400> SEQUENCE: 59

```
Met Ala Asp Ala Pro Gly Gly Asp Lys Lys Gly Trp Lys Pro Ala Thr
1               5                   10                  15

Gln Ala Val Arg Gly Gly Leu Met Arg Ser Gln His Gly Glu Ile Ser
            20                  25                  30

Glu Ala Leu Tyr Leu Thr Ser Gly Tyr Ala Tyr Asp Ser Ala Glu Gln
        35                  40                  45

Ala Met Arg Arg Met Ala Gly Glu Glu Gly Phe Val Tyr Ser Arg
    50                  55                  60

Tyr Gly Ser Pro Thr Asn Glu Met Leu Gln Gln Arg Leu Ala Leu Ile
65                  70                  75                  80

Glu Gly Ala Glu Ala Cys Arg Val Thr Gly Ser Gly Met Gly Ala Ile
                85                  90                  95

Ser Ser Ala Ile Leu Ala Pro Leu Lys Ala Gly Asp Arg Val Val Ala
            100                 105                 110

Ala Thr Ala Leu Phe Gly Ser Cys Arg Trp Ile Ile Ala Asn Gln Met
        115                 120                 125

Pro Lys Phe Gly Ile Glu Ala Val Phe Val Asp Gly Ala Asp Leu Asp
    130                 135                 140

Ala Trp Lys Arg Glu Ile Asp Lys Gly Cys Gln Leu Val Leu Ile Glu
145                 150                 155                 160

Ser Pro Ala Asn Pro Leu Leu Asp Gly Val Asp Ile Glu Ala Val Ala
                165                 170                 175

Arg Leu Ala Lys Ala Ala Gly Ala Leu Leu Val Val Asp Asn Val Phe
            180                 185                 190

Ala Thr Pro Val Leu Gln Arg Pro Leu Glu Met Gly Ala Asp Val Ile
        195                 200                 205

Ala Tyr Ser Ala Thr Lys His Met Asp Gly Gln Gly Arg Val Leu Leu
    210                 215                 220

Gly Ala Ile Leu Thr Asp Ala Lys Arg Met Ser Asp Val Tyr Asp Pro
225                 230                 235                 240

Trp Leu Arg His Met Gly Pro Ala Ala Ser Pro Phe Asn Ala Trp Val
                245                 250                 255

Val Leu Lys Gly Leu Glu Thr Met Gln Leu Arg Val Glu Ala Gln Ser
            260                 265                 270

Arg Thr Ala Ala Arg Leu Ala Asp Val Leu Ala Asp His Pro Ala Val
        275                 280                 285

Asn Ala Val Arg Tyr Pro His Arg Lys Asp His Pro His Tyr Glu Val
    290                 295                 300

His Lys Arg Gln Met Lys Ser Gly Gly Thr Leu Leu Ala Leu Ser Leu
305                 310                 315                 320

Lys Gly Gly Gln Asp Ala Ala Phe Arg Phe Leu Asn Gly Leu Gln Leu
                325                 330                 335

Val Asp Ile Cys Asn Asn Leu Gly Asp Thr Lys Ser Leu Ala Cys His
            340                 345                 350

Pro Ser Thr Thr Thr His Arg Ala Leu Ser Asp Glu Asp Gln Ala Ala
        355                 360                 365

Met Gly Leu Asp Arg Ser Trp Val Arg Leu Ser Val Gly Leu Glu Asp
    370                 375                 380

Ala Asp Asp Leu Glu Ala Asp Leu Leu Ala Ser Leu Asn Ser Leu
385                 390                 395
```

<210> SEQ ID NO 60
<211> LENGTH: 383
<212> TYPE: PRT
<213> ORGANISM: Methylococcus capsulatus

<400> SEQUENCE: 60

| Met | Glu | Thr | Arg | Ala | Val | Arg | Ala | Gly | Gln | Arg | Arg | Thr | Met | Glu | Gln |
|---|---|---|---|---|---|---|---|---|---|---|---|---|---|---|---|
| 1 | | | | 5 | | | | | 10 | | | | | 15 | |

| Glu | His | Ala | Glu | Pro | Ile | Phe | Ala | Thr | Ser | Ser | Tyr | Val | Phe | Ala | Ser |
| | | | 20 | | | | | 25 | | | | | 30 | | |

| Ala | Ala | Glu | Ala | Ala | Glu | Arg | Phe | Ala | Gly | Lys | Ala | Ala | Gly | Asn | Ile |
| | | | 35 | | | | | 40 | | | | | 45 | | |

| Tyr | Ser | Arg | Phe | Thr | Asn | Pro | Thr | Val | Arg | Thr | Phe | Glu | Glu | Arg | Leu |
| | 50 | | | | | 55 | | | | | 60 | | | | |

| Ala | Ala | Leu | Glu | Gly | Gly | Glu | Arg | Cys | Val | Ala | Val | Gly | Ser | Gly | Met |
| 65 | | | | | 70 | | | | | 75 | | | | | 80 |

| Ala | Ala | Ile | Ala | Ser | Thr | Ala | Phe | Gly | Leu | Leu | Lys | Ala | Gly | Asp | His |
| | | | | 85 | | | | | 90 | | | | | 95 | |

| Val | Val | Cys | Ser | Arg | Ser | Val | Phe | Gly | Asn | Thr | Thr | Leu | Leu | Phe | Gln |
| | | | 100 | | | | | 105 | | | | | 110 | | |

| Asn | Tyr | Leu | Ala | Lys | Phe | Gly | Val | Pro | Thr | Thr | Phe | Val | Gly | Leu | Thr |
| | | | 115 | | | | | 120 | | | | | 125 | | |

| Asp | Tyr | Asp | Gly | Trp | Ala | Ala | Ala | Ile | Arg | Pro | Glu | Thr | Arg | Phe | Leu |
| | 130 | | | | | 135 | | | | | 140 | | | | |

| Phe | Ile | Glu | Thr | Pro | Ser | Asn | Pro | Leu | Thr | Glu | Ile | Ala | Asp | Ile | Pro |
| 145 | | | | | 150 | | | | | 155 | | | | | 160 |

| Arg | Leu | Ala | Glu | Ile | Ala | His | Ser | Arg | Gly | Cys | Leu | Leu | Val | Val | Asp |
| | | | | 165 | | | | | 170 | | | | | 175 | |

| Asn | Cys | Phe | Cys | Thr | Pro | Ala | Leu | Gln | Arg | Pro | Leu | Ala | Leu | Gly | Ala |
| | | | 180 | | | | | 185 | | | | | 190 | | |

| Asp | Ile | Val | Ile | His | Ser | Ala | Thr | Lys | Tyr | Leu | Asp | Gly | Gln | Gly | Arg |
| | | | 195 | | | | | 200 | | | | | 205 | | |

| Cys | Val | Gly | Gly | Ala | Ile | Val | Gly | Gly | Arg | Glu | Leu | Leu | Asp | Ala | Glu |
| | 210 | | | | | 215 | | | | | 220 | | | | |

| Ile | Tyr | Pro | Phe | Leu | Arg | Thr | Gly | Gly | Pro | Ser | Met | Ser | Pro | Phe | Asn |
| 225 | | | | | 230 | | | | | 235 | | | | | 240 |

| Ala | Trp | Val | Phe | Leu | Lys | Gly | Leu | Glu | Thr | Leu | Asn | Leu | Arg | Met | Lys |
| | | | | 245 | | | | | 250 | | | | | 255 | |

| Ala | His | Cys | Glu | Asn | Ala | Leu | Gly | Leu | Ala | Arg | Trp | Leu | Glu | Ala | Gln |
| | | | 260 | | | | | 265 | | | | | 270 | | |

| Pro | Trp | Val | Glu | Arg | Val | His | Tyr | Pro | Gly | Leu | Ala | Ser | His | Pro | Gln |
| | | | 275 | | | | | 280 | | | | | 285 | | |

| His | Glu | Leu | Ala | Ala | Arg | Gln | Gln | Ser | Gly | Phe | Gly | Gly | Ile | Val | Ser |
| | 290 | | | | | 295 | | | | | 300 | | | | |

| Phe | Glu | Val | Lys | Gly | Gly | Gln | Glu | Ala | Ala | Trp | Arg | Leu | Ile | Asp | Ser |
| 305 | | | | | 310 | | | | | 315 | | | | | 320 |

| Thr | Arg | Leu | Leu | Ser | Ile | Thr | Gly | Asn | Leu | Gly | Asp | Ala | Lys | Thr | Thr |
| | | | | 325 | | | | | 330 | | | | | 335 | |

| Ile | Thr | His | Pro | Ala | Thr | Thr | Thr | His | Gly | Arg | Leu | Ser | Pro | Glu | Ala |
| | | | 340 | | | | | 345 | | | | | 350 | | |

| Arg | Ala | Ala | Ala | Gly | Ile | Ala | Asp | Gly | Leu | Ile | Arg | Ile | Ala | Val | Gly |
| | | | 355 | | | | | 360 | | | | | 365 | | |

| Leu | Glu | Asn | Leu | Ala | Asp | Ile | Gln | Ala | Asp | Leu | Ala | Arg | Phe | Ala | |
| | 370 | | | | | 375 | | | | | 380 | | | | |

<210> SEQ ID NO 61
<211> LENGTH: 392
<212> TYPE: PRT
<213> ORGANISM: Methylobacillus flagellatus

<400> SEQUENCE: 61

Met Ser Gln His Glu Trp His Ala Glu Thr Leu Gly Val Arg Ala Gly
1               5                   10                  15

Ser Glu His Thr Pro Phe Gly Glu Asn Ser Glu Ala Met Phe Leu Thr
            20                  25                  30

Ser Ser Phe Val Phe Glu Asn Ala Ala Gln Ala Ala Arg Phe Gly
        35                  40                  45

Gly Gln Glu Pro Gly Asn Ile Tyr Ser Arg Phe Thr Asn Pro Thr Val
    50                  55                  60

Ser Met Phe Gln Asn Lys Leu Ala Ala Leu Glu Gly Ala Glu Phe Cys
65                  70                  75                  80

Val Ala Thr Ser Ser Gly Met Ser Ala Ile Leu Ala Cys Val Met Gly
                85                  90                  95

Val Cys Ser Ala Gly Asp His Val Val Ala Ser Arg Ser Ile Phe Gly
            100                 105                 110

Thr Ser Val Gln Leu Phe Ser Asn Ile Leu Lys Arg Trp Gly Leu Glu
        115                 120                 125

Thr Thr Phe Val Gln Leu Ser Asp Pro Glu Ala Trp Thr Ala Ala Val
    130                 135                 140

Lys Pro Asn Thr Lys Leu Phe Phe Leu Glu Thr Pro Ser Asn Pro Leu
145                 150                 155                 160

Thr Glu Ile Cys Asp Ile Ala Val Val Ala Glu Ile Ala His Gln Ala
                165                 170                 175

Gly Ala Leu Leu Ala Val Asp Asn Cys Phe Cys Thr Pro Ala Leu Gln
            180                 185                 190

Lys Pro Leu Ala Leu Gly Ala Asp Ile Val Val His Ser Ala Thr Lys
        195                 200                 205

Tyr Ile Asp Gly Gln Gly Arg Cys Leu Gly Gly Ala Val Leu Gly Arg
    210                 215                 220

Lys Asp Val Leu Glu Pro Val Tyr Gly Phe Leu Arg Thr Ala Gly Pro
225                 230                 235                 240

Thr Met Ser Ala Phe Asn Ala Trp Val Phe Leu Lys Gly Leu Glu Thr
                245                 250                 255

Leu His Leu Arg Met Glu Ala His Ala Arg Asn Ala Leu Ala Leu Ala
            260                 265                 270

Gln Trp Leu Glu Gln Gln Pro Arg Val Glu Arg Val Tyr Tyr Pro Gly
        275                 280                 285

Leu Pro Ser His Pro Gln Tyr Ala Leu Ala Gln Lys Gln Gln Lys Ser
    290                 295                 300

Gly Gly Ala Ile Val Ser Phe Asp Val Lys Gly Gly Gln Pro Ala Ala
305                 310                 315                 320

Trp His Leu Ile Asp Ala Thr Arg Met Leu Ser Ile Thr Ala Asn Leu
                325                 330                 335

Gly Asp Ala Lys Ser Thr Ile Thr His Pro Ala Thr Thr His Ser
            340                 345                 350

Arg Val Ser Ala Glu Ala Arg Ala Ala Gly Ile Gly Asp Gly Leu
        355                 360                 365

Val Arg Ile Ala Val Gly Leu Glu His Ile Asp Asp Ile Lys Ala Asp
    370                 375                 380

```
Leu Ala Trp Leu Gly His Gln Asp
385                 390
```

<210> SEQ ID NO 62
<211> LENGTH: 391
<212> TYPE: PRT
<213> ORGANISM: Nitrosomonas europaea

<400> SEQUENCE: 62

```
Met Thr Asn Asp Leu Asp Pro Glu Thr Leu Ala Ile His Thr Gly Val
1               5                   10                  15

His Arg Ser Gln Phe Asn Glu His Ser Glu Ser Leu Tyr Leu Thr Ser
            20                  25                  30

Ser Phe Val Phe Asp Ser Ala Ala Gln Ala Ala Arg Phe Ser Gly
        35                  40                  45

Gln Glu Pro Gly Asn Ile Tyr Ser Arg Phe Thr Asn Pro Thr Val Thr
    50                  55                  60

Ala Met Gln Glu Arg Leu Ala Val Leu Glu Gly Ala Glu Ala Cys Ile
65                  70                  75                  80

Ala Thr Ala Ser Gly Met Ser Ala Ile Leu Thr Cys Val Met Gly Leu
                85                  90                  95

Leu Ser Ala Gly Asp His Ile Val Ala Ser Arg Ser Leu Phe Gly Ser
            100                 105                 110

Thr Val Ser Leu Phe Asn Asn Ile Leu Ser Arg Phe Gly Ile Gln Thr
        115                 120                 125

Thr Phe Val Ser Ala Thr Asp Pro Ala Glu Trp Gln Ala Ala Val Arg
    130                 135                 140

Pro Asn Thr Arg Leu Phe Phe Leu Glu Thr Pro Ser Asn Pro Leu Thr
145                 150                 155                 160

Glu Ile Ser Asp Ile Ala Ala Leu Ala Glu Ile Ala Lys Arg Ala Gly
                165                 170                 175

Val Trp Leu Ala Val Asp Asn Cys Phe Cys Thr Pro Ile Ile Gln Gln
            180                 185                 190

Pro Leu Lys Leu Gly Ala Asp Leu Val Ile His Ser Ala Thr Lys Tyr
        195                 200                 205

Leu Asp Gly Gln Gly Arg Val Leu Gly Gly Ala Ile Leu Gly Lys Arg
    210                 215                 220

Asp Leu Leu Met Asp Ser Gly Ile Phe Ser Phe Leu Arg Thr Ala Gly
225                 230                 235                 240

Pro Ser Leu Ser Ala Phe Asn Ala Trp Ile Ile Leu Lys Gly Met Glu
                245                 250                 255

Thr Leu Ser Leu Arg Val Lys Ala His Ser Asp His Ala Leu Glu Val
            260                 265                 270

Ala Arg Trp Leu Glu Thr His Pro Arg Val Gly Arg Val Phe Tyr Pro
        275                 280                 285

Gly Leu Pro Ser His Pro Gln His Glu Leu Ala Met Arg Gln Gln Lys
    290                 295                 300

Thr Gly Gly Gly Ile Val Ser Phe Glu Val Lys Gly Gly Arg Glu Ala
305                 310                 315                 320

Ala Trp Arg Val Val Asp Ala Ala Arg Leu Met Ser Ile Thr Ala Asn
                325                 330                 335

Leu Gly Asp Thr Lys Ser Thr Leu Thr His Pro Ala Thr Thr His
            340                 345                 350

Gly Arg Ile Ser Gln Glu Ala Arg Glu Ala Ala Gly Ile Arg Asp Gly
```

```
                355                 360                 365
Leu Leu Arg Ile Ala Val Gly Leu Glu Ser Pro Asp Asp Leu Lys Ala
    370                 375                 380

Asp Leu Ala Arg Gly Leu Gln
385                 390

<210> SEQ ID NO 63
<211> LENGTH: 386
<212> TYPE: PRT
<213> ORGANISM: Klesiella pneumoniae

<400> SEQUENCE: 63

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
                20                  25                  30

Tyr Asn Phe Thr Gly Phe Asn Glu Pro Arg Ala His Asp Tyr Ser Arg
            35                  40                  45

Arg Gly Asn Pro Thr Arg Asp Val Val Gln Arg Ala Leu Ala Glu Leu
        50                  55                  60

Glu Gly Gly Ala Gly Ala Val Leu Thr Asn Thr Gly Met Ser Ala Ile
65                  70                  75                  80

Leu Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
                100                 105                 110

Lys Arg Gly Cys Tyr Arg Val Gln Phe Val Asp Gln Ser Asp Glu Gln
            115                 120                 125

Ala Leu Arg Ala Ala Leu Ala Glu Lys Pro Lys Leu Val Leu Val Glu
        130                 135                 140

Ser Pro Ser Asn Pro Leu Leu Arg Val Val Asp Ile Ala Lys Ile Cys
145                 150                 155                 160

Gly Leu Ala Arg Glu Ala Gly Ala Ile Ser Val Val Asp Asn Thr Phe
                165                 170                 175

Leu Ser Pro Ala Leu Gln Asn Pro Leu Ala Leu Gly Ala Asp Leu Val
                180                 185                 190

Leu His Ser Cys Thr Lys Tyr Leu Asn Gly His Ser Asp Val Val Ala
            195                 200                 205

Gly Val Val Ile Ala Lys Asp Pro Thr Thr Val Thr Glu Leu Ala Trp
        210                 215                 220

Trp Ala Asn Asn Ile Gly Val Thr Gly Ser Ala Phe Asp Ser Tyr Leu
225                 230                 235                 240

Leu Leu Arg Gly Leu Arg Thr Leu Ser Pro Arg Met Glu Val Ala Gln
                245                 250                 255

Arg Asn Ala Leu Ala Ile Val Glu Tyr Leu Lys Thr Gln Pro Leu Val
                260                 265                 270

Lys Lys Leu Tyr His Pro Ser Leu Pro Glu Asn Gln Gly His Glu Ile
            275                 280                 285

Ala Ala Arg Gln Gln Lys Gly Phe Gly Ala Met Leu Ser Phe Glu Leu
        290                 295                 300

Asp Gly Asp Glu Gln Thr Leu Arg Arg Phe Leu Ser Gly Leu Ser Leu
305                 310                 315                 320

Phe Thr Leu Ala Glu Ser Leu Gly Gly Val Glu Ser Leu Ile Ser His
                325                 330                 335
```

```
Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
370                 375                 380

Glu Glu
385

<210> SEQ ID NO 64
<211> LENGTH: 373
<212> TYPE: PRT
<213> ORGANISM: Bacillus subtilis

<400> SEQUENCE: 64

Met Ser Gln His Val Glu Thr Lys Leu Ala Gln Ile Gly Asn Arg Ser
1               5                   10                  15

Asp Glu Val Thr Gly Thr Val Ser Ala Pro Ile Tyr Leu Ser Thr Ala
            20                  25                  30

Tyr Arg His Arg Gly Ile Gly Glu Ser Thr Gly Phe Asp Tyr Val Arg
        35                  40                  45

Thr Lys Asn Pro Thr Arg Gln Leu Val Glu Asp Ala Ile Ala Asn Leu
    50                  55                  60

Glu Asn Gly Ala Arg Gly Leu Ala Phe Ser Ser Gly Met Ala Ala Ile
65                  70                  75                  80

Gln Thr Ile Met Ala Leu Phe Lys Ser Gly Asp Glu Leu Ile Val Ser
                85                  90                  95

Ser Asp Leu Tyr Gly Gly Thr Tyr Arg Leu Phe Glu Asn Glu Trp Lys
            100                 105                 110

Lys Tyr Gly Leu Thr Phe His Tyr Asp Asp Phe Ser Glu Asp Cys
        115                 120                 125

Leu Arg Ser Lys Ile Thr Pro Asn Thr Lys Ala Val Phe Val Glu Thr
    130                 135                 140

Pro Thr Asn Pro Leu Met Gln Glu Ala Asp Ile Glu His Ile Ala Arg
145                 150                 155                 160

Ile Thr Lys Glu His Gly Leu Leu Leu Ile Val Asp Asn Thr Phe Tyr
                165                 170                 175

Thr Pro Val Leu Gln Arg Pro Leu Glu Leu Gly Ala Asp Ile Val Ile
            180                 185                 190

His Ser Ala Thr Lys Tyr Leu Gly Gly His Asn Asp Leu Leu Ala Gly
        195                 200                 205

Leu Val Val Val Lys Asp Glu Arg Leu Gly Glu Glu Met Phe Gln His
    210                 215                 220

Gln Asn Ala Ile Gly Ala Val Leu Pro Pro Phe Asp Ser Trp Leu Leu
225                 230                 235                 240

Met Arg Gly Met Lys Thr Leu Ser Leu Arg Met Arg Gln His Gln Ala
                245                 250                 255

Asn Ala Gln Glu Leu Ala Ala Phe Leu Glu Glu Gln Glu Glu Ile Ser
            260                 265                 270

Asp Val Leu Tyr Pro Gly Lys Gly Gly Met Leu Ser Phe Arg Leu Gln
        275                 280                 285

Lys Glu Glu Trp Val Asn Pro Phe Leu Lys Ala Leu Lys Thr Ile Cys
    290                 295                 300

Phe Ala Glu Ser Leu Gly Gly Val Glu Ser Phe Ile Thr Tyr Pro Ala
305                 310                 315                 320
```

```
Thr Gln Thr His Met Asp Ile Pro Glu Glu Ile Arg Ile Ala Asn Gly
                325                 330                 335

Val Cys Asn Arg Leu Leu Arg Phe Ser Val Gly Ile Glu His Ala Glu
            340                 345                 350

Asp Leu Lys Glu Asp Leu Lys Gln Ala Leu Cys Gln Val Lys Glu Gly
        355                 360                 365

Ala Val Ser Phe Glu
    370
```

<210> SEQ ID NO 65
<211> LENGTH: 386
<212> TYPE: PRT
<213> ORGANISM: Shigella flexneri
<220> FEATURE:
<223> OTHER INFORMATION: Shigella flexneri 2457T

<400> SEQUENCE: 65

```
Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Asp Val Val Thr Glu Leu Ala Trp
    210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
    290                 295                 300
```

Asp Gly Asp Glu Gln Thr Leu Cys Arg Phe Leu Gly Leu Ser Leu
305                 310                 315                 320

Phe Thr Leu Ala Glu Ser Leu Gly Gly Val Glu Ser Leu Ile Ser His
            325                 330                 335

Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
370                 375                 380

Lys Gly
385

<210> SEQ ID NO 66
<211> LENGTH: 388
<212> TYPE: PRT
<213> ORGANISM: Colwellia psychrerythraea

<400> SEQUENCE: 66

Met Ser Ile Thr Lys Lys Gly Asn Ile Thr Thr Ser Ala Val Arg Ala
1               5                   10                  15

Gly Ile Asn Thr Asp Gln Gln His Gly Ala Val Val Ala Pro Ile Tyr
            20                  25                  30

Leu Ser Ser Thr Tyr Ser Leu Lys Gly Phe Asn Asn Lys Arg Gln Phe
        35                  40                  45

Asp Tyr Ser Arg Thr Gly Asn Pro Thr Arg Ala Thr Phe Ala Gly Ala
    50                  55                  60

Ile Ala Glu Leu Glu Gln Gly Ser Val Gly Ile Val Thr Ser Thr Gly
65              70                  75                  80

Met Ala Ala Val His Leu Ile Cys Gln Leu Leu Ser Thr Gln Asp Thr
                85                  90                  95

Val Val Ile Pro His Asp Cys Tyr Gly Gly Ser Phe Arg Leu Phe Thr
            100                 105                 110

His Leu Ala Lys Arg Gly Gln Phe Lys Leu Ile Val Val Asp Gln Asn
        115                 120                 125

Asp Gln Gln Ala Leu Asp Asn Ala Leu Ala His Lys Pro Lys Leu Val
    130                 135                 140

Leu Leu Glu Ser Pro Ser Asn Pro Leu Leu Arg Leu Val Asp Ile Glu
145                 150                 155                 160

Val Val Thr Lys Ala Cys His Ala Val Gly Ala Leu Val Ala Val Asp
                165                 170                 175

Asn Thr Phe Leu Ser Pro Ala Leu Gln Gln Pro Leu Thr Leu Gly Ala
            180                 185                 190

Asp Ile Val Phe His Ser Thr Thr Lys Tyr Ile Asn Gly His Ser Asp
        195                 200                 205

Val Val Gly Gly Val Val Ala Lys Thr Glu Glu Leu Gly Glu Gln
    210                 215                 220

Leu Ala Trp Trp Ala Asn Cys Ile Gly Ile Thr Gly Ser Ala Phe Asp
225                 230                 235                 240

Ser Phe Leu Ala Leu Arg Gly Leu Lys Thr Leu Pro Val Arg Met Lys
                245                 250                 255

Gln His Gln Glu Asn Ala Leu Arg Val Ala Asp Phe Leu Lys Asn His
            260                 265                 270

Asp Ala Ile Asp Ala Ile Tyr Phe Pro Gly Phe Pro Glu His Thr Gly

```
                275                 280                 285
His His Ile Ala Lys Lys Gln Gln Tyr Gly Phe Gly Ala Met Leu Ser
            290                 295                 300

Phe Glu Ile Lys Gly Asp Val Glu Ala Val Lys Lys Leu Phe Glu Asn
305                 310                 315                 320

Leu Glu Leu Phe Thr Leu Ala Gln Ser Leu Gly Gly Val Glu Ser Leu
                325                 330                 335

Ile Ser His Pro Ser Thr Met Thr His Ala Gly Met Thr Ile Pro Asp
            340                 345                 350

Gln Leu Glu Ala Gly Ile Thr Gln Ser Leu Val Arg Ile Ser Val Gly
                355                 360                 365

Ile Glu Asp Ile Asp Asp Ile Leu Ala Asp Leu Ala His Gly Leu Thr
            370                 375                 380

Gln Ser Gln Leu
385

<210> SEQ ID NO 67
<211> LENGTH: 386
<212> TYPE: PRT
<213> ORGANISM: Salmonella enterica
<220> FEATURE:
<223> OTHER INFORMATION: Salmonella enterica serovar Paratyphi A

<400> SEQUENCE: 67

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
                20                  25                  30

Tyr Asn Phe Thr Gly Phe Asn Glu Pro Arg Ala His Asp Tyr Ser Arg
            35                  40                  45

Arg Gly Asn Pro Thr Arg Asp Val Val Gln Arg Ala Leu Ala Glu Leu
        50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Thr Arg Gly Cys Tyr Cys Val Arg Phe Val Asp Gln Gly Asp Glu Arg
        115                 120                 125

Ala Leu Gln Ala Ala Leu Glu Glu Lys Pro Lys Leu Val Leu Val Glu
130                 135                 140

Ser Pro Ser Asn Pro Leu Leu Arg Val Val Asp Ile Ala Lys Ile Cys
145                 150                 155                 160

Arg Leu Ala Arg Glu Ala Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Glu Val Val Thr Glu Leu Ala Trp
210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
```

```
                    245                 250                 255
Arg Asn Ala Gln Ala Ile Val Lys Tyr Leu Gln Thr Gln Pro Leu Val
                260                 265                 270

Lys Lys Leu Tyr His Pro Ser Leu Pro Glu Asn Gln Gly His Glu Ile
            275                 280                 285

Ala Ala Arg Gln Gln Lys Gly Phe Gly Ala Met Leu Ser Phe Glu Leu
        290                 295                 300

Asp Gly Asp Glu Glu Thr Leu Arg Arg Phe Leu Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ser Pro Gln Ala Arg Ala Ala
                340                 345                 350

Ala Gly Ile Ser Glu Thr Leu Leu Arg Ile Ser Thr Gly Ile Glu Asp
            355                 360                 365

Gly Glu Asp Leu Ile Ala Asp Leu Gly Asn Gly Phe Arg Ala Ala Asn
        370                 375                 380

Lys Gly
385

<210> SEQ ID NO 68
<211> LENGTH: 20
<212> TYPE: DNA
<213> ORGANISM: Corynebacterium glutamicum

<400> SEQUENCE: 68
catatgccca ccctcgcgcc                                              20

<210> SEQ ID NO 69
<211> LENGTH: 25
<212> TYPE: DNA
<213> ORGANISM: Corynebacterium glutamicum

<400> SEQUENCE: 69
aagcttttag atgtagaact cgatg                                        25

<210> SEQ ID NO 70
<211> LENGTH: 70
<212> TYPE: DNA
<213> ORGANISM: Escherichia coli

<400> SEQUENCE: 70
caatttcttg cgtgaagaaa acgtctttgt gatgacaact tctcgtgcgt gtgtaggctg    60
gagctgcttc                                                         70

<210> SEQ ID NO 71
<211> LENGTH: 70
<212> TYPE: DNA
<213> ORGANISM: Escherichia coli

<400> SEQUENCE: 71
aatccagcgt tggattcatg tgccgtagat cgtatggcgt gatctggtag catatgaata    60
tcctccttag                                                         70

<210> SEQ ID NO 72
<211> LENGTH: 6
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Ile, Thr or Val
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (6)..(6)
<223> OTHER INFORMATION: Asn or Ser

<400> SEQUENCE: 72

Tyr Xaa Arg Xaa Xaa Xaa
1               5

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Ala or Ile
<220> FEATURE:
<221> NAME/KEY: MOD_RES
<222> LOCATION: (2)..(2)
<223> OTHER INFORMATION: Val, Leu or Ile
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Phe, Val, Met or Ile
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Thr or Ser
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Leu or Ile
<220> FEATURE:
<221> NAME/KEY: MOD_RES
<222> LOCATION: (12)..(12)
<223> OTHER INFORMATION: Gln, Cys or Val
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Pro or Gly
<220> FEATURE:
<221> NAME/KEY: MOD_RES
<222> LOCATION: (15)..(15)
```

```
<223> OTHER INFORMATION: Leu or Phe
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Leu, Met or His
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Asp or His

<400> SEQUENCE: 73

Xaa Xaa Asp Asn Xaa Xaa Xaa Xaa Xaa Xaa Xaa Xaa Xaa Xaa Xaa
1               5                   10                  15

Xaa Gly Xaa Xaa
            20

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Ala, Gly or Pro
<220> FEATURE:
<221> NAME/KEY: MOD_RES
<222> LOCATION: (2)..(2)
<223> OTHER INFORMATION: Pro, Ala or Val
<220> FEATURE:
<221> NAME/KEY: MOD_RES
<222> LOCATION: (4)..(4)
<223> OTHER INFORMATION: Asn or Asp
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Trp, Phe or Tyr
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (10)..(10)
<223> OTHER INFORMATION: Lys, Gln, Arg or Ser
<220> FEATURE:
<221> NAME/KEY: MOD_RES
<222> LOCATION: (12)..(12)
<223> OTHER INFORMATION: Leu, Met, Val, Ile or Met
<220> FEATURE:
<221> NAME/KEY: MOD_RES
<222> LOCATION: (13)..(13)
<223> OTHER INFORMATION: Glu, Lys, Asp or Arg
<220> FEATURE:
<221> NAME/KEY: MOD_RES
<222> LOCATION: (15)..(15)
<223> OTHER INFORMATION: Leu or Met

<400> SEQUENCE: 74

Xaa Xaa Phe Xaa Xaa Xaa Xaa Xaa Xaa Xaa Gly Xaa Xaa Thr Xaa
1               5                   10                  15
```

```
<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His or Tyr
<220> FEATURE:
<221> NAME/KEY: MOD_RES
<222> LOCATION: (2)..(2)
<223> OTHER INFORMATION: Pro or Ala
<220> FEATURE:
<221> NAME/KEY: MOD_RES
<222> LOCATION: (3)..(3)
<223> OTHER INFORMATION: Ala or Ser
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Thr, Met or Gln
<220> FEATURE:
<221> NAME/KEY: MOD_RES
<222> LOCATION: (6)..(6)
<223> OTHER INFORMATION: Thr or Ser

<400> SEQUENCE: 75

Xaa Xaa Xaa Xaa Xaa Xaa His
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Ile or Leu
<220> FEATURE:
<221> NAME/KEY: MOD_RES
<222> LOCATION: (3)..(3)
<223> OTHER INFORMATION: Val, Ile, Leu or Phe
<220> FEATURE:
<221> NAME/KEY: MOD_RES
<222> LOCATION: (4)..(4)
<223> OTHER INFORMATION: Ser or Ala
<220> FEATURE:
<221> NAME/KEY: MOD_RES
<222> LOCATION: (5)..(5)
<223> OTHER INFORMATION: Val, Ile or Thr
<220> FEATURE:
<221> NAME/KEY: MOD_RES
<222> LOCATION: (7)..(7)
<223> OTHER INFORMATION: Leu or Ile

<400> SEQUENCE: 76

Xaa Arg Xaa Xaa Xaa Gly Xaa Glu
1               5

<210> SEQ ID NO 77
<211> LENGTH: 403
<212> TYPE: PRT
<213> ORGANISM: Pseudomonas aeruginosa
```

```
<400> SEQUENCE: 77

Met Thr Gln Asp Trp Asp Ala Gly Arg Leu Asp Ser Asp Leu Glu Gly
1               5                   10                  15

Ala Ala Phe Asp Thr Leu Ala Val Arg Ala Gly Gln Arg Arg Thr Pro
            20                  25                  30

Glu Gly Glu His Gly Glu Ala Leu Phe Thr Thr Ser Ser Tyr Val Phe
        35                  40                  45

Arg Thr Ala Ala Asp Ala Ala Arg Phe Ala Gly Glu Val Pro Gly
    50                  55                  60

Asn Val Tyr Ser Arg Tyr Thr Asn Pro Thr Val Arg Thr Phe Glu Glu
65                  70                  75                  80

Arg Ile Ala Ala Leu Glu Gly Ala Glu Gln Ala Val Ala Thr Ala Ser
                85                  90                  95

Gly Met Ser Ala Ile Leu Ala Leu Val Met Ser Leu Cys Ser Ser Gly
            100                 105                 110

Asp His Val Leu Val Ser Arg Ser Val Phe Gly Ser Thr Ile Ser Leu
        115                 120                 125

Phe Asp Lys Tyr Phe Lys Arg Phe Gly Ile Gln Val Asp Tyr Pro Pro
130                 135                 140

Leu Ser Asp Leu Ala Ala Trp Glu Ala Ala Cys Lys Pro Asn Thr Lys
145                 150                 155                 160

Leu Phe Phe Val Glu Ser Pro Ser Asn Pro Leu Ala Glu Leu Val Asp
                165                 170                 175

Ile Ala Ala Leu Ala Glu Ile Ala His Ala Lys Gly Ala Leu Leu Ala
            180                 185                 190

Val Asp Asn Cys Phe Cys Thr Pro Ala Leu Gln Gln Pro Leu Lys Leu
        195                 200                 205

Gly Ala Asp Val Val Ile His Ser Ala Thr Lys Tyr Ile Asp Gly Gln
210                 215                 220

Gly Arg Gly Met Gly Gly Val Val Ala Gly Arg Gly Glu Gln Met Lys
225                 230                 235                 240

Glu Val Val Gly Phe Leu Arg Thr Ala Gly Pro Thr Leu Ser Pro Phe
                245                 250                 255

Asn Ala Trp Leu Phe Leu Lys Gly Leu Glu Thr Leu Arg Ile Arg Met
            260                 265                 270

Gln Ala His Ser Ala Ser Ala Leu Ala Leu Ala Glu Trp Leu Glu Arg
        275                 280                 285

Gln Pro Gly Ile Glu Arg Val Tyr Tyr Ala Gly Leu Pro Ser His Pro
290                 295                 300

Gln His Glu Leu Ala Arg Arg Gln Gln Ser Gly Phe Gly Ala Val Val
305                 310                 315                 320

Ser Phe Asp Val Lys Gly Gly Arg Asp Ala Ala Trp Arg Phe Ile Asp
                325                 330                 335

Ala Thr Arg Met Val Ser Ile Thr Thr Asn Leu Gly Asp Thr Lys Thr
            340                 345                 350

Thr Ile Ala His Pro Ala Thr Thr Ser His Gly Arg Leu Ser Pro Glu
        355                 360                 365

Asp Arg Ala Arg Ala Gly Ile Gly Asp Ser Leu Ile Arg Val Ala Val
370                 375                 380

Gly Leu Glu Asp Leu Asp Asp Leu Lys Ala Asp Met Ala Arg Gly Leu
385                 390                 395                 400

Ala Ala Leu
```

```
<210> SEQ ID NO 78
<211> LENGTH: 406
<212> TYPE: PRT
<213> ORGANISM: Mycobacterium tuberculosis

<400> SEQUENCE: 78

Met Thr Asp Glu Ser Ser Val Arg Thr Pro Lys Ala Leu Pro Asp Gly
1               5                   10                  15

Val Ser Gln Ala Thr Val Gly Val Arg Gly Gly Met Leu Arg Ser Gly
            20                  25                  30

Phe Glu Glu Thr Ala Glu Ala Met Tyr Leu Thr Ser Gly Tyr Val Tyr
        35                  40                  45

Gly Ser Ala Ala Val Ala Glu Lys Ser Phe Ala Gly Glu Leu Asp His
    50                  55                  60

Tyr Val Tyr Ser Arg Tyr Gly Asn Pro Thr Val Ser Val Phe Glu Glu
65                  70                  75                  80

Arg Leu Arg Leu Ile Glu Gly Ala Pro Ala Ala Phe Ala Thr Ala Ser
                85                  90                  95

Gly Met Ala Ala Val Phe Thr Ser Leu Gly Ala Leu Leu Gly Ala Gly
            100                 105                 110

Asp Arg Leu Val Ala Ala Arg Ser Leu Phe Gly Ser Cys Phe Val Val
        115                 120                 125

Cys Ser Glu Ile Leu Pro Arg Trp Gly Val Gln Thr Val Phe Val Asp
130                 135                 140

Gly Asp Asp Leu Ser Gln Trp Glu Arg Ala Leu Ser Val Pro Thr Gln
145                 150                 155                 160

Ala Val Phe Phe Glu Thr Pro Ser Asn Pro Met Gln Ser Leu Val Asp
                165                 170                 175

Ile Ala Ala Val Thr Glu Leu Ala His Ala Ala Gly Ala Lys Val Val
            180                 185                 190

Leu Asp Asn Val Phe Ala Thr Pro Leu Leu Gln Gln Gly Phe Pro Leu
        195                 200                 205

Gly Val Asp Val Val Tyr Ser Gly Thr Lys His Ile Asp Gly Gln
    210                 215                 220

Gly Arg Val Leu Gly Gly Ala Ile Leu Gly Asp Arg Glu Tyr Ile Asp
225                 230                 235                 240

Gly Pro Val Gln Lys Leu Met Arg His Thr Gly Pro Ala Met Ser Ala
                245                 250                 255

Phe Asn Ala Trp Val Leu Leu Lys Gly Leu Glu Thr Leu Ala Ile Arg
            260                 265                 270

Val Gln His Ser Asn Ala Ser Ala Gln Arg Ile Ala Glu Phe Leu Asn
        275                 280                 285

Gly His Pro Ser Val Arg Trp Val Arg Tyr Pro Tyr Leu Pro Ser His
    290                 295                 300

Pro Gln Tyr Asp Leu Ala Lys Arg Gln Met Ser Gly Gly Thr Val
305                 310                 315                 320

Val Thr Phe Ala Leu Asp Cys Pro Glu Asp Val Ala Lys Gln Arg Ala
                325                 330                 335

Phe Glu Val Leu Asp Lys Met Arg Leu Ile Asp Ile Ser Asn Asn Leu
            340                 345                 350

Gly Asp Ala Lys Ser Leu Val Thr His Pro Ala Thr Thr His Arg
        355                 360                 365

Ala Met Gly Pro Glu Gly Arg Ala Ala Ile Gly Leu Gly Asp Gly Val
    370                 375                 380
```

```
Val Arg Ile Ser Val Gly Leu Glu Asp Thr Asp Leu Ile Ala Asp
385                 390                 395                 400

Ile Asp Arg Ala Leu Ser
                405
```

<210> SEQ ID NO 79
<211> LENGTH: 403
<212> TYPE: PRT
<213> ORGANISM: Pseudomonas putida

<400> SEQUENCE: 79

```
Met Thr Asp Gln Trp Asp Ala Gly Arg Leu Asp Ser Asp Leu Glu Gly
1               5                   10                  15

Val Gly Phe Asp Thr Leu Ala Val Arg Ala Gly Gln Asn Arg Thr Pro
                20                  25                  30

Glu Gly Glu His Ser Glu Ala Leu Phe Leu Thr Ser Ser Tyr Val Phe
            35                  40                  45

Arg Thr Ala Ala Asp Ala Ala Arg Phe Ala Gly Glu Thr Pro Gly
        50                  55                  60

Asn Val Tyr Ser Arg Tyr Thr Asn Pro Ser Val Arg Ala Phe Glu Glu
65                  70                  75                  80

Arg Leu Ala Ala Met Glu Gly Ala Glu Gln Ala Val Gly Thr Ser Thr
                85                  90                  95

Gly Met Ala Ala Ile Leu Ala Val Val Met Ser Leu Cys Ser Ala Gly
            100                 105                 110

Asp His Val Leu Val Ser Gln Ser Val Phe Gly Ser Thr Ile Ser Leu
        115                 120                 125

Phe Glu Lys Tyr Phe Lys Arg Phe Gly Val Glu Val Asp Tyr Val Pro
    130                 135                 140

Leu Val Asp Leu Thr Gly Trp Glu Lys Ala Ile Lys Ala Asn Thr Lys
145                 150                 155                 160

Leu Leu Ile Val Glu Ser Pro Ser Asn Pro Leu Ala Glu Leu Val Asp
                165                 170                 175

Ile Thr Ala Leu Ser Glu Ile Ala His Ala Gln Gly Ala Met Leu Val
            180                 185                 190

Val Asp Asn Cys Phe Ser Thr Pro Ala Leu Gln Gln Pro Leu Lys Leu
        195                 200                 205

Gly Ala Asp Ile Val Phe His Ser Ala Thr Lys Phe Ile Asp Gly Gln
    210                 215                 220

Gly Arg Cys Met Gly Gly Val Ala Gly Arg Thr Glu Gln Met Lys
225                 230                 235                 240

Glu Val Val Gly Phe Leu Arg Thr Ala Gly Pro Thr Leu Ser Pro Phe
                245                 250                 255

Asn Ala Trp Ile Phe Thr Lys Gly Leu Glu Thr Leu Arg Leu Arg Met
            260                 265                 270

Arg Ala His Cys Glu Ser Ala Gln Ala Leu Ala Glu Trp Leu Glu Gln
        275                 280                 285

Gln Asp Gly Val Glu Lys Val His Tyr Ala Gly Leu Pro Ser His Pro
    290                 295                 300

Gln His Glu Leu Ala Lys Arg Gln Met Ser Gly Phe Gly Ala Val Val
305                 310                 315                 320

Ser Phe Glu Val Lys Gly Gly Lys Glu Gly Ala Trp Arg Phe Ile Asp
                325                 330                 335

Ala Thr Arg Val Ile Ser Ile Thr Thr Asn Leu Gly Asp Ser Lys Thr
```

```
                    340                 345                 350
Thr Ile Ala His Pro Ala Thr Thr Ser His Gly Arg Leu Ser Pro Gln
            355                 360                 365

Glu Arg Glu Ala Ala Gly Ile Arg Asp Ser Leu Ile Arg Val Ala Val
        370                 375                 380

Gly Leu Glu Asp Val Ala Asp Leu Gln Ala Asp Leu Ala Arg Gly Leu
385                 390                 395                 400

Ala Ala Leu

<210> SEQ ID NO 80
<211> LENGTH: 442
<212> TYPE: PRT
<213> ORGANISM: Leptospira meyeri

<400> SEQUENCE: 80

Met Val Gly Pro Ser Gly Glu Ser Met Pro Arg Asn Phe Lys Pro Glu
1               5                   10                  15

Thr Ile Ala Leu His Gly Gly Gln Glu Pro Asp Pro Thr Thr Thr Ser
            20                  25                  30

Arg Ala Val Pro Leu Tyr Gln Thr Thr Ser Tyr Val Phe Lys Asp Thr
        35                  40                  45

Asp His Ala Ala Arg Leu Phe Gly Leu Gln Glu Phe Gly Asn Ile Tyr
    50                  55                  60

Thr Arg Leu Met Asn Pro Thr Thr Asp Val Leu Glu Lys Arg Val Ala
65                  70                  75                  80

Ala Leu Glu Gly Gly Val Ala Ala Leu Ala Thr Ala Ser Gly Gln Ser
                85                  90                  95

Ala Glu Met Leu Ala Leu Leu Asn Ile Val Glu Ala Gly Gln Glu Ile
            100                 105                 110

Val Ala Ser Ser Ser Leu Tyr Gly Gly Thr Tyr Asn Leu Leu His Tyr
        115                 120                 125

Thr Phe Pro Lys Leu Gly Ile Lys Val His Phe Val Asp Gln Ser Asp
    130                 135                 140

Pro Glu Asn Phe Arg Lys Ala Ser Asn Asp Lys Thr Arg Ala Phe Tyr
145                 150                 155                 160

Ala Glu Thr Leu Gly Asn Pro Lys Leu Asp Thr Leu Asp Ile Ala Ala
                165                 170                 175

Val Ser Lys Val Ala Lys Glu Val Gly Val Pro Leu Val Ile Asp Asn
            180                 185                 190

Thr Met Pro Ser Pro Tyr Leu Val Asn Pro Leu Lys His Gly Ala Asp
        195                 200                 205

Ile Val Val His Ser Leu Thr Lys Phe Leu Gly Gly His Gly Thr Ser
    210                 215                 220

Ile Gly Gly Ile Ile Ile Asp Gly Gly Ser Phe Asn Trp Gly Asn Gly
225                 230                 235                 240

Lys Phe Lys Asn Phe Thr Glu Pro Asp Pro Ser Tyr His Gly Leu Lys
                245                 250                 255

Phe Trp Glu Val Phe Gly Lys Phe Glu Pro Phe Gly Gly Val Asn Ile
            260                 265                 270

Ala Phe Ile Leu Lys Ala Arg Val Gln Gly Leu Arg Asp Leu Gly Pro
        275                 280                 285

Ala Ile Ser Pro Phe Asn Ala Trp Gln Ile Leu Gln Gly Val Glu Thr
    290                 295                 300

Leu Pro Leu Arg Met Glu Arg His Ser Gly Asn Ala Leu Lys Val Ala
```

```
            305                 310                 315                 320
Glu Phe Leu Gln Lys His Pro Lys Ile Glu Trp Val Asn Tyr Pro Gly
                325                 330                 335

Leu Ser Thr Asp Lys Asn Tyr Ala Thr Ala Lys Lys Tyr His Glu Arg
                340                 345                 350

Gly Leu Phe Gly Ala Ile Val Gly Phe Glu Ile Lys Gly Val Glu
                355                 360                 365

Lys Ala Lys Lys Phe Ile Asp Gly Leu Glu Leu Phe Ser Leu Leu Ala
370                 375                 380

Asn Ile Gly Asp Ala Lys Ser Leu Ala Ile His Pro Ala Ser Thr Thr
385                 390                 395                 400

His Gln Gln Leu Thr Gly Pro Glu Gln Ile Ser Ala Gly Val Thr Pro
                405                 410                 415

Gly Phe Val Arg Leu Ser Val Gly Leu Glu Asn Ile Asp Ile Leu
                420                 425                 430

Val Asp Leu Glu Glu Ala Leu Lys Asn Ile
                435                 440

<210> SEQ ID NO 81
<211> LENGTH: 386
<212> TYPE: PRT
<213> ORGANISM: Corynebacterium glutamicum

<400> SEQUENCE: 81

Met Ser Phe Asp Pro Asn Thr Gln Gly Phe Ser Thr Ala Ser Ile His
1               5                   10                  15

Ala Gly Tyr Glu Pro Asp Asp Tyr Tyr Gly Ser Ile Asn Thr Pro Ile
                20                  25                  30

Tyr Ala Ser Thr Thr Phe Ala Gln Asn Ala Pro Asn Glu Leu Arg Lys
            35                  40                  45

Gly Tyr Glu Tyr Thr Arg Val Gly Asn Pro Thr Ile Val Ala Leu Glu
        50                  55                  60

Gln Thr Val Ala Ala Leu Glu Gly Ala Lys Tyr Gly Arg Ala Phe Ser
65                  70                  75                  80

Ser Gly Met Ala Ala Thr Asp Ile Leu Phe Arg Ile Ile Leu Lys Pro
                85                  90                  95

Gly Asp His Ile Val Leu Gly Asn Asp Ala Tyr Gly Gly Thr Tyr Arg
                100                 105                 110

Leu Ile Asp Thr Val Phe Thr Ala Trp Gly Val Glu Tyr Thr Val Val
            115                 120                 125

Asp Thr Ser Val Val Glu Glu Val Lys Ala Ala Ile Lys Asp Asn Thr
        130                 135                 140

Lys Leu Ile Trp Val Glu Thr Pro Thr Asn Pro Ala Leu Gly Ile Thr
145                 150                 155                 160

Asp Ile Glu Ala Val Ala Lys Leu Thr Glu Gly Thr Asn Ala Lys Leu
                165                 170                 175

Val Val Asp Asn Thr Phe Ala Ser Pro Tyr Leu Gln Gln Pro Leu Lys
                180                 185                 190

Leu Gly Ala His Ala Val Leu His Ser Thr Thr Lys Tyr Ile Gly Gly
            195                 200                 205

His Ser Asp Val Val Gly Gly Leu Val Val Thr Asn Asp Gln Glu Met
        210                 215                 220

Asp Glu Glu Leu Leu Phe Met Gln Gly Gly Ile Gly Pro Ile Pro Ser
225                 230                 235                 240
```

```
Val Phe Asp Ala Tyr Leu Thr Ala Arg Gly Leu Lys Thr Leu Ala Val
            245                 250                 255

Arg Met Asp Arg His Cys Asp Asn Ala Glu Lys Ile Ala Glu Phe Leu
260                 265                 270

Asp Ser Arg Pro Glu Val Ser Thr Val Leu Tyr Pro Gly Leu Lys Asn
            275                 280                 285

His Pro Gly His Glu Val Ala Ala Lys Gln Met Lys Arg Phe Gly Gly
        290                 295                 300

Met Ile Ser Val Arg Phe Ala Gly Gly Glu Ala Ala Lys Lys Phe
305                 310                 315                 320

Cys Thr Ser Thr Lys Leu Ile Cys Leu Ala Glu Ser Leu Gly Gly Val
                325                 330                 335

Glu Ser Leu Leu Glu His Pro Ala Thr Met Thr His Gln Ser Ala Ala
            340                 345                 350

Gly Ser Gln Leu Glu Val Pro Arg Asp Leu Val Arg Ile Ser Ile Gly
        355                 360                 365

Ile Glu Asp Ile Glu Asp Leu Leu Ala Asp Val Glu Gln Ala Leu Asn
370                 375                 380

Asn Leu
385

<210> SEQ ID NO 82
<211> LENGTH: 437
<212> TYPE: PRT
<213> ORGANISM: Corynebacterium glutamicum

<400> SEQUENCE: 82

Met Pro Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
            20                  25                  30

Asn Leu Pro Ile Tyr Gln Ser Thr Ala Phe Val Phe Asp Ser Ala Glu
        35                  40                  45

His Ala Lys Gln Arg Phe Ala Leu Glu Asp Leu Gly Pro Val Tyr Ser
    50                  55                  60

Arg Leu Thr Asn Pro Thr Val Glu Ala Leu Glu Asn Arg Ile Ala Ser
65                  70                  75                  80

Leu Glu Gly Gly Val His Ala Val Ala Phe Ser Ser Gly Gln Ala Ala
                85                  90                  95

Thr Thr Asn Ala Ile Leu Asn Leu Ala Gly Ala Gly Asp His Ile Val
            100                 105                 110

Thr Ser Pro Arg Leu Tyr Gly Gly Thr Glu Thr Leu Phe Leu Ile Thr
        115                 120                 125

Leu Asn Arg Leu Gly Ile Asp Val Ser Phe Val Glu Asn Pro Asp Asp
    130                 135                 140

Pro Glu Ser Trp Gln Ala Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175

Val Ala Glu Val Ala His Arg Asn Ser Val Pro Leu Ile Ile Asp Asn
            180                 185                 190

Thr Ile Ala Thr Ala Ala Leu Val Arg Pro Leu Glu Leu Gly Ala Asp
        195                 200                 205

Val Val Val Ala Ser Leu Thr Lys Phe Tyr Thr Gly Asn Gly Ser Gly
    210                 215                 220
```

Leu Gly Gly Val Leu Ile Asp Gly Lys Phe Asp Trp Thr Val Glu
225                 230                 235                 240

Lys Asp Gly Lys Pro Val Phe Pro Tyr Phe Val Thr Pro Asp Ala Ala
            245                 250                 255

Tyr His Gly Leu Lys Tyr Ala Asp Leu Gly Ala Pro Ala Phe Gly Leu
            260                 265                 270

Lys Val Arg Val Gly Leu Leu Arg Asp Thr Gly Ser Thr Leu Ser Ala
            275                 280                 285

Phe Asn Ala Trp Ala Ala Val Gln Gly Ile Asp Thr Leu Ser Leu Arg
290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
            325                 330                 335

Pro Trp Tyr Ala Thr Lys Glu Lys Leu Gly Leu Lys Tyr Thr Gly Ser
            340                 345                 350

Val Leu Thr Phe Glu Ile Lys Gly Gly Lys Asp Glu Ala Trp Ala Phe
            355                 360                 365

Ile Asp Ala Leu Lys Leu His Ser Asn Leu Ala Asn Ile Gly Asp Val
370                 375                 380

Arg Ser Leu Val Val His Pro Ala Thr Thr His Ser Gln Ser Asp
385                 390                 395                 400

Glu Ala Gly Leu Ala Arg Ala Gly Val Thr Gln Ser Thr Val Arg Leu
            405                 410                 415

Ser Val Gly Ile Glu Thr Ile Asp Ile Ile Ala Asp Leu Glu Gly
            420                 425                 430

Gly Phe Ala Ala Ile
            435

<210> SEQ ID NO 83
<211> LENGTH: 386
<212> TYPE: PRT
<213> ORGANISM: Escherichia coli

<400> SEQUENCE: 83

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys

-continued

```
            145                 150                 155                 160
His Leu Ala Arg Glu Val Gly Ala Val Ser Val Val Asp Asn Thr Phe
                    165                 170                 175

Leu Ser Pro Ala Leu Gln Asn Pro Leu Ala Leu Gly Ala Asp Leu Val
                180                 185                 190

Leu His Ser Cys Thr Lys Tyr Leu Asn Gly His Ser Asp Val Val Ala
            195                 200                 205

Gly Val Val Ile Ala Lys Asp Pro Asp Val Val Thr Glu Leu Ala Trp
            210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
                260                 265                 270

Lys Lys Leu Tyr His Pro Ser Leu Pro Glu Asn Gln Gly His Glu Ile
                275                 280                 285

Ala Ala Arg Gln Gln Lys Gly Phe Gly Ala Met Leu Ser Phe Glu Leu
            290                 295                 300

Asp Gly Asp Glu Gln Thr Leu Arg Arg Phe Leu Gly Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
                340                 345                 350

Ala Gly Ile Ser Glu Thr Leu Leu Arg Ile Ser Thr Gly Ile Glu Asp
            355                 360                 365

Gly Glu Asp Leu Ile Ala Asp Leu Glu Asn Gly Phe Arg Ala Ala Asn
            370                 375                 380

Lys Gly
385
```

MICROORGANISM PRODUCING L-METHIONINE PRECURSOR AND METHOD OF PRODUCING L-METHIONINE AND ORGANIC ACID FROM THE L-METHIONINE PRECURSOR

RELATED APPLICATIONS

This application is a continuation application of U.S. application Ser. No. 12/066,111, filed Mar. 7, 2008, which is a 35 U.S.C. §371 national phase application of PCT/KR2007/003650 (WO 2008/013432), filed on Jul. 30, 2007, each entitled "Microorganism producing L-methionine precursor and method of producing L-methionine and organic acid from the L-methionine precursor," which application claims the benefit of Korean Application No. 10-2007-0076045, filed Jun. 27, 2007 and Korean Application No. 10-2006-0071581, filed Jul. 28, 2006, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 8, 2012, is named 011723.txt and is 90,987 bytes in size.

TECHNICAL FIELD

The present invention relates to a method for producing L-methionine and organic acid. More particularly, the present invention relates to a method for producing L-methionine and organic acid with high yield by enzyme conversion reaction from L-methionine precursor produced by the fermentation of L-methionine precursor-producing strain prepared according to the present invention. The method of the present invention to produce L-methionine is more pro-environmental than the conventional method and enables selective production of L-methionine so as to use L-methionine in various fields of industry as feed, food additives and a raw material for medical supplies and drugs, etc.

BACKGROUND ART

Methionine is one of essential amino acids of human body which has been widely used as feed and food additives and further used as a synthetic raw material for medical solutions and medical supplies. Methionine acts as a precursor of such compounds as choline (lecithin) and creatine and at the same time is used as a synthetic raw material for cysteine and taurine. Methionine can also provide sulfur. S-adenosyl-methionine is derived from L-methionine and plays a certain role in providing methyl group in human body and also is involved in the synthesis of various neurotransmitters in the brain. Methionine and/or S-adenosyl-L-methionine (SAM) inhibits fat accumulation in the liver and artery and alleviates depression, inflammation, liver disease, and muscle pain, etc.

The in vivo functions of methionine and/or S-adenosyl-L-methionine known so far are as follows.

1) It inhibits fat accumulation in the liver and artery promoting lipid metabolism and improves blood circulation in the brain, heart and kidney (J. Hepatol. Jeon B R et al., 2001 March; 34(3): 395-401).

2) It promotes digestion, detoxification and excretion of toxic substances and excretion of heavy metals such as Pb.

3) It can be administered as an anti-depression agent at the dosage of 800-1,600 mg/day (Am J Clin Nutr. Mischoulon D. et al., 2002 November; 76(5): 1158S-61S).

4) It enhances liver functions (FASEB J. Mato J M., 2002 January; 16(1): 15-26) and particularly is effective in the liver disease caused by alcohol (Cochrane Database Syst Rev., Rambaldi A., 2001; (4): CD002235).

5) It has anti-inflammatory effect on bone and joint diseases and promotes joint-recovery (ACP J. Club. Sander O., 2003 January-February; 138(1): 21, J Fam Pract., Soeken K L et al., 2002 May; 51(5): 425-30).

6) It is an essential nutrient for hair. It provides nutrition to hair and thereby prevents hair loss (Audiol Neurootol., Lockwood D S et al., 2000 September-October; 5(5): 263-266).

Methionine can be chemically or biologically synthesized to be applied to feed, food and medicines.

In the chemical synthesis, methionine is mostly produced by hydrolysis of 5-(β-methylmercaptoethyl)-hydantoin. The chemically synthesized methionine has a disadvantage of only being produced as a mixed form of L-type and D-type.

In the biological synthesis, methionine is produced by method using proteins involved in methionine synthesis. L-methionine is biosynthesized from homoserine by the action of the enzyme expressed by such genes as metA, metB, metC, metE and metH. Particularly, metA is the gene encoding homoserine O-succinyl transferase which is the first enzyme necessary for methionine biosynthesis, and it converts homoserine into O-succinyl-L-homoserine. O-succinylhomoserine lyase or cystathionine gamma synthase coded by metB gene converts O-succinyl-L-homoserine into cystathionine. Cystathionine beta lyase coded by metC gene converts cystathionine into L-homocysteine. MetE encodes cobalamine-independent methionine synthase and metH encodes cobalamine-dependent methionine synthase, both of which convert L-homocysteine into L-methionine. At this time, 5,10-methylenetetrahydrofolate reductase coded by metF and serine hydroxymethyltransferase coded by glyA work together to synthesize N(5)-methyltetrahydrofolate providing methyl group necessary for L-methionine synthesis.

L-methionine is synthesized by a series of organic reactions by the above enzymes. The genetic modification on the above proteins or other proteins affecting the above proteins might result in the regulation of L-methionine synthesis. For example, Japanese Laid-Open Patent Publication No. 2000/139471 describes a method of producing L-methionine with the *Escherichia* sp. of which thrBC and metJ genes on the genome are deleted, metBL is over-expressed and metK is replaced by a leaky mutant. Also, US Patent Publication No. US2003/0092026 A1 describes a method using a metD (L-methionine synthesis inhibitor) knock-out microorganism which belongs to *Corynebacterium* sp. US Patent Publication No. US2002/0049305 describes a method to increase L-methionine production by increasing the expression of 5,10-methylenetetrahydrofolate reductase (metF).

US Patent No. US2005/0054060A1 describes the method of preparing L-methionine producing microorganism using cystathionine synthase (O-succinylhomoserine lyase) mutant. This cystathionine synthase mutant can produce homocysteine or methionine directly from $H_2S$ or $CH_3SH$ instead of cysteine. In this method, mutant cystathionine synthase is directly introduced into a cell and participated in the intracellular methionine biosynthesis procedure. In this method, cystathionine synthase reaction is not very efficient due to the use of intracellular methionine biosynthesis pathway. Also, the high toxicity of $H_2S$ or $CH_3SH$ to the cells reduces the effectiveness of this method. In our experiment, we also found that the that substrate specificity of cystathionine synthase to CH₃SH is very low compared to succinylhomoserine lyase derived from *Pseudomonas* or *Chromobacterium* sp.

According to the previous reports, cystathionine synthase tend to produce various products by reaction with various substrates. Cystathionine synthase mediates the interaction between homocysteine and O-succinyl homoserine to produce homolanthionine with high efficiency (J. Bacteriol (2006) vol 188: p 609-618). The cystathionine synthase in a cell can interact with various methionine precursors and can produce various byproducts with high efficiency. Therefore, overexpression of Cystathionine synthase can make lower the reaction efficiency due to the higher production of byproduct.

The methionine produced by the conventional biological method is L-type, which has advantages but the production amount is too small. This is because the methionine biosynthetic pathway has very tight feed-back regulation systems. Once methionine is synthesized to a certain level, the final product methionine inhibits the transcription of metA gene encoding the primary protein for initiation of methionine biosynthesis. Over-expression of metA gene itself cannot increase methionine production because the metA gene is suppressed by methionine in the transcription stage and then degraded by the intracellular proteases in the translation stage (Dvora Biran, Eyal Gur, Leora Gollan and Eliora Z. Ron: Control of methionine biosynthesis in *Escherichia coli* by proteolysis: Molecular Microbiology (2000) 37(6), 1436-1443). Therefore, many of previous patents were focused on how to free the metA gene from its feed-back regulation system (WO2005/108561, WO1403813).

When methionine is produced in biological system, produced methionine is converted to S-adenosylmethionine by S-adenosylmethionine synthase in the methionine degradation pathway. S-adenosylmethionine synthase cannot be deleted because S-adenosylmethionine is an essential substance in cells. According to the previous patents, the gene encoding S-adenosylmethionine synthase was mutated to have low activity to increase the methionine production (WO2005/108561).

DISCLOSURE OF THE INVENTION

The conventional methionine biosynthesis method uses cystathionine synthase metabolism pathway to produce methionine, so the enzyme reaction process is inefficient due to the sulfide toxicity and byproducts generation. In addition, feed-back regulation in methionine synthesis pathway inhibits mass-production of methionine.

It is an object of the present invention to provide an alternative method of producing L-methionine to overcome the above problems of the conventional method. The alternative method is composed of two-step process in which L-methionine precursor is produced by fermentation and L-methionine precursor is converted to L-methionine by enzymes.

It is another object of the present invention to provide a method for producing L-methionine selectively.

It is further an object of the present invention to provide a method for simultaneously producing organic acid as a byproduct without an additional process.

The present invention is described in detail hereinafter.

To achieve the object of the invention, the present invention provides a method for producing L-methionine comprising the steps of 1) preparing L-methionine precursor producing strain and producing L-methionine precursor by the fermentation of the strain, and 2) producing L-methionine and organic acid by the enzyme reaction with the L-methionine precursor.

Particularly, in step 1) process, an L-methionine precursor producing strain is generated and fermented for the accumulation of L-methionine precursor in the culture media. At this time, the strain for the production of L-methionine precursor is prepared by the method of the invention designed by the inventors, so this invention also includes the strain and the method for generating the strain in its scope.

The L-methionine precursor herein is represented by one of the O-acyl homoserine group composed of the following formula;

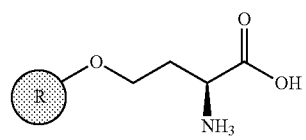

[Formula 1]

Wherein

R is a substance including C, H, O, N and other compounds with 15 carbon molecules at maximum. For example, the O-acyl homoserine group includes, but not limited to, O-acetyl homoserine, O-succinyl homoserine, propionyl homoserine, acetoacetyl homoserine, coumaroyl homoserine, malonyl homoserine, hydroxymethylglutaryl homoserine and pimelylhomoserine.

The L-methionine precursor of the present invention is preferably O-acetyl homoserine or O-succinyl homoserine.

The "L-methionine precursor-producing strain" as used herein refers to a prokaryotic or eukaryotic microorganism strain that is able to accumulate L-methionine precursor by the manipulation according to the present invention. For example, the strain can be selected from the group consisting of *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hyphomonas* sp., *Chromobacterium* sp. and *Nocardia* sp. microorganisms or fungi or yeasts. Preferably, the microorganisms of *Pseudomonas* sp., *Nocardia* sp. and *Escherichia* sp. can be used to produce O-succinylhomoserine, and the microorganisms of *Escherichia* sp., *Corynebacterium* sp., *Leptospira* sp. and yeasts can be used to produce O-acetylhomoserine. More preferably, the microorganisms of *Escherichia* sp. can be used, and most preferably *Escherichia coli* (hereinafter referred to as "*E. Coli*") can be used. In addition, the foreign genes can be introduced into the *Escherichia* sp. microorganism to selectively produce O-succinyl homoserine and O-acetyl homoserine.

The present invention provides an L-methionine precursor-producing strain in which the genes involved in the degradation of O-succinyl homoserine or O-acetyl homoserine is deleted or weakened. The present invention also provides an L-methionine precursor-producing strain in which the genes involved in the synthesis of O-succinyl homoserine or O-acetyl homoserine is introduced or enhanced. The present invention also selectively provides a strain in which threonine biosynthesis pathway is blocked or weakened to enhance O-succinyl homoserine or O-acetyl homoserine production. The present invention further provides a strain in which the genes which are free from feedback regulation system and encoding the proteins involved in the synthesis of O-succinyl homoserine or O-acetyl homoserine are introduced, overexpressed or activity-enhanced.

More particularly, the present invention provides an L-methionine precursor producing strain by deleting metB gene involved in the degradation of L-methionine precursor, thrB gene involved in threonine biosynthesis pathway and metJ gene repressing the transcription of L-methionine precursor synthesis gene and by enhancing the expression of the metA or metX gene involved in L-methionine precursor biosynthesis or introducing the metA or metX gene free from feed-back regulation system; or knocking-out metA gene and instead introducing metX gene; or deleting metX gene and instead introducing metA gene.

In the present invention, a deletion of the gene can be performed by cutting out of a region of the gene or modifying the protein sequence by introducing a specific DNA sequence on the chromosome. The weakening of the gene can be performed by reducing the protein activity by introducing the mutation in the ORF region of the target gene or by reducing the protein expression by the modification of a promoter region or of 5'-UTR nucleotide sequence of the gene.

In the present invention, the enhancement of the protein expression can be performed by the modification of the promoter region of the gene or the nucleotide sequence of the 5'-UTR region, and the enhancement of the activity of the protein can be performed by introducing the mutation in the ORF region of the target gene, and enhancement of the protein expression can also be performed by the introduction of the extra copy of target gene on the chromosome end or by the introduction of the vector harboring the target gene with the self-promoter or enhanced other promoter in the strain.

In a preferred embodiment of the present invention, the method for preparing an L-methionine precursor producing strain is as follows;

In step 1, a gene encoding such proteins as cystathionine gamma synthase, O-succinylhomoserine sulfhydrylase or O-acetylhomoserine sulfhydrylase is deleted or weakened in a strain in order to accumulate L-methionine precursor such as O-succinyl homoserine or O-acetyl homoserine.

The gene encoding cystathionine gamma synthase is indicated as metB, the gene encoding O-succinylhomoserine sulfhydrylase is indicated as metZ, and the gene encoding O-acetylhomoserine sulfhydrylase is indicated as metY. A gene encoding the protein having the above mentioned activity is exemplified by metB which was known for *E. Coli*. The genomic sequence of the gene can be obtained from the genomic sequence of *E. coli* (Accession no. AAC75876) informed in the previous report (Blattner et. al., Science 277: 1453-1462 (1997)). The above genomic sequence also can be obtained from NCBI (National Center for Biotechnology Information) and DDBJ (DNA Data Bank Japan). Other genes having the above activity are exemplified by metB and metY derived from *Corynebacterium*, and metZ derived from *Pseudomonas*.

Cystathionine gamma synthase or O-succinylhomoserine sulfhydrylase or O-acetylhomoserine sulfhydrylase has the activity to convert O-succinyl homoserine or O-acetylhomoserine into cystathionine or homocysteine as shown in the following reaction formulas. Therefore, the strain in which the genes having these activities are deleted or weakened, showed the accumulation of O-succinylhomoserine or O-acetylhomoserine in the culture solution.

L-cysteine+O-succinyl-L-homoserine<=>succinate+cystathionine

L-cysteine+O-acetyl-L-homoserine<=>acetate+cystathionine

HS⁻+O-succinyl-L-homoserine<=>succinate+homocysteine

HS⁻+O-acetyl-L-homoserine<=>acetate+homocysteine

In step 2, thrB gene encoding homoserine kinase in the strain prepared in step 1 is deleted or weakened. The thrB gene is involved in the synthesis of O-phosphohomoserine from homoserine, which is then converted into threonine by thrC gene. The thrB gene is deleted or weakened to use all the produced homoserine for the synthesis of methionine precursor.

In step 3, the metJ gene, the is transcription regulator of metA gene, is deleted or weakened. The metA gene involved in the synthesis of methionine precursor is regulated by feedback regulation system of methionine and the metJ gene is a repressor involved in the transcription of metA gene. To overexpress the metA gene constitutively and activate the synthesis methionine precursor, the elimination of the metA gene transcription repressor is profitable. Therefore, the metJ gene is eliminated in *E. coli* and the metA gene expression is increased, which can lead (to) the mass-production of L-methionine precursor.

The above steps 2 and 3 can be modified according to a precursor producing strain and might not be necessary for the precursor producing strain. However, it can be more preferably executed to enhance the precursor production pathway in the microorganism of *Escherichia* sp.

In step 4, the expression of metA or metX gene encoding homoserine O-succinyl transferase or homoserine O-acetyl transferase which is the enzyme mediating the first stage of methionine biosynthesis pathway is enhanced to promote the methionine precursor synthesis. The metA gene is the general term for the gene encoding homoserine O-succinyl transferase, and the metX gene is the general term for the gene encoding homoserine O-acetyl transferase. To enhance the expression of metA or metX gene, an additional copy of gene can be introduced or 5'-UTR or a promoter can be modified or ORF of each gene can be mutated. The enhancement of expression of this gene results in the significant increase of the L-methionine precursor synthesis.

If methionine is considered to be necessary for the growth of a strain, metA or metX gene free from feed-back regulation can be introduced. In this case, L-methionine precursor can be synthesized regardless of methionine content in the medium and so the addition of methionine to the medium facilitates the synthesis of L-methionine precursor and the growth of the cells.

To increase O-acetylhomoserine production from the O-succinylhomoserine producing strain, metA gene encoding homoserine O-succinyl transferase existing in the chromosome can be deleted. Where the production of O-succinylhomoserine is inhibited by deletion of metA gene and O-acetylhomoserine is produced by additionally introducing metX gene, O-acetylhomoserine can be produced with higher yield compare with the case of introducing metX gene in the presence of the metA gene.

It is also possible to increase O-succinylhomoserine production in O-acetylhomoserine producing strain by deleting metX gene encoding homoserine O-acetyl transferase existing in the chromosome of the strain. Where the production of O-acetylhomoserine is inhibited by deletion of metX gene and O-succinylhomoserine is produced by additionally introducing metA gene, O-succinylhomoserine can be produced with higher yield.

O-succinylhomoserine or O-acetylhomoserine, L-methionine precursor, can be accumulated in a strain by taking advantage of a part or the entire process of the above step 1-step 4.

The L-methionine precursor producing strain can be prepared from the strain producing L-lysine, L-threonine or L-isoleucine. Preferably, it can be prepared by using the L-threonine producing strain. With this strain, homoserine synthesis is already higher and the production of methionine precursor can be resultantly increased. So, methionine precursor can be accumulated by deleting or weakening a gene involved in threonine biosynthesis pathway and then metA or metY or MetZ gene, using the L-threonine producing strain. It is more preferred to delete or weaken thrB gene first and then metB, metY or metZ to synthesize methionine precursor. In the meantime, the enhancement of metA or metX gene expression results in the increase of methionine precursor synthesis.

The "L-threonine-producing strain" of the invention refers to a prokaryotic or eukaryotic microorganism strain that is able to produce L-threonine in vivo. For example, the strain can be include L-threonine producing microorganism strains belongs to *Escherichia* sp., *Erwinia* sp., *Serratia* sp., *Providencia* sp., *Corynebacterium* sp. and *Brevibacterium* sp. Among these, *Escherichia* sp. microorganism is preferred and *Escherichia coli* is more preferred.

The L-threonine producing strain includes not only the microorganisms in nature but also their mutants which are exemplified by microorganisms that has a leaky requirement for isoleucine and is resistant to L-lysine analogues and α-aminobutyric acid; and is mutated by additionally introducing at least an extra copy of endogenous phosphoenol pyruvate carboxylase(ppc) gene; and is inactivated pckA gene involved in the conversion process of oxaloacetate (OAA) that is an intermediate of L-methionine synthesis into phosphoenol pyruvate(PEP); and is inactivated tyrR gene inhibiting the expression of tyrB gene involved in L-methionine biosynthesis; and is inactivated galR gene inhibiting the expression of galP gene involved in glucose transport. The L-lysine analogs herein may be one or more compounds selected from the group consisting of S-(2-aminoethyl)-L-cysteine and δ-methyl-L-lysine.

In a preferred embodiment of the present invention, CJM002, the L-threonine producing and L-methionine-independent strain mutated from TF4076(KFCC 10718, Korean Patent No. 92-8365), the L-threonine producing *E. coli* mutant strain, was used. TF4076 has a requirement for methionine, and is resistant to methionine analogues (ex, α-amino-β-hydroxy valeric acid, AHV), lysine analogues (ex, S-(2-aminoethyl)-L-cysteine, AEC), and isoleucine analogues (ex, α-aminobutylic acid). The general information contained in the above Korean Patent can be included in the scope of the present invention by claims. The TF4076 is not able to synthesize methionine in vivo because it is the strain which has a requirement for methionine. To use this strain as the methionine producing strain of the invention by free from a requirement for methionine, the present inventors prepared the L-threonine producing strain *E. Coli* CJM002 free from the requirement for methionine by artificial mutation using NTG. The *E. coli* CJM002 was named as *Escherichia coli* MF001 and deposited at KCCM (Korean Culture Center of Microorganism, Eulim Buld., Hongje-1-Dong, Seodaemun-Ku, Seoul, 361-221, Korea) on Apr. 9, 2004 (Accession No: KCCM-10568). The O-succinylhomoserine producing *Escherichia coli* CJM-BTJ (pMetA-CL) prepared by the above method was also deposited on Jul. 21, 2006 (Accession No: KCCM-10767) and *Escherichia coli* CJM-BTJ (pCJ-MetA-CL) was deposited on Jul. 5, 2007 (Accession No: KCCM-10872). The O-acetylhomoserine producing *Escherichia coli* CJM-BTJA (pCJ-MetX-CL) prepared by the above method of the invention was also deposited on Jul. 5, 2007 (Accession No: KCCM-10873).

The culture of the L-methionine precursor producing strain prepared above can be performed by a proper medium and conditions known to those in the art. It is well understood by those in the art that the culture method can be used by easily adjusting, according to the selected strain. For example, he culture method including, but not limited to batch, continuous culture and fed-batch. A variety of culture methods are described in the following reference: "Biochemical Engineering" by James M. Lee, Prentice-Hall International Editions, pp 138-176.

The medium has to meet the culture conditions for a specific strain. A variety of microorganism culture mediums are described in the following reference: "Manual of Methods for General Bacteriology" by the American Society for Bacteriology, Washington D.C., USA, 1981. Those mediums include various carbon sources, nitrogen sources and trace elements. The carbon source is exemplified by carbohydrate such as glucose, sucrose, lactose, fructose, maltose, starch, cellulose; fat such as soybean oil, sunflower oil, castor oil and coconut oil; fatty acid such as palmitic acid, stearic acid, and linoleic acid; alcohol such as glycerol and ethanol; and organic acid such as acetic acid. One of these compounds or a mixture thereof can be used as a carbon source. The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source. The medium herein can additionally include potassium dihydrogen phosphate, dipotassium hydrogen phosphate and corresponding sodium-containing salts as a phosphate source. The medium also can include a metal salt such as magnesium sulfate or iron sulfate. In addition, amino acids, vitamins and proper precursors can be added as well. The mediums or the precursors can be added to the culture by batch-type or continuously.

pH of the culture can be adjusted during the cultivation by adding in the proper way such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas (ex, air) can be injected into the culture. The temperature of the culture is conventionally 20-45° C., preferably 25-40° C. The period of cultivation can be continued until the production of L-methionine precursor reaches a wanted level, and the preferable cultivation time is 10-160 hours.

Step 2) process includes the process for producing L-methionine and organic acid by enzyme reaction using an enzyme having the activity of cystathionine synthase or O-succinylhomoserine sulfhydrylase or O-acetylhomoserine sulfhydrylase or the strain containing these enzyme activities by using .O-succinylhomoserine or O-acetylhomoserine produced from the above L-methionine precursor producing strain and methylmercaptan as a substrate.

More particularly, the present invention provides the method for producing L-methionine by enzyme reaction of cystathionine synthase or O-succinylhomoserine sulfhydrylase or O-acetylhomoserine sulfhydrylase by using homoserine, O-phospho homoserine, O-succinyl homoserine or O-acetyl homoserine accumulated from the above method as a substrate. It is preferred in the present invention to use O-succinylhomoserine or O-acetylhomoserine as a substrate.

In the present invention, the cystathionine gamma synthase or O-succinylhomoserine sulfhydrylase or O-acetylhomoserine sulfhydrylase can be derived from *Escherichia* Sp., *Pseudomonas* sp., *Leptospira* sp., *Corynebacterium* sp., *Saccharomyces* sp., *Chromobacterium* sp., *Nocardia* sp., *Bradyrhizobium* sp., *Hyphomonas* sp., *Methylococcus* sp., *Methylobacillus* sp., *Nitrosomonas* sp., *Klebsiella* sp., *Bacillus* sp., *Shigella* sp., *Colwellia* sp., *Salmonella* sp., yeast, or fungi.

In step 2) process, where O-succinylhomoserine is used as an L-methionine precursor, preferably cystathionine gamma synthase or O-succinylhomoserine sulfhydrylase or O-acetylhomoserine sulfhydrylase derived from *Pseudomonas* sp., *Nocardia* sp. or *Chromobacterium* sp., more preferably derived from *Pseudomonas aurogenosa, Nocardia Farcinica, Pseudomonas putida* or *Chromobacterium Violaceum* can be used.

In step 2) process, where O-acetylhomoserine is used as an L-methionine precursor, preferably cystathionine gamma synthase or O-succinylhomoserine sulfhydrylase or O-acetylhomoserine sulfhydrylase derived from *Leptospira* sp., *Chromobacterium* sp., or *Hyphomonas* sp., more preferably derived from *Leptospira meyeri, Pseudomonas aurogenosa, Hyphomonas Neptunium* or *Chromobacterium Violaceum* can be used.

The enzyme reactions above are as shown in the following reaction formulas and the structural formulas are shown in FIG. 2.

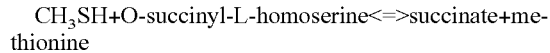

$CH_3SH$+O-succinyl-L-homoserine$\Leftrightarrow$succinate+methionine $CH_3SH$+O-acetyl-L-homoserine$\Leftrightarrow$acetate+methionine In the above reactions, as shown in formulas of FIG. 2, $CH_3S$— residue of methylmercaptan is substituted with succinate or acetate residue of O-succinylhomoserine or O-acetylhomoserine to produce methionine. Methylmercaptan ($CH_3SH$) can be added in different forms during the reaction.

The sequence of the genes encoding the enzymes having the above enzyme activity can be obtained from the database of NCBI, USA, and DNA data bank (KEGG), Japan.

For the biological conversion reaction, a gene is cloned from the obtained gene sequence, which is then introduced into an expression vector. The enzyme is expressed in active form from a recombinant strain. Both the enzyme expressing strain and the expressed enzyme can be directly used for the reaction.

The enzymes expressed from above genes or the microbial strains expressing those enzymes can be directly mixed, partly or not, with the fermentation supernatant or the fermentation broth accumulated with L-methionine precursor to start the reaction. In a preferred embodiment of the invention, O-succinylhomoserine or O-acetylhomoserine accumulated in the fermentation solution can be converted into methionine by cystathionine gamma synthase or O-acetylhomoserine sulfhydrylase or O-succinylhomoserine sulfhydrylase derived from *Pseudomonas* sp., *Chromobacterium* sp., *Leptospira* sp. or *Hyphomonas* sp.

More preferably, O-succinylhomoserine accumulated in the fermentation solution is converted into methionine by cystathionine gamma synthase or O-acetylhomoserine sulfhydrylase or O-succinylhomoserine sulfhydrylase derived from *Pseudomonas aurogenosa, Pseudomonas putida* or *Chromobacterium Violaceum*.

O-acetylhomoserine accumulated in the fermentation solution is converted into methionine by cystathionine gamma synthase or O-acetylhomoserine sulfhydrylase or O-succinylhomoserine sulfhydrylase derived from *Leptospira meyeri, Hyphomonas Neptunium* or *Chromobacterium Violaceum*.

Each gene was expressed in pCL-CJ1 vector (CJ, Korea), the expression vector for *E. coli*, and the expressed protein was obtained from enzyme solution prepared by cell lysis using sonication. The enzyme solution was added to the fermentation solution accumulated O-succinylhomoserine or O-acetylhomoserine, and methylmercaptan solution was also added thereto to start the reaction. The reaction was confirmed using DTNB (5,5-dithiobis(2-nitro-benzoic acid, Sigma, USA) and the reaction product was analyzed by HPLC.

In the present invention, byproducts such as succinic acid or acetic acid can be additionally obtained, without a separate production process, by the reaction of $CH_3SH$ with O-succinylhomoserine and O-acetylhomoserine respectively.

BRIEF DESCRIPTION OF THE DRAWINGS

The application of the preferred embodiments of the present invention is best understood with reference to the accompanying drawings, wherein.

The origin of each enzyme solution is as follows. Enzyme solution #21 is a cell extract not containing a specific gene.

| Strain | Strain number (ATCC) | Gene name (KEGG) | Substrate specificity | |
|---|---|---|---|---|
| | | | OSH | OAH |
| *Escherichia Coli* K12 | 55151 | MetB | + | + |
| *Pseudomonas aurogenosa* | 17933 | MetZ | +++ | + |
| | | MetY | ++++ | ++++ |
| *Pseudomonas putida* | 17390 | MetZ | ++++ | + |
| *Corynebacteria glutamicum* | 13032 | MetB | + | + |
| | | MetY | + | + |
| *Leptospira meyeri* | 43278 | MetY | + | ++ |
| *Saccharomyces cerevisiae* | 2704 | Met25 | + | + |
| *Chromobacterium Violaceum* | 12472 | MetZ | ++++ | +++ |
| *Nocardia Farcinica* | 3318 | MetZ | ++++ | + |
| *Bradyrhizobium Japonicum* | 10324 | MetZ | + | + |
| *Hyphomonas Neptunium* | 49408 | MetZ | + | ++++ |
| *Methylococcus Capsulatus* | 19069D-5 | MetZ | + | + |
| *Methylobacillus Flagellatus* | 51484D | MetZ | + | + |
| *Nitrosomonas Europaea* | 19718D | MetZ | + | + |
| *Klebsiella Pneumoniae* | 25955 | MetB | + | + |
| *Bacillus Subtilis* | 10783 | MetB | + | + |
| *Shigella flexneri* 2457T | 700930D-5 | MetB | + | + |

Figure 5:
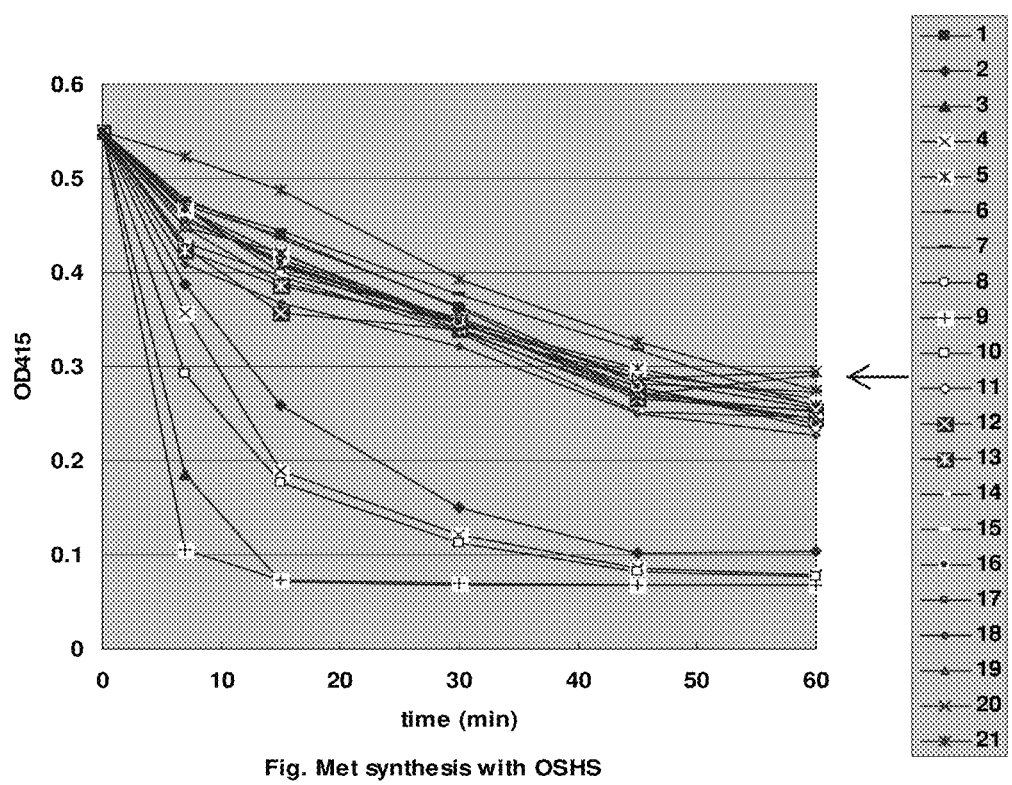
FIG. 5 is a graph showing the reaction curves illustrating the O-succinylhomoserine consumptions by various enzymes.
Figure 6:
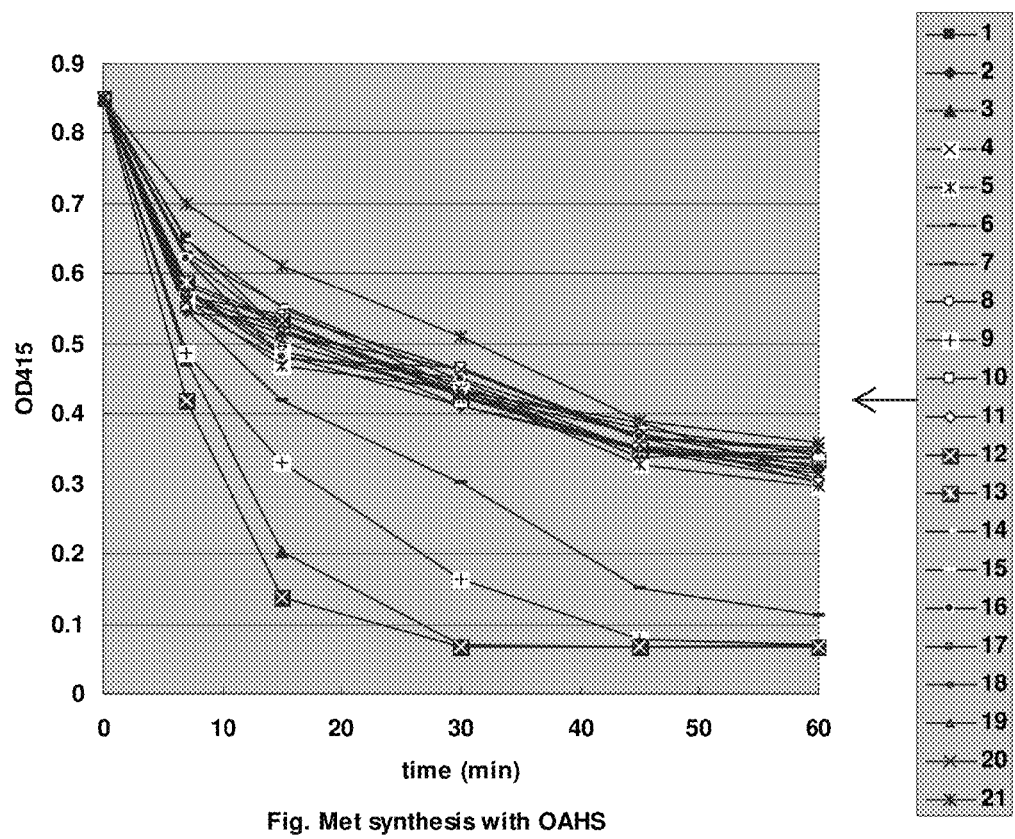

FIG. 6 is a graph showing the reaction curves illustrating the O-acetylhomoserine consumptions by various enzymes. Each number is as shown in FIG. 5.

Figure 7:
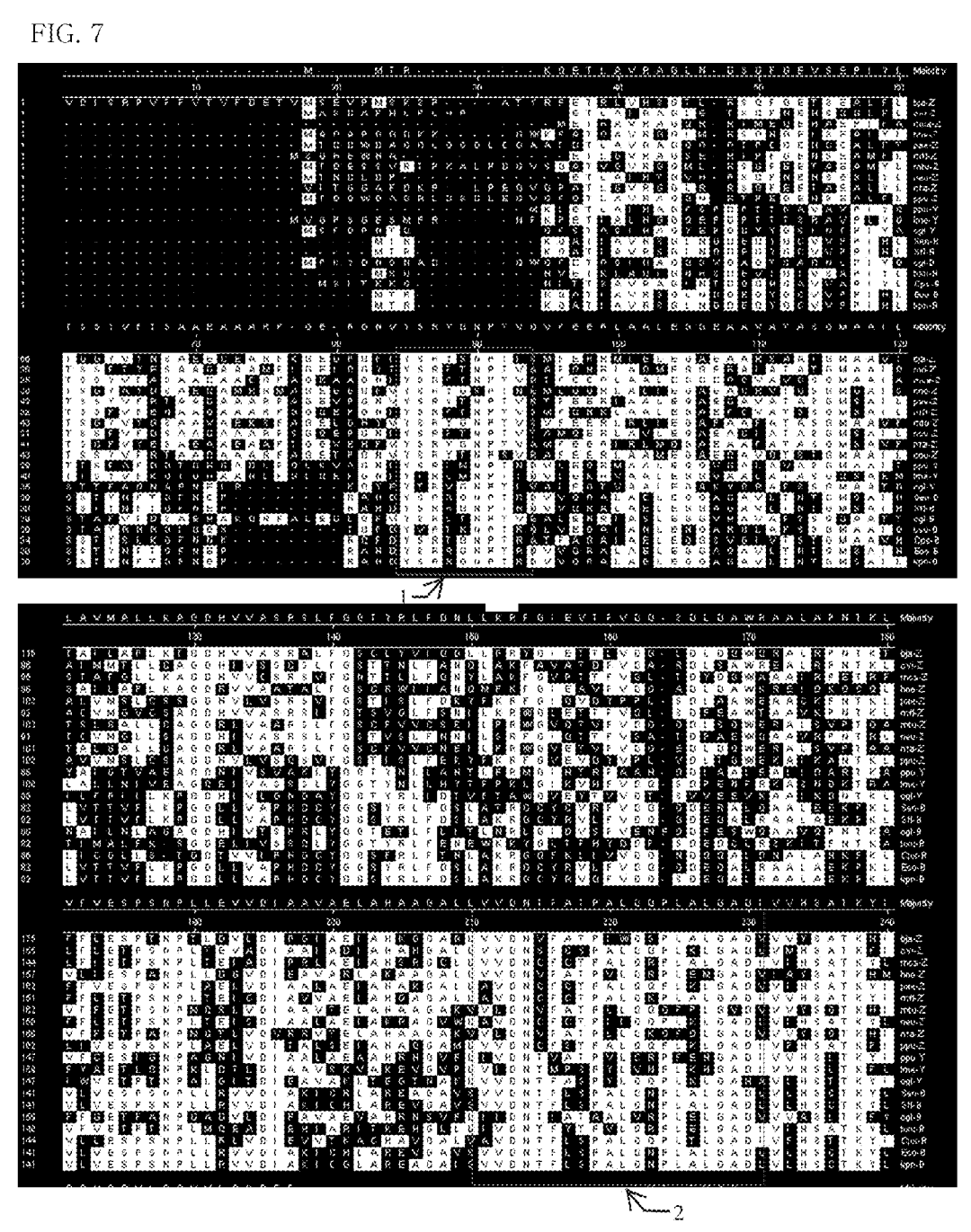

FIG. 7 discloses a diagram illustrating the amino acid sequence of each enzyme used (SEQ ID NOS 58, 56, 60, 59, 77, 61, 78, 62, 57, 79, 55, 80-81, 67, 65, 82, residues 1-371 of 64, 66, 83 and 63, respectively, in order of appearance) for the conversion reaction, arranged by megalign of DNAstar.

Figure 8:
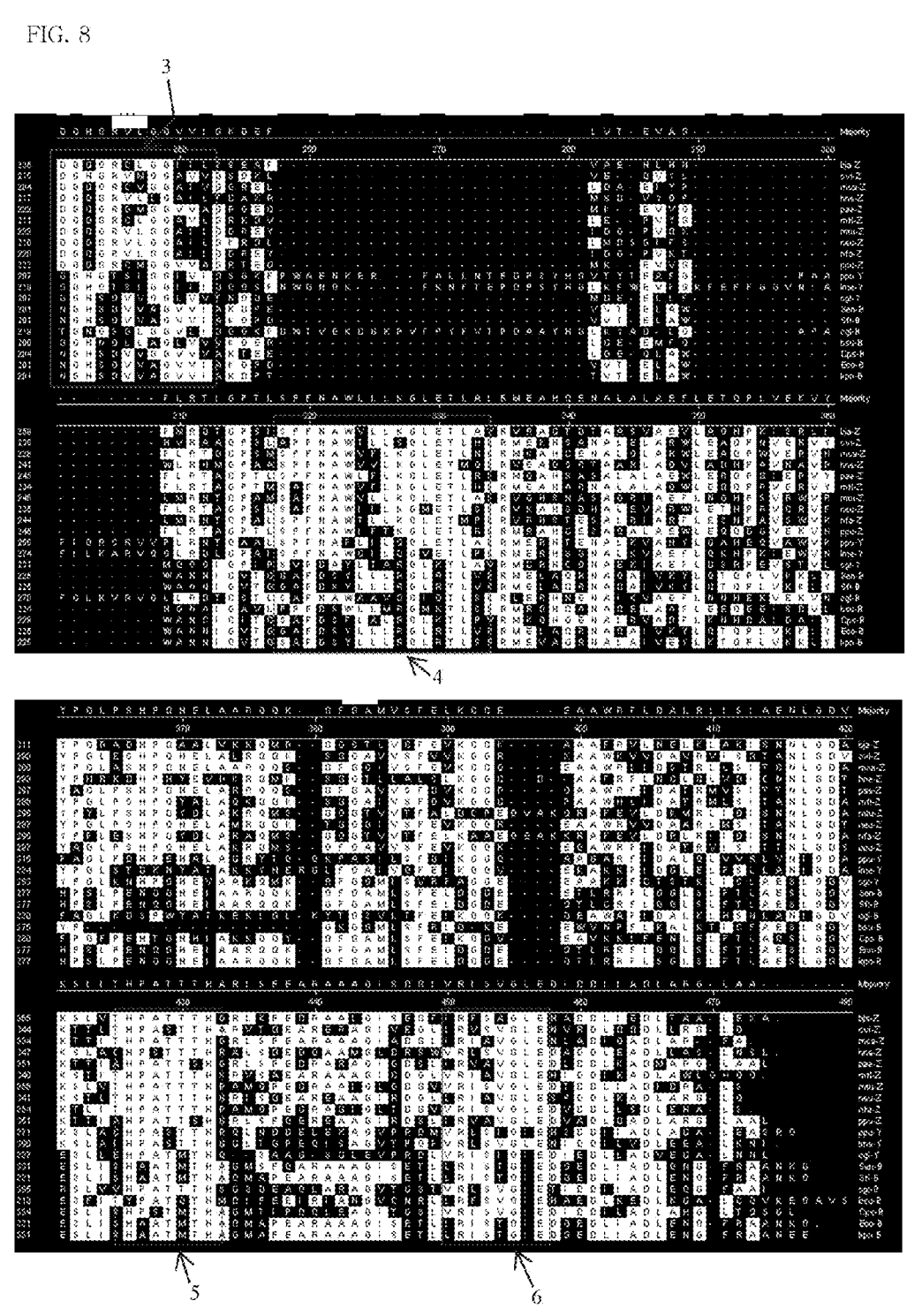

FIG. 8 is the continuation of the diagram of FIG. 7, illustrating the amino acid sequence of each enzyme used (SEQ ID NOS 58, 56, 60, 59, 77, 61, 78, 62, 57, 79, 55, 80-81, 67, 65, 82, residues 1-371 of 64, 66, 83 and 63, respectively, in order of appearance) for the conversion reaction, arranged by megalign of DNAstar.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of a Methionine Precursor Producing Strain

<1-1> Deletion of metB Gene

To deletion metB gene encoding cystathionine synthase in *E. coli* strain, FRT-one-step PCR deletion was performed (PNAS (2000) vol 97: P 6640-6645). Primers of SEQ. ID. NO: 1 and NO: 2 were used for PCR using pKD3 vector (PNAS (2000) vol 97: P 6640-6645) as a template, resulting in the construction of deletion cassette. PCR was performed as follows; 30 cycles of denaturation at 94° C. for 30 seconds, annealing at 55° C. for 30 seconds, extension at 72° C. for 1 minute.

The PCR product was electrophoresed on 1.0% agarose gel, followed by purification of DNA obtained from 1.2 kbp band. The recovered DNA fragment was electroporated into *E. coli* (K12) W3110 transformed with pKD46 vector (PNAS (2000) vol 97: P 6640-6645). Before electroporation, W3110 transformed with pKD46 was cultivated at 30° C. in LB medium containing 100 μg/L of ampicillin and 5 mM of 1-arabinose until $OD_{600}$ reached 0.6. Then, the cultured strain was washed twice with sterilized distilled water and one more time with 10% glycerol. Electroporation was performed at 2500 V. The recovered strain was streaked on LB plate medium containing 25 μg/L of chloramphenicol, followed by culture at 37° C. for overnight. Then, a strain exhibiting resistance was selected.

PCR was performed by using the selected strain as a template with the same primers as the above under the same condition. The deletion of metB gene was identified by confirming the 1.2 kb sized gene on 1.0% agarose gel. The strain was then transformed with pCP20 vector (PNAS (2000) vol 97: P 6640-6645) and cultured in LB medium. The final metB knock-out strain was constructed in which the size of metB gene reduced to 150 bp on 1.0% agarose gel by PCR under the same conditions. Chloramphenicol marker was confirmed to be eliminated. The constructed strain was named W3-B.

<1-2> Deletion of thrB Gene

The inventors tried to increase O-succinylhomoserine synthesis from homoserine by deletion of thrB gene encoding homoserine kinase. Particularly, where a threonine producing strain was used, deletion of this gene was quite necessary because the activity of use of homoserine was very strong. To deletion thrB gene in the W3-B strain constructed above, FRT one step PCR deletion was performed by the same manner as described above for the deletion of metB gene.

To construct thrB deletion cassette, PCR was performed by using pKD4 vector (PNAS (2000) vol 97: P 6640-6645) as a template with primers of SEQ. ID. NO: 3 and NO: 4 as follows; 30 cycles of denaturation at 94° C. for 30 seconds, annealing at 55° C. for 30 seconds, extension at 72° C. for 1 minute. The PCR product was electrophoresed on 1.0% agarose gel, followed by purification of DNA obtained from 1.6 kbp band. The recovered DNA fragment was electroporated into the W3-B strain transformed with pKD46 vector. The recovered strain was streaked on LB plate medium containing 50 μg/L of kanamycin, followed by culture at 37° C. for overnight. Then, a strain exhibiting resistance was selected.

PCR was performed by using the selected strain as a template with primers of SEQ. ID. NO: 3 and NO: 4 under the same conditions as the above. The deletion of ThrB gene was identified by selecting the strain whose size is 1.6 kb on 1.0% agarose gel. The strain was then transformed with pCP20 vector and cultured in LB medium. The final thrB knock out strain was constructed in which the size of thrB gene reduced to 150 kb on 1.0% agarose gel by PCR under the same conditions. Kanamycin marker was confirmed to be eliminated. The constructed strain was named W3-BT.

<1-3> Deletion of metJ Gene

To deletion metJ gene which is the regulator gene of metA gene involved in methionine precursor synthesis, FRT one step PCR deletion was performed by the same manner as used for the deletion of metB gene.

To construct metJ deletion cassette, PCR was performed with primers of SEQ. ID. NO: 5 and NO: 6 as follows; 30 cycles of denaturation at 94° C. for 30 seconds, annealing at 55° C. for 30 seconds, extension at 72° C. for 1 minute.

The PCR product was electrophoresed on 1.0% agarose gel, followed by purification of DNA obtained from 1.2 kbp band. The recovered DNA fragment was electroporated into the W3-BT strain transformed with pKD46 vector. The recovered strain was streaked on LB plate medium containing chloramphenicol, followed by culture at 37° C. for overnight. Then, a strain exhibiting resistance was selected.

PCR was performed by using the selected strain as a template with primers of SEQ. ID. NO: 7 and NO: 8 under the same conditions as the above. The deletion of metJ was identified by confirming the 1.6 kb sized gene on the 1.0% agarose gel. The strain was then transformed with pCP20 vector and cultured in LB medium. The final metJ knock out strain was constructed in which the size of metJ gene reduced to 600 kb on 1.0% agarose gel by PCR under the same conditions and the strain Chloramphenicol marker was confirmed to be eliminated. The constructed strain was named W3-BTJ.

<1-4-Over-Expression of metA Gene

To increase methionine precursor synthesis, metA gene encoding homoserine O-succinyl transferase involved in the synthesis of O-succinylhomoserine, the methionine precursor, was over-expressed.

PCR was performed by using the chromosome of *E. coli* w3110 as a template with primers of SEQ. ID. NO: 9 and NO: 10 as follows; 25 cycles of denaturation at 94° C. for 30 seconds, annealing at 55° C. for 30 seconds, extension at 72° C. for 2 minutes.

Figure 1:
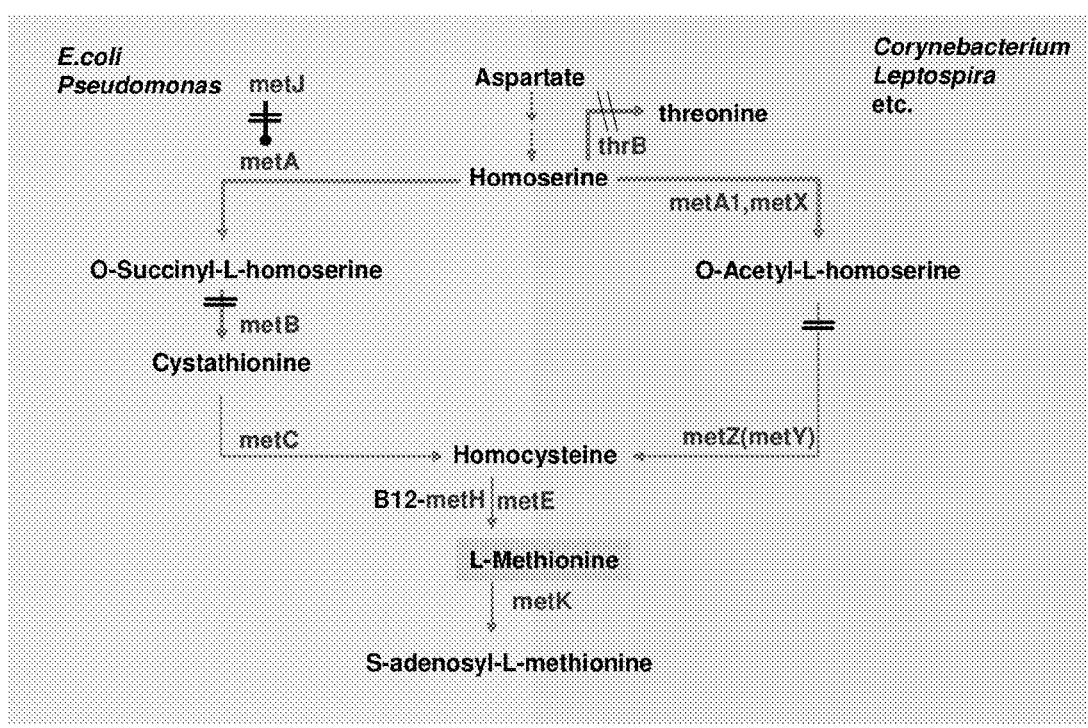
FIG. 1 is a diagram illustrating genetic manipulation of the methionine precursor producing strain.
Figure 2:
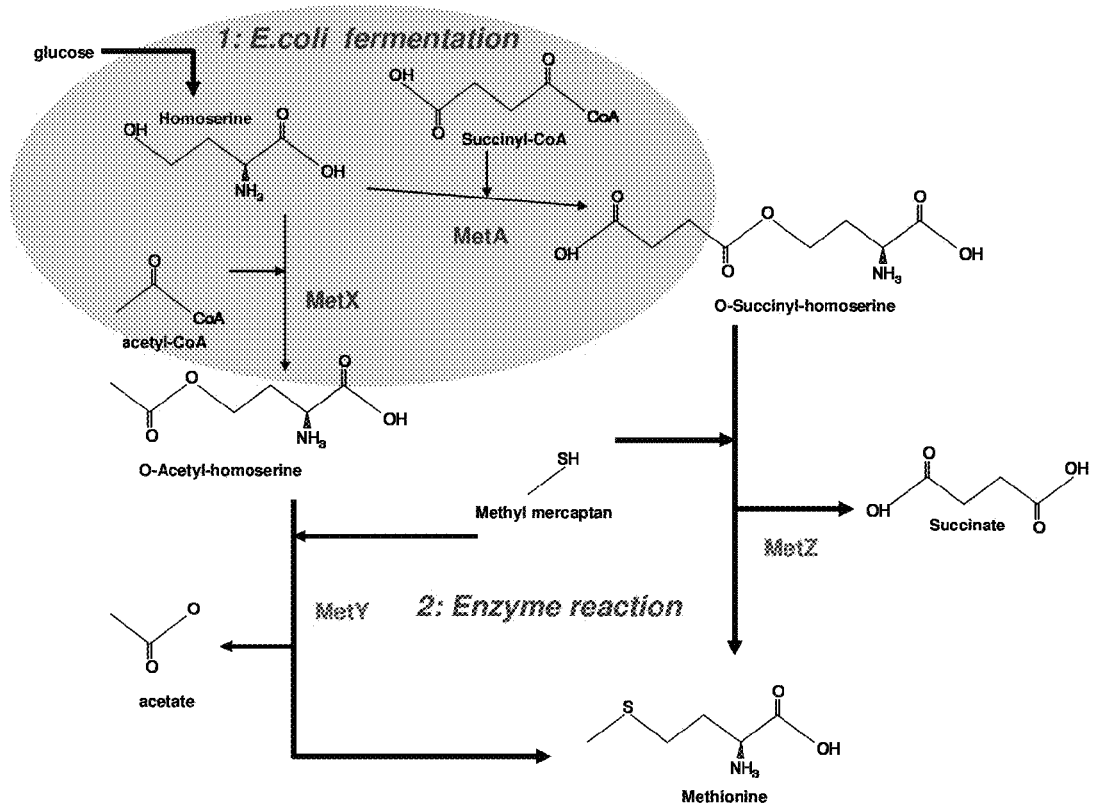
FIG. 2 is a diagram illustrating chemical structures of 2-step process for the production of methionine.
Figure 3:
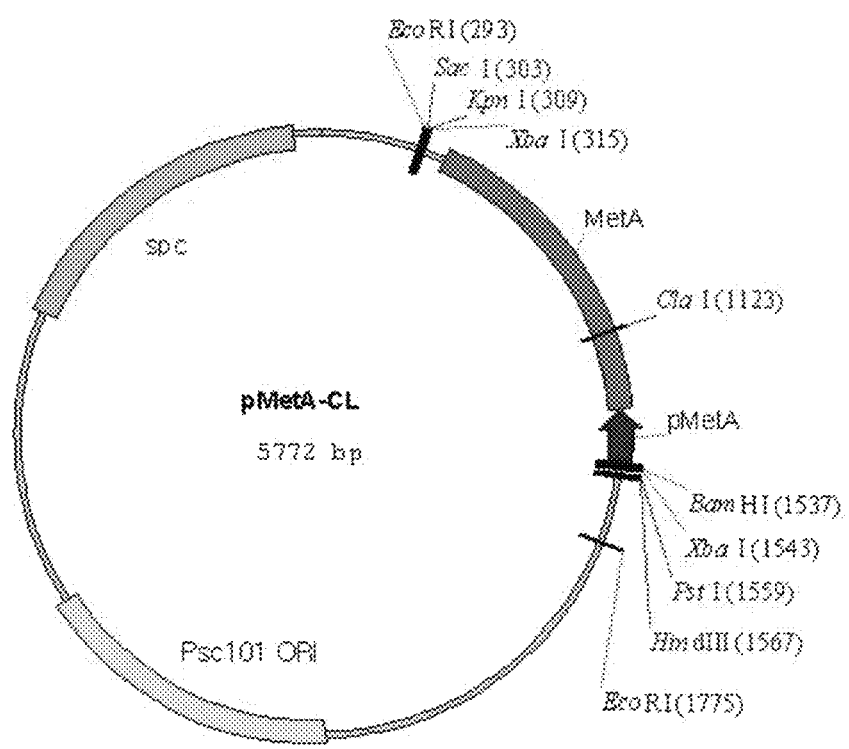
FIG. 3 is a schematic diagram of pMetA-CL for the expression of metA gene.

The PCR product was electrophoresed on 1.0% agarose gel, followed by purification of DNA obtained from 1.2 kbp band. The recovered DNA fragment was ligated to another DNA fragment obtained from pCL1920 vector by digesting with Sma1. *E. coli* was transformed with the ligated vector, which was then cultured in LB medium containing 50 μg/L of spectinomycin, followed by selection. The vector constructed thereby was named pMetA-CL. The schematic diagram of the pMetA-CL is shown in FIG. 3. W3-BTJ strain was transformed with the said vector. The constructed strain was named W3-BTJ/pMetA-CL and the increase of O-succinylhomoserine level therein was observed.

As another method to increase metA gene expression, metA gene was ligated to pCL1920 vector by using CJ1 promoter (CJ, Korea) and EcoRV. *E. coli* was transformed with the ligated vector, which was then cultured in LB medium containing 50 µg/L of spectinomycin, followed by selection. The vector constructed thereby was named pCJ-MetA-CL. W3-BTJ strain was transformed with the said vector. The constructed strain was named W3-BTJ/pCJ-MetA-CL and the increase of O-succinylhomoserine level therein was observed.

<1-4-2> Over-Expression of metX Gene

To synthesize O-acetylhomoserine, metX gene encoding homoserine O-acetyl transferase involved in the synthesis of O-acetylhomoserine, the methionine precursor, was over-expressed.

PCR was performed by using the chromosome of *Leptospira meyeri* as a template with primers of SEQ. ID. NO: 11 and NO: 12 as follows; 25 cycles of denaturation at 94° C. for 30 seconds, annealing at 55° C. for 30 seconds, extension at 72° C. for 2 minutes.

The PCR product was electrophoresed on 1.0% agarose gel, followed by purification of DNA obtained from 1.1 kbp band. The recovered DNA fragment was ligated to pCL1920 vector by using CJ1 promoter and EcoRV. *E. coli* was transformed with the ligated vector, which was then cultured in LB medium containing 50 µg/L of spectinomycin, followed by selection. The vector constructed thereby was named pCJ1-MetXlme-CL. W3-BTJ strain was transformed with the said vector. The constructed strain was named W3-BTJ/pCJ-MetXlme-CL and the increase of O-acetylhomoserine level therein was observed.

Another method to over-express metX gene was made by performing PCR using the chromosome of *Corynebacterium* as a template with primers of SEQ. ID. NO: 68 and NO: 69 as follows; 25 cycles of denaturation at 94° C. for 30 seconds, annealing at 55° C. for 30 seconds, extension at 72° C. for 2 minutes.

The PCR product was electrophoresed on 1.0% agarose gel, followed by purification of DNA. The recovered DNA fragment was ligated to pCL1920 vector by using CJ1 promoter and EcoRV. *E. coli* was transformed with the ligated vector, which was then cultured in LB medium containing 50 µg/L of spectinomycin, followed by selection. The vector constructed thereby was named pCJ-MetXcgl-CL. W3-BTJ strain was transformed with the said vector. The constructed strain was named W3-BTJ/pCJ-MetXcgl-CL and the increase of O-acetylhomoserine level therein was observed.

<1-4-3> Deletion of metA Gene

To increase the production of O-acetylhomoserine, metA gene encoding homoserine O-succinyl transferase was deleted in W3-BTJ strain. Based on the founding that only metX gene introduction resulted in the accumulation of O-succinylhomoserine, it was expected that metA gene deletion resulted in the promotion of the accumulation of O-acetylhomoserine (Table 3). To deletion metA gene, FRT one step PCR deletion was performed.

To construct metA deletion cassette, PCR was performed with primers of SEQ. ID. NO: 70 and NO: 71 as follows; 30 cycles of denaturation at 94° C. for 30 seconds, annealing at 55° C. for 30 seconds, extension at 72° C. for 1 minute.

The PCR product was electrophoresed on 1.0% agarose gel, followed by purification of DNA obtained from 1.2 kbp band. The recovered DNA fragment was electroporated into the *E. coli* W3-BTJ strain transformed with pKD46 vector. The recovered strain was streaked on LB plate medium containing chloramphenicol, followed by culture at 37° C. for overnight. Then, a strain exhibiting resistance was selected.

PCR was performed by using the selected strain as a template with primers of SEQ. ID. NO: 70 and NO: 71 under the same conditions as the above. The deletion of metA gene was identified by confirming 1.1 kb sized gene on 1.0% agarose gel. The strain was then transformed with pCP20 vector and cultured in LB medium. The final metA knock out strain was constructed in which the size of metA gene reduced to 100 kb on 1.0% agarose gel by PCR under the same conditions. Chloramphenicol marker was confirmed to be eliminated. The constructed strain was named W3-BTJA. The W3-BTJA strain was transformed with the pCJ-MeTXlme-CL vector and the resultant strain was named W3-BTJA/pCJ-MetX-CL. The strain was cultured by the same manner as described above and as a result the accumulation of O-succinylhomoserine was not observed but the production of O-acetylhomoserine was significantly, approximately 20% increased, compared with W3-BTJ.

<1-5> Conversion of L-Threonine Producing Strain

Methionine precursor-producing strains were constructed by the same manner as described in Examples <1-1> to <1-3> using *E. coli* CJM002 (KCCM-10568), the L-threonine producing strain free from the requirement for methionine. The constructed strains were named CJM-BTJ, CJM-BTJ/pMetA-CL and CJM-BTJ/pCJ-MetA-CL, respectively. The metA gene knock-out strain was also constructed by the same manner as described in <1-4-3> using the CJM-BTJ strain and the resultant strain was named CJM-BTJA.

Example 2

Fermentation for the Production of L-Methionine Precursor

<2-1> Experiment of Flask Culture

To investigate the methionine precursor production capacity of the strain constructed in Example 1, Erlenmeyer flask culture was performed. W3-BTJ, CJM-BTJ and W3-BTJ transformed with metA and metX expression vector were cultured on LB plate media containing spectinomycin at 31° C. for overnight. A single colony was inoculated in 3 ml of LB medium containing spectinomycin, followed by culture at 31° C. for 5 hours. The culture solution was 200 fold diluted in 250 ml Erlenmeyer flask containing 25 ml of methionine precursor producing medium, followed by culture at 31° C., 200 rpm for 64 hours. HPLC was performed to compare with methionine precursor production capacity (Table 2 and Table 3). As a result, methionine production capacity was significantly increased in the methionine precursor-producing strain prepared from the L-threonine producing strain free from the requirement for methionine.

TABLE 1

| Flask medium composition for methionine precursor production | |
|---|---|
| Composition | Concentration (per liter) |
| Glucose | 40 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |

TABLE 1-continued

Flask medium composition for methionine precursor production

| Composition | Concentration (per liter) |
|---|---|
| Yeast extract | 2 g |
| Methionine | 0.15 g |
| Threonine | 0.15 g |

TABLE 2

Methionine precursor (O-succinylhomoserine) production by flask culture

| | OD | Glucose consumption (g/L) | O-succinylhomoserine (g/L) |
|---|---|---|---|
| W3-BTJ | 10 | 40 | 0.3 |
| W3-BTJ/pMetA-CL | 12 | 40 | 1.2 |
| W3-BTJ/pCJ-MetA-CL | 12 | 40 | 1.8 |
| CJM-BTJ | 5.0 | 33 | 0.6 |
| CJM-BTJ/pMetA-CL | 6.0 | 36 | 5.2 |
| CJM-BTJ/pCJ-MetA-CL | 6.0 | 40 | 10.1 |

TABLE 3

Methionine precursor (O-acetylhomoserine) production by flask culture

| | OD | Glucose consumption (g/L) | O-acetylhomoserine (g/L) |
|---|---|---|---|
| W3-BTJ | 10 | 40 | 0 |
| W3-BTJ/pCJ-MetXlme-CL | 12 | 40 | 1.5 |
| W3-BTJ/pCJ-metXcgl-CL | 12 | 40 | 1.4 |
| W3-BTJA/pCJ-metXlme-CL | 11 | 40 | 1.8 |
| CJM-BTJ | 5.0 | 33 | 0 |
| CJM-BTJ/pCJ-metXlme-CL | 5.5 | 40 | 4.8 |
| CJM-BTJ/pCJ-MetXcgl-CL | 6.0 | 36 | 4.6 |
| CJM-BTJA/pCJ-metX-CL | 5.8 | 40 | 6.5 |

<2-2> Large Scale Fermentation

A strain exhibiting the highest methionine precursor production capacity in Example 1 was selected to mass-produce methionine precursor, which was then cultured in a 5 L fermentor. CJM-BTJ/pCJ-metA-CL or CJM-BTJA/pCJ-metXlme-CL was inoculated in LB medium containing spectinomycin, followed by culture at 31° C. for overnight. Then, a single colony was inoculated in 10 ml LB medium containing spectinomycin, which was cultured at 31° C. for 5 hours. The culture solution was 100 fold diluted in 1000 ml Erlenmeyer flask containing 200 ml of methionine precursor seed medium, followed by culture at 31° C., 200 rpm for 3-10 hours. The culture solution was inoculated in a 5 L fermentor, followed by further culture for 50-100 hours by fed-batch fermentation. The methionine precursor concentration in the fermented solution was measured by HPLC and the results are shown in Table 5.

TABLE 4

Fermentor medium composition for methionine precursor production

| Composition | Seed media | Main media | Feed media |
|---|---|---|---|
| Glucose(g/L) | 10.1 | 40 | 600 |
| MgSO$_4$7H$_2$0(g/L) | 0.5 | 4.2 | |
| Yeast extract(g/L) | 10 | 3.2 | |

TABLE 4-continued

Fermentor medium composition for methionine precursor production

| Composition | Seed media | Main media | Feed media |
|---|---|---|---|
| KH$_2$PO$_4$ | 3 | 3 | 8 |
| Ammonium sulfate(g/L) | | 6.3 | |
| NH$_4$Cl(g/L) | 1 | | |
| NaCl(g/L) | 0.5 | | |
| Na$_2$HPO$_4$12H$_2$O(g/L) | 5.07 | | |
| DL-Methionine(g/L) | | 0.5 | 0.5 |
| L-Isoleucine(g/L) | 0.05 | 0.5 | 0.5 |
| L-Threonine(g/L) | | 0.5 | 0.5 |

TABLE 5

Methionine precursor production in a fermentor

| | O-succinylhomoserine (g/L) | O-acetylhomoserine (g/L) |
|---|---|---|
| CJM-BTJ/pCJ-MetA-CL | >80 | 0 |
| CJM-BTJA/pCJ-MetXlme-CL | 0 | >55 |

Example 3

Production of Methionine Converting Enzyme

<3-1> Cystathionine Gamma Synthase Derived from *E. Coli*

The metB gene encoding cystathionine gamma synthase derived from *E. coli*, which would be used for the conversion of O-succinylhomoserine or O-acetylhomoserine, the methionine precursor, into methionine, was cloned.

PCR was performed by using the chromosome of *E. coli* as a template with primers of SEQ. ID. NO: 13 and NO: 14 as follows; 25 cycles of denaturation at 94° C. for 30 seconds, annealing at 55° C. for 30 seconds, extension at 72° C. for 2 minutes.

Figure 4:
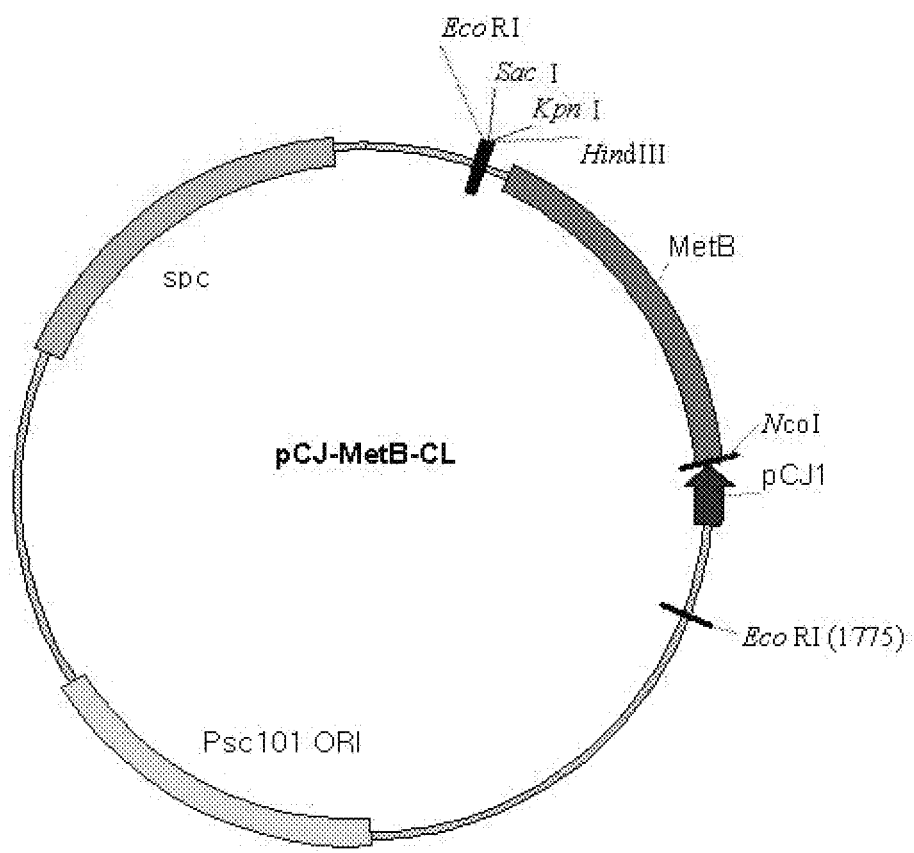
FIG. 4 is a schematic diagram of pCJ-MetB-CL for the expression of metB gene.

The obtained DNA fragment was digested with NcoI/HindIII and cloned into pCL-CJ1 vector (CJ, Korea) digested with the same enzymes. The resultant vector was named pCJ-MetB-CL and the schematic diagram is shown in FIG. 4. *E. coli* W3110 was transformed with the cloned vector and then cultured on LB plate medium containing 50 µg/L of spectinomycin, followed by colony selection. The selected colony was inoculated in 3 ml of LB medium containing 50 µg/L of spectinomycin, followed by culture at 37° C. for overnight. The cultured cells were recovered, washed with 0.1 M potassium phosphate buffer (pH 7.5), suspended in 200 µL of potassium phosphate buffer, and lysed by sonication 5 times at 30 seconds intervals. The cell lysate was centrifuged at 12,000 rpm for 10 minutes and the supernatant was obtained to quantify the total protein level by using Bio-Rad protein quantification solution (BIO-Rad, USA). Protein expression was identified by SDS-PAGE. The supernatant obtained from the cell extract was used for the enzyme conversion reaction.

<3-2> O-Succinylhomoserine Sulfhydrylase Derived from *Pseudomonas* Sp.

The metZ gene encoding O-succinylhomoserine sulfhydrylase derived from *Pseudomonas* sp., which would be used for the conversion of O-succinylhomoserine or O-acetylhomoserine, the methionine precursor, into methionine, was cloned. As the *Pseudomonas* sp. microorganism, *Pseudomonas aeruginosa* and *Pseudomonas putida* were used.

PCR was performed by using the chromosome of each strain as a template with primers of SEQ. ID. NO: 15 and NO: 16 for the *Pseudomonas aeruginosa* and primers of SEQ. ID. NO: 17 and NO: 18 for the *Pseudomonas putida* as follows; 30 cycles of denaturation at 94° C. for 30 seconds, annealing at 55° C. for 30 seconds, extension at 72° C. for 2 minutes.

The obtained DNA fragment was digested with NdeI/PacI and cloned into pCL-CJ1 vector (CJ, Korea) digested with the same enzymes. The supernatant of cell extract was obtained using the cloned vector by the same manner as described in Example <1-1> and used for the enzyme conversion reaction.

<3-3> O-Acetylhomoserine Sulfhydrylase Derived from *Pseudomonas* Sp.

The metY gene encoding O-acetylhomoserine sulfhydrylase derived from *Pseudomonas* sp., which would be used for the conversion of O-succinylhomoserine or O-acetylhomoserine, the methionine precursor, into methionine, was cloned.

PCR was performed by using the chromosome of *Pseudomonas aeruginosa* as a template with primers of SEQ. ID. NO: 19 and NO: 20 as follows; 30 cycles of denaturation at 94° C. for 30 seconds, annealing at 55° C. for 30 seconds, extension at 72° C. for 2 minutes.

The obtained DNA fragment was digested with NdeI/PacI and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-4> Cystathionine Synthase Derived from *Corynebacterium* glutamicum

The metB gene encoding cystathionine synthase derived from *Corynebacterium glutamicum*, which would be used for the conversion of O-succinylhomoserine or O-acetylhomoserine, the methionine precursor, into methionine, was cloned.

PCR was performed by using the chromosome of *Corynebacterium glutamicum* as a template with primers of SEQ. ID. NO: 21 and NO: 22 as follows; 30 cycles of denaturation at 94° C. for 30 seconds, annealing at 55° C. for 30 seconds, extension at 72° C. for 2 minutes.

The obtained DNA fragment was digested with NcoI/HindIII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-5> O-Acetylhomoserine Sulfhydrylase Derived from *Corynebacterium* glutamicum The metZ gene encoding O-acetylhomoserine sulfhydrylase derived from *Corynebacterium glutamicum*, which would be used for the conversion of O-succinylhomoserine or O-acetylhomoserine, the methionine precursor, into methionine, was cloned.

PCR was performed by using the chromosome of *Corynebacterium glutamicum* as a template with primers of SEQ. ID. NO: 23 and NO: 24 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-6> O-Acetylhomoserine Sulfhydrylase Derived from *Leptospira* Sp.

The metY gene encoding O-acetylhomoserine sulfhydrylase derived from *Leptospira* meyeri, which would be used for the conversion of O-succinylhomoserine or O-acetylhomoserine, the methionine precursor, into methionine, was cloned.

PCR was performed by using the chromosome of *Leptospira* meyeri as a template with primers of SEQ. ID. NO: 25 and NO: 26 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-7> O-Acetylhomoserine Sulfhydrylase Derived from *Saccharomyces* Sp.

The met25 gene encoding O-acetylhomoserine sulfhydrylase derived from *Saccharomyces cerevisiae*, which would be used for the conversion of O-succinylhomoserine or O-acetylhomoserine, the methionine precursor, into methionine, was cloned.

PCR was performed by using the chromosome of *Saccharomyces cerevisiae* as a template with primers of SEQ. ID. NO: 27 and NO: 28 as follows; 30 cycles of denaturation at 94° C. for 30 seconds, annealing at 55° C. for 30 seconds, extension at 72° C. for 2 minutes.

The obtained DNA fragment was digested with NdeI/PacI and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-8> O-Succinylhomoserine Sulfhydrylase Derived from *Chromobacterium* sp.

The metZ gene encoding O-succinylhomoserine sulfhydrylase derived from *Chromobacterium* Violaceum, which would be used for the conversion of O-succinylhomoserine or O-acetylhomoserine, the methionine precursor, into methionine, was cloned.

PCR was performed by using the chromosome of *Chromobacterium* Violaceum as a template with primers of SEQ. ID. NO: 29 and NO: 30 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-9> O-Succinylhomoserine Sulfhydrylase Derived from *Nocardia* Sp.

The metZ gene encoding O-succinylhomoserine sulfhydrylase derived from *Nocardia* Farcinica, which would be used for the conversion of O-succinylhomoserine or O-acetylhomoserine, the methionine precursor, into methionine, was cloned.

PCR was performed by using the chromosome of *Nocardia* Farcinica as a template with primers of SEQ. ID. NO: 31 and NO: 32 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-10> O-Succinylhomoserine Sulfhydrylase Derived from *Bradyrhizobium* Sp.

The metZ gene encoding O-succinylhomoserine sulfhydrylase derived from *Nocardia Farcinica*, which would be used for the conversion of O-succinylhomoserine or O-acetylhomoserine, the methionine precursor, into methionine, was cloned.

PCR was performed by using the chromosome of *Bradyrhizobium Japonicum* as a template with primers of SEQ. ID. NO: 33 and NO: 34 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-11> O-Succinylhomoserine Sulfhydrylase Derived from *Hyphomonas* Sp.

The metZ gene encoding O-succinylhomoserine sulfhydrylase derived from *Hyphomonas Neptunium*, which would be used for the conversion of O-succinylhomoserine or O-acetylhomoserine, the methionine precursor, into methionine, was cloned.

PCR was performed by using the chromosome of *Hyphomonas Neptunium* as a template with primers of SEQ. ID. NO: 35 and NO: 36 as follows; 30 cycles of denaturation at 94° C. for 30 seconds, annealing at 55° C. for 30 seconds, extension at 72° C. for 2 minutes.

The obtained DNA fragment was digested with BamHI/HindIII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-12> O-Succinylhomoserine Sulfhydrylase Derived from *Methylococcus* Sp.

The metZ gene encoding O-succinylhomoserine sulfhydrylase derived from *Methylococcus Capsulatus*, which would be used for the conversion of O-succinylhomoserine or O-acetylhomoserine, the methionine precursor, into methionine, was cloned.

PCR was performed by using the chromosome of *Methylococcus Capsulatus* as a template with primers of SEQ. ID. NO: 37 and NO: 38 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-13> O-Succinylhomoserine Sulfhydrylase Derived from *Methylobacillus* Sp.

The metZ gene encoding O-succinylhomoserine sulfhydrylase derived from *Methylobacillus Flagellatus*, which would be used for the conversion of O-succinylhomoserine or O-acetylhomoserine, the methionine precursor, into methionine, was cloned.

PCR was performed by using the chromosome of *Methylobacillus Flagellatus* as a template with primers of SEQ. ID. NO: 39 and NO: 40 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-14> O-Succinylhomoserine Sulfhydrylase Derived from *Nitrosomonas* Sp.

The metZ gene encoding O-succinylhomoserine sulfhydrylase derived from *Nitrosomonas Europaea*, which would be used for the conversion of O-succinylhomoserine or O-acetylhomoserine, the methionine precursor, into methionine, was cloned.

PCR was performed by using the chromosome of *Nitrosomonas Europaea* as a template with primers of SEQ. ID. NO: 41 and NO: 42 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-15> Cystathionine Synthase Derived from *Klebsiella* Sp.

The metB gene encoding cystathionine synthase derived from *Klebsiella Pneumoniae*, which would be used for the conversion of O-succinylhomoserine or O-acetylhomoserine, the methionine precursor, into methionine, was cloned.

PCR was performed by using the chromosome of *Klebsiella Pneumoniae* as a template with primers of SEQ. ID. NO: 43 and NO: 44 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-16> Cystathionine Synthase Derived from *Bacillus* Sp.

The metB gene encoding cystathionine synthase derived from *Bacillus Subtilis*, which would be used for the conversion of O-succinylhomoserine or O-acetylhomoserine, the methionine precursor, into methionine, was cloned.

PCR was performed by using the chromosome of *Bacillus Subtilis* as a template with primers of SEQ. ID. NO: 45 and NO: 46 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-17> Cystathionine Synthase Derived from *Shigella* Sp.

The metB gene encoding cystathionine synthase derived from *Shigella flexneri* 2457T, which would be used for the conversion of O-succinylhomoserine or O-acetylhomoserine, the methionine precursor, into methionine, was cloned.

PCR was performed by using the chromosome of *Shigella flexneri* 2457T as a template with primers of SEQ. ID. NO: 47 and NO: 48 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-18> Cystathionine Synthase Derived from *Colwellia* Sp.

The metB gene encoding cystathionine synthase derived from *Colwellia Psychrerythraea*, which would be used for the conversion of O-succinylhomoserine or O-acetylhomoserine, the methionine precursor, into methionine, was cloned.

PCR was performed by using the chromosome of *Colwellia Psychrerythraea* as a template with primers of SEQ. ID. NO: 49 and NO: 50 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-19> Cystathionine Synthase Derived from *Salmonella* Sp.

The metB gene encoding cystathionine synthase derived from *Salmonella enterica serovar Paratyphi* A, which would be used for the conversion of O-succinylhomoserine or O-acetylhomoserine, the methionine precursor, into methionine, was cloned.

PCR was performed by using the chromosome of *Salmonella enterica serovar Paratyphi* A as a template with primers of SEQ. ID. NO: 51 and NO: 52 as follows; 30 cycles of denaturation at 94° C. for 30 seconds, annealing at 55° C. for 30 seconds, extension at 72° C. for 2 minutes.

The obtained DNA fragment was digested with NdeI/AvrII and cloned into pCL-CJ1 vector (CJ, Korea) digested with the same enzymes. The supernatant of cell extract was obtained using the cloned vector by the same manner as described in Example <3-1> and used for the enzyme conversion reaction.

<3-20> Comparison of the Activities of the Converting Enzymes Using OSHS as a Substrate The activity of each enzyme solution obtained in Examples <3-1> to <3-19> was compared to select the optimum methionine converting enzyme.

First, O-succinylhomoserine (Sigma, USA) was dissolved in 0.1 M potassium phosphate buffer (pH 7.5) with the concentration of 3 mM. Pyridoxal 5'-phosphate (Sigma, USA) used as a coenzyme was added into the reaction solution with the final concentration of 10 µM. Methylmercaptan (Methylmercaptan, Tokyo Kasei Organic Chemicals, Japan) used as another substrate was added into the reaction solution with the final concentration of 2 mM. 1 ml of the reaction solution was placed in 37° C., to which 10 µL of each enzyme solution (protein conc.: 5 mg/ml) was added. 100 µL of the reaction solution was collected every 5-10 minutes and added into 900 µL of 4 mg/ml DTNB (Sigma, USA) solution. $OD_{415}$ was measured to confirm the on-going of the reaction.

DTNB was reacted with SH group of methylmercaptan remaining in the reaction solution and thus synthesized a yellow substance. Thus, whether the reaction was going on or not was checked by observing the disappearance of yellow color of the reaction solution resulted from the conversion reaction of methylmercaptan into methionine.

As shown in FIG. 5, O-succinylhomoserine sulfhydrylase derived from *Chromobacterium* sp., O-succinylhomoserine sulfhydrylase derived from *Nocardia* sp., O-succinylhomoserine sulfhydrylase and O-acetylhomoserine sulfhydrylase derived from *Pseudomonas* sp. were shown to have high enzyme activities. Other enzymes also showed some degree of activity but their reaction speeds were relatively slow. Reactivity to the substrate of each enzyme was summarized in Table 6. Upon completion of one-hour reaction, HPLC was performed to confirm the final productions of methionine and succinic acid. The results are shown in Table 7.

<3-21> Comparison of the Activities of the Converting Enzymes Using OAHS as a Substrate Experiment was performed with O-acetylhomoserine by the same manner as described in Example <3-20>. O-acetylhomoserine was purified from the supernatant of fermented solution. The same reaction solutions and enzyme solutions as used for the experiment with O-succinylhomoserine were used for the reaction. As shown in FIG. 6, O-succinylhomoserine sulfhydrylase derived from *Hyphomonas* sp., O-acetylhomoserine sulfhydrylase derived from *Pseudomonas* sp., O-succinylhomoserine sulfhydrylase derived from *Chromobacterium* sp. and O-acetylhomoserine sulfhydrylase derived from *Leptospira* sp. were shown to have high enzyme activities. Other enzymes also showed some degree of activity but their reaction speeds were relatively slow. Reactivity to the substrate of each enzyme was summarized in Table 6. Upon completion of one-hour reaction, HPLC was performed to confirm the final productions of methionine and succinic acid. The results are shown in Table 8.

TABLE 6

Conversion reaction of O-succinylhomoserine and O-acetylhomoserine by the enzyme derived from each strain

| Strain | Strain No. (ATCC) | Gene (KEGG) | Substrate specificity OSH | OAH |
|---|---|---|---|---|
| *Escherichia Coli* K12 | 55151 | MetB | + | + |
| *Pseudomonas aurogenosa* | 17933 | MetZ | +++ | + |
|  |  | MetY | ++++ | ++++ |
| *Pseudomonas putida* | 17390 | MetZ | ++++ | + |
| *Corynebacterium glutamicum* | 13032 | MetB | + | + |
|  |  | MetY | + | + |
| *Leptospira meyeri* | 43278 | MetY | + | ++ |
| *Saccharomyces cerevisiae* | 2704 | Met25 | + | + |
| *Chromobacterium Violaceum* | 12472 | MetZ | ++++ | +++ |
| *Nocardia Farcinica* | 3318 | MetZ | ++++ | + |
| *Bradyrhizobium Japonicum* | 10324 | MetZ | + | + |
| *Hyphomonas Neptunium* | 49408 | MetZ | + | ++++ |
| *Methylococcus Capsulatus* | 19069D-5 | MetZ | + | + |
| *Methylobacillus Flagellatus* | 51484D | MetZ | + | + |
| *Nitrosomonas Europaea* | 19718D | MetZ | + | + |
| *Klebsiella Pneumoniae* | 25955 | MetB | + | + |
| *Bacillus Subtilis* | 10783 | MetB | + | + |
| *Shigella flexneri* 2457T | 700930D-5 | MetB | + | + |
| *Colwellia Psychrerythraea* | BAA-618D | MetB | + | + |
| *Salmonella enterica serovar Paratyphi* A | 9150D | MetB | + | + |

TABLE 7

Production capacity of methionine and succinic acid from O-succinylhomoserine by each enzyme

| Enzyme gene | amount of Methionine (g/L) | amount of Succinic acid (g/L) |
|---|---|---|
| *Corynebacterium glutamicum* metB | 0.05 | 0.03 |
| *Escherichia Coli* metB | 0.14 | 0.1 |
| *Nocardia Farcinica* metZ | 0.21 | 0.17 |
| *Pseudomonas putida* metZ | 0.22 | 0.17 |
| *Pseudomonas aurogenosa* metZ | 0.22 | 0.17 |
| *Chromobacterium Violaceum* | 0.22 | 0.17 |
| *Pseudomonas aurogenosa* metY | 0.21 | 0.17 |

TABLE 8

Production of methionine and acetic acid from O-acetylhomoserine by each enzyme

| Enzyme gene | Amount of Methionine (g/L) | amount of Acetic acid (g/L) |
|---|---|---|
| Pseudomonas aurogenosa metY | 0.22 | 0.081 |
| Chromobacterium Violaceum metZ | 0.18 | 0.068 |
| Hyphomonas Neptunium metZ | 0.22 | 0.082 |
| Corynebacterium glutamicum metY | 0.05 | 0.015 |
| Leptospira meyeri metY | 0.15 | 0.05 |

<1-22> Identification of Feed-Back Inhibition for Converting Enzyme

Feed-back inhibition in the presence or absence of methionine was identified by the same manner as described in Examples <3-20> and <3-21>. The reaction solutions were prepared by the same manner above and the same reaction was performed by adding or not adding 5 g/L of methionine in the each reaction solution. The reaction speed in the reaction solution without methionine was regarded as 100%, based on which the remaining activity in the presence of methionine was calculated as %. The results are shown in table 9.

As a result, the activity of each O-acetylhomoserine sulfhydrylase derived from *Pseudomonas* sp., O-succinylhomoserine sulfhydrylase derived from *Nocardia* sp. and O-acetylhomoserine sulfhydrylase derived from *Leptospira* sp. was inhibited by methionine, suggesting that those enzyme activities were inhibited by feed-back system in the presence of methionine. Enzymes without feed-back system were used for further reactions. It was presumed that the enzyme was inhibited by feed-back system in the above embodiment to be used in the same reaction where a mutant strain free from feed-back system was used.

TABLE 9

Inhibition of enzyme activity by methionine

| Enzyme gene | Remaining activity (%) OSHS | Remaining activity (%) OAHS |
|---|---|---|
| Chromobacterium Violaceum metZ | 97 | 100 |
| Pseudomonas aurogenosa metY | 54 | 53 |
| Nocardia Farcinica metZ | 68 | |
| Pseudomonas putida metZ | 98 | |
| Pseudomonas aurogenosa metZ | 98 | |
| Leptospira meyeri metY | | 45 |
| Hyphomonas Neptunium metZ | | 100 |

<1-23> Comparison of Homology Among the Converting Enzymes

Homology among the converting enzymes used for the conversion reaction was compared to investigate the interactions of the reactivity to O-succinylhomoserine and O-acetylhomoserine and the feed-back inhibition.

From the comparison of homology among the converting enzymes used herein, it was confirmed that the homology between metZs encoding O-succinylhomoserine sulfhydrylase and the homology between metYs encoding O-acetylhomoserine sulfhydrylase were higher than the homology between metZs and metYs. In connection with the above embodiment, there are many case of the metZ encoding O-succinylhomoserine sulfhydrylase which does not exhibit the feed-back inhibition. However, it was identified that the metY encoding O-acetylhomoserine sulfhydrylase was inhibited by relatively high feed-back system because all the enzymes used in the examples were inhibited by feedback. Regarding the selectivity to O-succinylhomoserine and O-acetylhomoserine, the metZ gene group exhibited high selectivity to O-succinylhomoserine, while the metY gene group exhibited high selectivity to O-acetylhomoserine. In the meantime, metY derived from *Pseudomonas putida* and metZ derived from *Chromobacterium Violaceum* exhibited specifically high reactivity to both substrates.

The amino acid sequences of all the enzymes used herein were aligned by Clustal W program (DNAstar). As a result, they all have the domains represented by the following sequences. Therefore, the enzymes that have the following domains can produce methionine by the same manner.

```
Domain 1:
Y-(S,I,T,V)-R-X-X -(N,S)  (SEQ ID NO: 72)

Domain 2:
(V,A,I)-(V,L,I)-D-N-X-(F,V,M,I)-X-(T,S)-(P,A)-
X-(L,I)-(Q,C,V)-X-(P,G)-(L,F)-X-(L,M,H)-G-
(A,V)-(D,H)  (SEQ ID NO: 73)

Domain 3:
(S,A,G,P)-(P,A,V)-F-(N,D)-(A,S)-(W,F,Y)-X-X-X-
(K,Q,R,S)-G-(L,M,V,I,M)-(E,K,D,R)-T-(L,M)-
(SEQ ID NO: 74)

Domain 5:
(H,Y)-(P,A)-(A,S)-(T,S)-(T,M,Q)-(T,S)-H
(SEQ ID NO: 75)

Domain 6:
(V,I,L)-R-(V,I,L,F)-(S,A)-(V,I,T)-G-(L,I)-E-
(SEQ ID NO: 76)
```

Example 4

Methionine Conversion Reaction by Methionine Converting Enzyme

<4-1> Mass-Production of Converting Enzyme

To mass-produce the strain of producing methionine converting enzyme constructed in Example 2 (2-2 and 2-8), the strain was cultured in a 1 L fermentor. A strain(W3110) was transformed with metZ expression vector derived from *Pseudomonas* sp. or metZ expression vector derived from *Hyphomonas* sp. The transformed strains were inoculated on LB plate medium containing spectinomycin, followed by culture at 30-40° C. for overnight. The obtained single colony was inoculated in 40 ml of LB medium containing spectinomycin, followed by culture at 30-40° C. for 5 hours. The cultured metZ expressing strain derived from *Pseudomonas* sp. and metZ expressing strain derived from *Hyphomonas* sp. were cultured in a 1 L fermentor at 30-40° C., 600-900 rpm for 15-30 hours. The composition of the medium for the culture is shown in Table 10.

The methionine converting enzyme solution was prepared by homogenizing cells of the fermented solution using sonication.

TABLE 10

Composition of the medium for the production of converting enzyme

| 2XYT medium composition | |
|---|---|
| Yeast extract (g/L) | 10 |
| Tryptophan (g/L) | 16 |
| Glucose (g/L) | 40 |
| Spectinomycin (g/L) | 50 |

<4-2> Methionine Conversion Reaction

Methionine conversion reaction was performed by using O-succinylhomoserine converting enzyme solution derived from *Pseudomonas* sp. and O-acetylhomoserine converting enzyme solution derived from *Hyphomonas* sp. prepared in Example 4 (4-1) respectively in the fermentation solution of O-succinylhomoserine and O-acetylhomoserine prepared in Example 2 (2-2).

0.1 L of cell-lysed enzyme culture solution was added to 2.0 L of fermentation solution of methionine precursor which did not remove the cell, to which 0.3 L of 15% Na-methylmercaptan was added to initiate the reaction. Two hours later, the fermentation solution was recovered and cells were removed. HPLC was performed to confirm the methionine production. The results are shown in Table 11.

TABLE 11

|  | L-methionine (g/L) | Succinic acid (g/L) | Acetic acid (g/L) |
|---|---|---|---|
| Fermentation solution of O-succinylhomoserine (>80 g/L) | >42 | >33 | 0 |

TABLE 11-continued

|  | L-methionine (g/L) | Succinic acid (g/L) | Acetic acid (g/L) |
|---|---|---|---|
| Fermentation solution of O-acetylhomoserine (>55 g/L) | >40 | 0 | >15 |

As a result, while L-methionine was produced with low concentration of up to 10 g/L in the conventional method, L-methionine could be mass-produced by the method of the present invention at the concentration of up to 30 g/L.

INDUSTRIAL APPLICABILITY

The method of the invention enables the selective production of L-methionine, which is superior to the conventional chemical synthesis producing D-methionine and L-methionine together, and the production of organic acid such as succinic acid or acetic acid as a by-product without additional independent processes.

What is claimed is:

1. A method for producing L-methionine and organic acid, which comprises the following steps:
   i) producing L-methionine precursor in a fermentation medium by the fermentation of an L-methionine precursor-producing microbial strain, wherein the L-methionine precursor-producing microbial strain is prepared by deleting the activity of cystathionine gamma synthase or O-succinylhomoserine sulfhydrylase or O-acetylhomoserine sulfhydrylase involved in the degradation of L-methionine precursor and by enhancing the activity of homoserine O-succinyl transferase or homoserine O-acetyl transferase involved in L-methionine precursor synthesis from homoserine; and
   ii) producing L-methionine and organic acid outside of the L-methionine precursor-producing microbial strain by the enzyme reaction using the L-methionine precursor and methylmercaptan or its salts as substrates, wherein the enzyme reaction is performed by other microbial strains containing the activity of cystathionine gamma synthase or O-succinylhomoserine sulfhydrylase or O-acetylhomoserine sulfhydrylase, wherein the L-methionine precursor is O-acetylhomoserine or O-succinylhomoserine.

2. The method of claim 1, wherein the L-methionine precursor-producing microbial strain is selected from the group consisting of *Escherichia* sp. and *Corynebacterium* sp.

3. The method of claim 1, wherein the cystathionine gamma synthase or O-succinylhomoserine sulfhydrylase or O-acetylhomoserine sulfhydrylase of step i) is encoded, respectively, by metB, metZ, and metY, or functional mutants thereof.

4. The method of claim 1, wherein the L-methionine precursor-producing microbial strain is the strain whose threonine, isoleucine or lysine biosynthesis pathway is weakened or deleted.

5. The method of claim 1, wherein the microbial strain is characterized by deleting or weakening of homoserine kinase encoded by thrB gene.

6. The method of claim 1, wherein the L-methionine precursor production is enhanced by the over-expression of metA gene encoding homoserine O-succinyl transferase or metX gene encoding homoserine O-acetyl transferase.

7. The method of claim 1, wherein the homoserine O-succinyl transferase gene of a microorganism is deleted or weakened, and then a new foreign or mutant homoserine O-acetyl transferase gene is introduced in order to enhance the synthesis of O-acetylhomoserine, or wherein the homoserine O-acetyl transferase gene of a microorganism is deleted or weakened, and then a new foreign or mutant homoserine O-succinyl transferase gene is introduced in order to enhance the biosynthesis of O-succinylhomoserine.

8. The method of claim 1, wherein the other microbial strain is selected from the group consisting of *Escherichia* sp., *Corynebacterium* sp., *Pseudomonas* sp., *Leptospira* sp., *Salmonellar* sp., *Brevibacterium* sp., *Hyphomonas* sp., *Chromobacterium* sp., *Nocardia* sp., and yeasts.

9. The method of claim 1, wherein the other microbial strain is selected from the group consisting of: *Escherichia Coli, Pseudomonas aurogenosa, Pseudomonas putida, Corynebacteria glutamicum, Leptospira meyeri, Saccharomyces cerevisiae, Chromobacterium Violaceum, Nocardia Farcinica, Bradyrhizobium Japonicum, Hyphomonas Neptunium, Methylococcus Capsulatus, Methylobacillus Flagellatus, Nitrosomonas Europaea, Klebsiella Pneumoniae, Bacillus Subtilis, Shigella flexneri, Colwellia Psychreryth-raea*, and *Salmonella enterica serovar Paratyphi* A.

10. The method of claim 1, wherein said the L-methionine precursor is an O-acylhomoserine.

11. The method of claim 1, wherein the L-methionine precursor-producing microbial strain of step i) is selected from the group consisting of *Escherichia* sp., *Erwinia* sp., *Serratia* sp., *Providencia* sp., *Corynebacterium* sp., *Pseudomonas* sp., *Leptospira* sp., *Salmonellar* sp., *Brevibacterium* sp., *Hyphomonas* sp., *Chromobacterium* sp. and *Nocardia* sp., fungi, and yeasts.

12. The method of claim 11, wherein the L-methionine precursor-producing microbial strain is selected from *Escherichia* sp. and *Corynebacterium* sp.

13. The method of claim 12, wherein the L-methionine precursor-producing microbial strain is *Escherichia* coli.

14. The method of claim 12, wherein the L-methionine precursor-producing microbial strain is *Corynebacterium* glutamicum.

15. The method of claim 1, wherein the L-methionine precursor-producing microbial strain is the strain whose L-methionine precursor synthesis pathway from homoserine is enhanced.

16. The method of claim 1, wherein the L-methionine precursor synthesis is enhanced by the over-expression of metA gene encoding homoserine O-succinyl transferase or metX gene encoding homoserine O-acetyl transferase.

* * * * *